US010760065B2

(12) United States Patent
Lu et al.

(10) Patent No.: US 10,760,065 B2
(45) Date of Patent: Sep. 1, 2020

(54) TUNING MICROBIAL POPULATIONS WITH PROGRAMMABLE NUCLEASES

(71) Applicant: Massachusetts Institute of Technology, Cambridge, MA (US)

(72) Inventors: Timothy Kuan-Ta Lu, Charlestown, MA (US); Robert James Citorik, Kingston, NH (US); Mark Kyle Mimee, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/475,785

(22) Filed: Sep. 3, 2014

(65) Prior Publication Data

US 2015/0064138 A1 Mar. 5, 2015

Related U.S. Application Data

(60) Provisional application No. 62/010,976, filed on Jun. 11, 2014, provisional application No. 61/873,894, filed on Sep. 5, 2013.

(51) Int. Cl.

| | |
|---|---|
| ***C12N 9/22*** | (2006.01) |
| ***A61K 38/46*** | (2006.01) |
| ***C12N 15/74*** | (2006.01) |

(52) U.S. Cl.
CPC .............. *C12N 9/22* (2013.01); *A61K 38/465* (2013.01); *C12N 15/74* (2013.01)

(58) Field of Classification Search
None
See application file for complete search history.

(56) References Cited

U.S. PATENT DOCUMENTS

| | | | | |
|---|---|---|---|---|
| 4,683,202 | A | 7/1987 | Mullis | |
| 5,928,906 | A | 7/1999 | Koster et al. | |
| 2004/0091878 | A1* | 5/2004 | Sera | C12N 15/8216 435/6.12 |
| 2005/0124010 | A1* | 6/2005 | Short | C12N 15/102 435/7.23 |
| 2009/0205083 | A1* | 8/2009 | Gupta | C12N 15/8213 800/298 |
| 2010/0076057 | A1* | 3/2010 | Sontheimer | A61K 31/7088 514/44 A |
| 2012/0027786 | A1* | 2/2012 | Gupta | C07K 14/21 424/184.1 |

FOREIGN PATENT DOCUMENTS

| | | | |
|---|---|---|---|
| WO | WO 2007/025097 | A2 | 3/2007 |
| WO | WO 2010/075424 | A2 | 7/2010 |
| WO | WO 2012/164565 | A1 | 12/2012 |
| WO | WO 2013/176772 | A1 | 11/2013 |
| WO | WO 2014/093595 | A9 | 6/2014 |
| WO | WO 2014/124226 | A1 | 8/2014 |

OTHER PUBLICATIONS

Kawamura et al. 1995 (Determination of 16S rRNA Sequences of *Streptococcus mitis* and *Streptococcus gordonii* and Phylogenetic Relationships among Members of the Genus *Streptococcus*; International Journal of Systematic Bacteriology; 45(2):406-408).*

Marraffini et al. 2008 (CRISPR Interference Limits Horizontal Gene Transfer in Staphylococci by Targeting DNA; Science 322:1843-1845).*

Guiral et al. 2006 (Construction and evaluation of a chromosomal expression platform (CEP) for ectopic, maltose-driven gene expression in *Streptococcus pneumoniae*; Microbiology 152:343-349).*

Pul et al. 2010 (Identification and characterization of *E. coli* CRISPR-Cas promoters and their silencing by H-NS; Molecular Microbiology 75(6):1495-1512).*

Voight 2006 (Genetic Parts to Program Bacteria; Current Opinion in Biotechnology 17:548-557).*

Trieu-Cuot et al. 1987 (Plasmid transfer by conjugation from *Escherichia coli* to Gram positive bacteria; FEMS Microbiology Letters 48:289-294).*

Simon et al. 1983 (A broad host range mobilization system for in vivo genetic engineering: Transposon mutagenesis in Gram negative Bacteria; Biotechnology; Nov. 1983: 784-791).*

Jinek et al. 2012 (A Programmable Dual-RNA-Guided DNA Endonuclease in Adaptive Bacterial Immunity; Science 337: 816-821.*

Kawamura et al. 1995 (International Journal of Systematic Bacteriology; 45(2):406-408.*

Igimi et al. 1996 (Transfer of conjugative plasmid pAMb1 from Lactococcus lactis to mouse intestinal bacteria; Letters in Applied Microbiology 23:31-35).*

Bikard et al. 2012 (CRISPR interference can prevent natural transformation and virulence acquisition during in vivo bacterial infection; Cell Host & Microbe 12:177-186).*

Gaj et al. 2013 (ZFN, TALEN, and CRISPR/Cas-based methods for genome engineering; Trends in Biotechnology 31(7): 397-405).*

Jinek et al. 2012 (A programmable Dual RNA-Guided DNA Endonuclease in Adaptaive Bacterial Immunity; Science 337:816-821).*

Vollmer et al. 1997 (Detection of DNA Damage by Use of *Escherichia coli* carrying recA'::lux, uvrA'::lux or alkA'::lux Reporter plasmids; Applied and Environmental Microbiology 63(7): 2566-2571).*

Fabre et al. 2012 (CRISPR typing and subtyping for improved laboratory surveillance of *Salmonella* infections; PLOS ONE 7(5):1-20).*

(Continued)

*Primary Examiner* — Mary Maille Lyons
(74) *Attorney, Agent, or Firm* — Wolf, Greenfield & Sacks, P.C.

(57) ABSTRACT

Various aspects and embodiments of the invention are directed to methods and compositions for reversing antibiotic resistance or virulence in and/or destroying pathogenic microbial cells such as, for example, pathogenic bacterial cells. The methods include exposing microbial cells to a delivery vehicle with at least one nucleic acid encoding an engineered autonomously distributed circuit that contains a programmable nuclease targeted to one or multiple genes of interest.

20 Claims, 19 Drawing Sheets

Specification includes a Sequence Listing.

(56) References Cited

OTHER PUBLICATIONS

Mead et al. 1988 (Chimeric single-stranded DNA phage-plasmid cloning vectors; Biotechnology 10:85-102).*
Vankemmelbeke et al. 2005 (Rapid Detection of Colicin E9-Inced DNA Damage Using *Escherichia coli* Cells Carrying SOS promoter-lux Fusions; Journal of Bacteriology 187(14): 4900-4907) (Year: 2005).*
Maslowska et al. 2018 (The SOS-System: A complex and tightly regulated response to DNA damage; Environmental and Molecular Mutagenesis; DOI 10.1002/EM.22267 (Year: 2018).*
O'Neill et al. 2011 (Intestinal delivery of non-viral gene therapeutics: physiological barriers and preclinical models; Drug Discovery Today 16(5/6): 203-218) (Year: 2011).*
Heitman et al. 1991 (SOS induction as an in vivo assay of enzyme-DNA interactions; Gene 103: 1-9) (Year: 1991).*
Afendra et al., Expression and stability of a recombinant plasmid in Zymomonas mobilis and *Escherichia coli*. J Gen Microbiol. Jan. 1987;133(1):127-34.
Bikard et al., CRISPR interference can prevent natural transformation and virulence acquisition during in vivo bacterial infection. Cell Host Microbe. Aug. 16, 2012;12(2):177-86. doi: 10.1016/j.chom.2012.06.003.
Ellis et al., Zinc-finger nuclease-mediated gene correction lasing single AAV vector transduction and enhancement by Food and Drug Administration-approved drugs. Gene Ther. Jan. 2013;20(1):35-42. doi: 10.1038/gt.2011.211. Epub Jan. 19, 2012.
Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012.
Jepson et al., Bacteriophage lambda is a highly stable DNA vaccine delivery vehicle. Vaccine. Jun. 23, 2004;22(19):2413-9.
Lu et al., Engineered bacteriophage targeting gene networks as adjuvants for antibiotic therapy. Proc Natl Acad Sci U S A. Mar. 24, 2009;106(12):4629-34. doi: 10.1073/pnas.0800442106. Epub Mar. 2, 2009.
McCool et al., Measurement of SOS expression in individual *Escherichia coli* K-12 cells using fluorescence microscopy. Mol Microbiol. Sep. 2004;53(5):1343-57.
Sapranauskas et al., The *Streptococcus thermophiles* CRISPR/Cas system provides immunity in *Escherichia coli*. Nucleic Acids Res. Nov. 2011;39(21):9275-82. doi: 10.1093/nar/gkr606. Epub Aug. 3, 2011.
Schmid-Burgk et al., A ligation-independent cloning technique for high-throughput assembly of transcription activator-like effector genes. Nat Biotechnol. Jan. 2013;31(1):76-81.
Westwater et al., Development of a P1 phagemid system for the delivery of DNA into Gram-negative bacteria. Microbiology. Apr. 2002;148(Pt 4):943-50.
Abedon et al., Phage treatment of human infections. Bacteriophage. Mar. 2011;1(2):66-85.
Bikard et al., CRISPR Interference Can Prevent Natural Transformation and Virulence Acquisition during In Vivo Bacterial Infection. Cell Host & Microbe, 2012; 12: 177-86.
Bitinaite et al., Fold dimerization is required for DNA cleavage. Proc Natl Acad Sci U S A. Sep. 1, 1998; 95(18): 10570-5.
Chasteen et al., Eliminating helper phage from phage display. Nucleic Acids Res. 2006;34(21):e145. Epub Nov. 6, 2006. 11 pages.
Christian et al., Targeting DNA Double-Strand Breaks with TAL Effector Nucleases. Genetics. Oct. 2010; 186(2): 757-61. doi: 10.1534/genetics.110.120717.
Chung et al., One-step preparation of competent *Escherichia coli*: transformation and storage of bacterial cells in the same solution. Proc Natl Acad Sci U S A. Apr. 1989;86(7):2172-5.
Cong et al., Multiplex Genome Engineering Using CRISPR/Cas Systems. Science. Feb. 15, 2013; 339(6121): 819-23. Author manuscript.
Damron et al., Construction of a broad-host-range Tn7-based vector for single-copy P(BAD)-controlled gene expression in gram-negative bacteria. Appl Environ Microbiol. Jan. 2013;79(2):718-21. doi: 10.1128/AEM.02926-12. Epub Nov. 2, 2012.
Datsenko et al., One-step inactivation of chromosomal genes in *Escherichia coli* K-12 using PCR products. Proc Natl Acad Sci U S A. Jun. 2000 6;97(12):6640-5.
Deltcheva et al., CRISPR RNA maturation by trans-encoded small RNA and host factor RNase III. Nature. Mar. 31, 2011;471(7340):602-7. doi: 10.1038/nature09886. Author manuscript.
Desbois et al., Wax moth larva (*Galleria mellonella*): an in vivo model for assessing the efficacy of antistaphylococcal agents. J Antimicrob Chemother. Aug. 2011;66(8):1785-90. doi: 10.1093/jac/dkr198. Epub May 28, 2011.
Dong et al., Novel antibiotic-free plasmid selection system based on complementation of host auxotrophy in the NAD de novo synthesis pathway. Appl Environ Microbiol. Apr. 2010;76(7):2295-303. doi: 10.1128/AEM.02462-09. Epub Jan. 29, 2010.
Duan et al., Engineered bacterial communication prevents Vibrio cholerae virulence in an infant mouse model. Proc Natl Acad Sci U S A. Jun. 22, 2010;107(25):11260-4. doi: 10.1073/pnas.1001294107. Epub Jun. 7, 2010.
Dwyer et al., Gyrase inhibitors induce an oxidative damage cellular death pathway in *Escherichia coli*. Mol Syst Biol. 2007;3:91. Epub Mar. 13, 2007. 15 pages.
Edgar et al., Reversing bacterial resistance to antibiotics by phage-mediated delivery of dominant sensitive genes. Appl Environ Microbiol. Feb. 2012;78(3):744-51. doi: 10.1128/AEM.05741-11. Epub Nov. 23, 2011.
Fotakis et al., In vitro cytotoxicity assays: comparison of LDH, neutral red, MTT and protein assay in hepatoma cell lines following exposure to cadmium chloride. Toxicol Lett. Jan. 5, 2006;160(2):171-7. Epub Aug. 18, 2005.
Friedland et al., Synthetic gene networks that count. Science. May 29, 2009;324(5931):1199202. doi: 10.1126/science.1172005. Author manuscript.
Gibson et al., Enzymatic assembly of DNA molecules up to several hundred kilobases. Nature Methods, 2009; 6(5): 343-5.
Gold, Vancomycin-resistant enterococci: mechanisms and clinical observations. Clin Infect Dis. Jul. 15, 2001;33(2):210-9. Epub Jun. 14, 2001.
Gordley et al., Synthesis of programmable integrases. Proc Natl Acad Sci U S A. Mar. 31, 2009; 106(13): 5053-8.
Grohmann et al., Conjugative plasmid transfer in gram-positive bacteria. Microbiol Mol Biol Rev. Jun. 2003;67(2):277-301, table of contents.
Groth et al., Phage Integrases: Biology and Applications. J Mol Biol, 2004; 335: 667-78.
Gunderson et al., The CRISPR-Associated Gene cas2 of Legionella pneumophila Is Required for Intracellular Infection of Amoebae. mBio. Mar.-Apr. 2013; 4(2): e00074-13. Published online Mar. 12, 2013. doi: 10.1128/mBio.00074-13. 11 pages.
Hagens et al., Augmentation of the antimicrobial efficacy of antibiotics by filamentous phage. Microb Drug Resist. 2006 Fall;12(3):164-8.
Hagens et al., Therapy of experimental pseudomonas infections with a nonreplicating genetically modified phage. Antimicrob Agents Chemother. Oct. 2004;48(10):3817-22.
Hwang et al., Efficient genome editing in zebrafish using a CRISPR-Cas system Nat Biotechnol. Mar. 2013;31(3):227-9. doi: 10.1038/nbt.2501. Epub Jan. 29, 2013. Author manuscript.
Jacoby, Mechanisms of resistance to quinolones. Clin Infect Dis. Jul. 15, 2005;41 Suppl 2:S120-6.
Jiang et al., CRISPR-assisted editing of bacterial genomes. Nat Biotechnol. Mar. 2013; 31(3): 233-9. Author manuscript.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Karvelis et al., crRNA and tracrRNA guide Cas9-mediated DNA interference in *Streptococcus thermophilus*. RNA Biol. May 2013;10(5):841-51. doi: 10.4161/rna.24203. Epub Mar. 27, 2013.
Khalil et al., A synthetic biology framework for programming eukaryotic transcription functions. Cell. Aug. 3, 2012;150(3):647-58. doi: 10.1016/j.cell.2012.05.045. Author manuscript.

(56) References Cited

OTHER PUBLICATIONS

Kim et al., Hybrid restriction enzymes: zinc finger fusions to Fok I cleavage domain. Proc Natl Acad Sci U S A. Feb. 6, 1996; 93(3): 1156-60.
Kittleson et al., Scalable plasmid transfer using engineered P1-based phagemids. ACS Synth Biol. Dec. 21, 2012;1(12):583-9. doi: 10.1021/sb300054p. Epub Aug. 30, 2012. Author manuscript.
Kohanski et al., A common mechanism of cellular death induced by bactericidal antibiotics. Cell. Sep. 7, 2007;130(5):797-810.
Konowalchuk et al., Vero response to a cytotoxin of *Escherichia coli*. Infect Immun. Dec. 1977;18(3):775-9.
Labrie et al., Bacteriophage resistance mechanisms. Nat Rev Microbiol. May 2010;8(5):317-27. doi: 10.1038/nrmicro2315. Epub Mar. 29, 2010.
Lin et al., A T3 and T7 recombinant phage acquires efficient adsorption and a broader host range. PLoS One. 2012;7(2):e30954. doi: 10.1371/journal.pone.0030954. Epub Feb. 9, 2012. 10 pages.
Lin et al., Inhibition of Bacterial Conjugation by Phage M13 and Its Protein g3p: Quantitative Analysis and Model. PLoS One. 2011; 6(5): e19991. 11 pages.
Loessner et al., Complete nucleotide sequence, molecular analysis and genome structure of bacteriophage A118 of Listeria monocytogenes: implications for phage evolution. Mol. Micro. 2000; 35: 324-40.
Lorbach et al., Site-specific recombination in human cells catalyzed by phage lambda integrase mutants. J Mol Biol. Mar. 10, 2000;296(5):1175-81.
Lu et al., Dispersing biofilms with engineered enzymatic bacteriophage. Proc Natl Acad Sci U S A. Jul. 3, 2007;104(27):11197-202. Epub Jun. 25, 2007.
Lutz et al., Independent and tight regulation of transcriptional units in *Escherichia coli* via the LacR/O, the TetR/O and AraC/I1-12 regulatory elements. Nucleic Acids Res. Mar. 15, 1997;25(6):1203-10.
Magadan et al., Cleavage of phage DNA by the *Streptococcus thermophilus* CRISPR3-Cas system. PLoS One. 2012;7(7):e40913. doi: 10.1371/journal.pone.0040913. Epub Jul. 20, 2012. 8 pages.
Mali et al., RNA-Guided Human Genome Engineering via Cas9. Science. Feb. 15, 2013; 339(6121): 823-6.
Manley et al., Probiotic treatment of vancomycin-resistant enterococci: a randomised controlled trial. Med J Aust. May 7, 2007;186(9):454-7.
Martinez et al., Mutation frequencies and antibiotic resistance. Antimicrob Agents Chemother. Jul. 2000;44(7):1771-7.
Meyer, Replication and conjugative mobilization of Broad Host-range IncQ plasmids. Plasmid. Sep. 2009; 62(2): 57-70. Author manuscript.
Matsuura et al., The sre gene (ORF469) encodes a site-specific recombinase responsible for integration of the R4 phage genome. J Bacteriol. Jun. 1996;178(11):3374-6.
Mnif et al., Molecular characterization of addiction systems of plasmids encoding extended-spectrum beta-lactamases in *Escherichia coli*. J Antimicrob Chemother. Aug. 2010;65(8):1599-603. doi: 10.1093/jac/dkq181. Epub May 27, 2010.
Ow et al., Conditionally replicating plasmid vectors that can integrate into the Klebsiella pneumoniae chromosome via bacteriophage P4 site-specific recombination. J Bacteriol. Aug. 1983; 155(2): 704-13.
Paddon et al., High-level semi-synthetic production of the potent antimalarial artemisinin. Nature. Apr. 25, 2013;496(7446):528-32. doi: 10.1038/nature12051. Epub Apr. 10, 2013.
Paton et al., Pathogenesis and diagnosis of Shiga toxin-producing *Escherichia coli* infections. Clin Microbiol Rev. Jul. 1998;11(3):450-79.
Pennington et al., Spontaneous DNA breakage in single living *Escherichia coli* cells. Nat Genet. Jun. 2007;39(6):797-802. Epub May 27, 2007. Author manuscript.
Pérez-Mendoza et al., *Escherichia coli* genes affecting recipient ability in plasmid conjugation: are there any? BMC Genomics. Feb. 9, 2009;10:71. doi: 10.1186/1471-2164-10-71. 14 pages.
Radovic-Moreno et al., Surface charge-switching polymeric nanoparticles for bacterial cell wall-targeted delivery of antibiotics. ACS Nano. May 22, 2002;6(5):4279-87. doi: 10.1021/nn3008383. Epub Apr. 12, 2002. Author manuscript.
Ramarao et al., The insect Galleria mellonella as a powerful infection model to investigate bacterial pathogenesis. J Vis Exp. Dec. 11, 2012;(70):e4392. doi: 10.3791/4392. 7 pages.
Rasheed et al., Characterization of the Extended-Spectrum (β-Lactamase Reference Strain, Klebsiella pneumoniae K6 (ATCC 700603), Which Produces the Novel Enzyme SHV-18. Antimicrob Agents Chemother. Sep. 2000; 44(9): 2382-8.
Rasheed et al., New Delhi Metallo-β-Lactamase-producing Enterobacteriaceae, United States. Emerg Infect Dis. Jun. 2013; 19(6): 870-8.
Rice et al., Transferable capacity for gastrointestinal colonization in Enterococcus faecium in a mouse model. J Infect Dis. Feb. 1, 2009;199(3):342-9. doi: 10.1086/595986.
Saeidi et al., Engineering microbes to sense and eradicate Pseudomonas aeruginosa, a human pathogen. Mol Syst Biol. Aug. 16, 2011;7:521. doi: 10.1038/msb.2011.55. 11 pages.
Sapranauskas et al., The *Streptococcus thermophilus* CRISPR/Cas system provides immunity in *Escherichia coli*. Nucleic Acids Res. Nov. 2011;39(21):9275-82. doi: 10.1093/nar/gkr606. Epub Aug. 3, 2011.
Schleif, Fine-structure deletion map of the *Escherichia coli* L-arabinose operon. Proc Natl Acad Sci U S A. Nov. 1972;69(11):3479-84.
Seed et al., A bacteriophage encodes its own CRISPR/Cas adaptive response to evade host innate immunity. Nature. Feb. 28, 2013;494(7438):489-91. doi: 10.1038/nature11927. Author manuscript.
Seed et al., Experimental bacteriophage therapy increases survival of Galleria mellonella larvae infected with clinically relevant strains of the Burkholderia cepacia complex. Antimicrob Agents Chemother. May 2009;53(5):2205-8. doi: 10.1128/AAC.01166-08. Epub Feb. 17, 2009.
Sharan et al., Recombineering: a homologous recombination-based method of genetic engineering. Nat Protoc. 2009;4(2):206-23. doi: 10.1038/nprot.2008.227. Author manuscript.
Sikorski et al., A system of shuttle vectors and yeast host strains designed for efficient manipulation of DNA in *Saccharomyces cerevisiae*. Genetics. May 1989;122(1):19-27.
Siuti et al., Synthetic circuits integrating logic and memory in living cells. Nat Biotechnol. May 2013;31(5):448-52. doi: 10.1038/nbt.2510. Epub Feb. 10, 2013. 39 pages.
Smillie et al., Mobility of plasmids. Microbiol Mol Biol Rev. Sep. 2010;74(3):434-52. doi: 10.1128/MMBR.00020-10.
Sonnenburg et al., Community health care: therapeutic opportunities in the human microbiome. Sci Transl Med. Apr. 13, 2011;3(78):78ps12. doi: 10.1126/scitranslmed.3001626. Author manuscript.
Van Hal et al., Is it time to replace vancomycin in the treatment of methicillin-resistant *Staphylococcus aureus* infections? Clin Infect Dis. Jun. 2013;56(12):1779-88. doi: 10.1093/cid/cit178. Epub Mar. 19, 2013.
Vercoe et al., Cytotoxic chromosomal targeting by CRISPR/Cas systems can reshape bacterial genomes and expel or remodel pathogenicity islands. PLoS Genet. Apr. 2013;9(4):e1003454. doi: 10.1371/journal.pgen.1003454. Epub Apr. 18, 2013. 13 pages.
Weber et al., A synthetic mammalian gene circuit reveals antituberculosis compounds. Proc Natl Acad Sci U S A. Jul. 22, 2008;105(29):9994-8. doi: 10.1073/pnas.0800663105. Epub Jul. 9, 2008.
Westwater et al., Use of genetically engineered phage to deliver antimicrobial agents to bacteria: an alternative therapy for treatment of bacterial infections. Antimicrob Agents Chemother. Apr. 2003;47(4):1301-7.
Williams et al., Artificial activation of toxin-antitoxin systems as an antibacterial strategy. Trends Microbiol. Jun. 2012;20(6):291-8. doi: 10.1016/j.tim.2012.02.005. Epub Mar. 22, 2012. Author manuscript.
Cathomen et al., Zinc-finger Nucleases: The Next Generation Emerges. Molecular Therapy. 2008; 16(7): 1200-7.

(56) References Cited

OTHER PUBLICATIONS

Cho et al., Targeted genome engineering in human cells with the Cas9 RNA-guided endonuclease. Nature Biotechnology. Mar. 2013; 31(3):230-2.
Fernandez, In Vivo Animal Models. Quantitative Models Used for Identifying Antibacterial Agents. Current Protocols in Pharmacology. Oct. 2006; Chapter 13:Unit13A.15. doi: 10.1002/0471141755.ph13a05s34. 12 pages.
Filutowicz et al., Bacterial conjugation-based antimicrobial agents. Plasmid, 2008; 60:38-44.
Lu et al., The next generation of bacteriophage therapy. Current Opinion in Microbiology. 2011; 14:524-31.
Nordmann et al., Carbapenem resistance in Enterobacteriaceae: here is the storm! Trends in Molecular Medicine. May 2012;18(5):263-72. doi: 10.1016/j.molmed.2012.03.003. Epub Apr. 3, 2012.
Bikard et al., Exploiting CRISPR-Cas nucleases to produce sequence-specific antimicrobials. Nat Biotechnol. Nov. 2014 ;32(11):1146-50. doi:10.1038/nbt.3043. Epub Oct. 5, 2014.
Citorik et al., Sequence-specific antimicrobials using efficiently delivered Rna-guided nucleases. Nat Biotechnol. Nov. 2014;32(11):1141-5. doi:10.1038/nbt.3011. Epub Sep. 21, 2014.
Godde et al., The repetitive DNA elements called CRISPRs and their associated genes: evidence of horizontal transfer among prokaryotes. J Mol. Evol. Jun. 2006;62(6):718-29. Epub Apr. 11, 2006.
Gomaa et al., Programmable removal of bacterial strains by use of genome-targeting CRISPR-Cas systems. MBio. Jan. 28, 2014;5(1):e00928-13. doi: 10.1128/mBio.00928-13.
Qi et al., Repurposing CRISPR as an RNA-guided platform for sequence-specific control of gene expression. Cell. Feb. 28, 2013;152(5):1173-83. doi:10.1016/j.cell.2013.02.022.
Tovkach et al., Expression, purification and characterization of cloning-grade zinc finger nuclease. J Biotechnol. Jan. 10, 2011;151(1):1-8. doi:10.1016/j.jbiotec.2010.10.071. Epub Oct. 26, 2010.
Dwyer, et al., Gyrase inhibitors induce an oxidative damage cellular death pathway in *Escherichia coli*. Mol Syst Biol. 2007;3:91. Epub Mar. 13, 2007.
Fernández De Henestrosa et al., Identification of additional genes belonging to the LexA regulon in *Escherichia coli*. Mol Microbiol. Mar. 2000;35(6):1560-72.
Janion, Inducible SOS response system of DNA repair and mutagenesis in *Escherichia coli*. Int J Biol Sci. Sep. 23, 2008;4(6):338-44.
Lewis et al., Identification of high affinity binding sites for LexA which define new DNA damage-inducible genes in *Escherichia coli*. J Mol Biol. Aug. 26, 1994;241(4):507-23.
Pennington et al., Spontaneous DNA breakage in single living *Escherichia coli* cells. Nat Genet. Jun. 2007;39(6):797-802. Epub May 27, 2007. Erratum in: Nat Genet. Sep. 2007;39(9):1174.
Walker, Mutagenesis and inducible responses to deoxyribonucleic acid damage in *Escherichia coli*. Microbiol Rev. Mar. 1984;48(1):60-93.

* cited by examiner

| Mutation | Number | % |
|---|---|---|
| Deletion of spacer and one repeat | 19 | 63.3 |
| *tracrRNA* Insertion (A at nt140/141) | 6 | 20.0 |
| Transposon Insertion (Tn10.10) | 5 | 16.7 |

SEQUENCE LISTING

<160> NUMBER OF SEQ ID NOS: 74

<210> SEQ ID NO 1
<211> LENGTH: 5131
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (4948)..(4977)
<223> OTHER INFORMATION: n is a, c, g, or t

<400> SEQUENCE: 1
ccattattat catgacatta acctataaaa ataggcgtat cacgaggccc tttcgtcttc 60
accctgtcga cgcgttttga aagcgcttgt ttttttggtt tgcagtcaga gtagaataga 120
agtatcaaaa aaagcaccga ctcggtgcca ctttttcaag ttgataacgg actagcctta 180
ttttaacttg ctatgctgtt ttgaatggtt ccaacaagat tattttataa cttttataac 240
aaataatcaa ggagaaattc aaagaaattt atcagccata aaacaatact taatactata 300
gaatgataac aaaataaact actttttaaa agaattttgt gttataatct atttattatt 360
aagtattggg atcgattccc tatcagtgat agagattgac atccctatca gtgatagaga 420
tactgagcac atcagcagga cgcactgacc gaattcatta aagaggagaa aggtgcggcc 480
gcatgcatca ccatcaccat cacatggata agaaatactc aataggctta gatatcggca 540
caaatagcgt cggatgggcg gtgatcactg atgaatataa ggttccgtct aaaaagttca 600
aggttctggg aaatacagac cgccacagta tcaaaaaaaa tcttataggg gctcttttat 660
ttgacagtgg agagacagcg gaagcgactc gtctcaaacg gacagctcgt agaaggtata 720
cacgtcggaa gaatcgtatt tgttatctac aggagatttt ttcaaatgag atggcgaaag 780
tagatgatag tttctttcat cgacttgaag agtctttttt ggtggaagaa gacaagaagc 840
atgaacgtca tcctattttt ggaaatatag tagatgaagt tgcttatcat gagaaatatc 900
caactatcta tcatctgcga aaaaaattgg tagattctac tgataaagcg gatttgcgct 960
taatctattt ggccttagcg catatgatta agtttcgtgg tcattttttg attgagggag 1020
atttaaatcc tgataatagt gatgtggaca aactatttat ccagttggta caaacctaca 1080
atcaattatt tgaagaaaac cctattaacg caagtggagt agatgctaaa gcgattcttt 1140
ctgcacgatt gagtaaatca agacgattag aaaatctcat tgctcagctc cccggtgaga 1200
agaaaaatgg cttatttggg aatctcattg ctttgtcatt gggtttgacc cctaatttta 1260
aatcaaattt tgatttggca gaagatgcta aattacagct ttcaaaagat acttacgatg 1320
atgatttaga taatttattg gcgcaaattg gagatcaata tgctgatttg tttttggcag 1380
ctaagaattt atcagatgct attttacttt cagatatcct aagagtaaat actgaaataa 1440
ctaaggctcc cctatcagct tcaatgatta aacgctacga tgaacatcat caagacttga 1500
ctcttttaaa agctttagtt cgacaacaac ttccagaaaa gtataaagaa atcttttttg 1560
atcaatcaaa aaacggatat gcaggttata ttgatggggg agctagccaa gaagaatttt 1620
ataaatttat caaaccaatt ttagaaaaaa tggatggtac tgaggaatta ttggtgaaac 1680

```
taaatcgtga agatttgctg cgcaagcaac ggacctttga caacggctct attccccatc   1740
aaattcactt gggtgagctg catgctattt tgagaagaca agaagacttt tatccatttt   1800
taaaagacaa tcgtgagaag attgaaaaaa tcttgacttt tcgaattcct tattatgttg   1860
gtccattggc gcgtggcaat agtcgttttg catggatgac tcggaagtct gaagaaacaa   1920
ttaccccatg gaattttgaa gaagttgtcg ataaaggtgc ttcagctcaa tcatttattg   1980
aacgcatgac aaactttgat aaaaatcttc caaatgaaaa agtactacca aaacatagtt   2040
tgctttatga gtattttacg gtttataacg aattgacaaa ggtcaaatat gttactgaag   2100
gaatgcgaaa accagcattt ctttcaggtg aacagaagaa agccattgtt gatttactct   2160
tcaaaacaaa tcgaaaagta accgttaagc aattaaaaga agattatttc aaaaaaatag   2220
aatgttttga tagtgttgaa atttcaggag ttgaagatag atttaatgct tcattaggta   2280
cctaccatga tttgctaaaa attattaaag ataaagattt tttggataat gaagaaaatg   2340
aagatatctt agaggatatt gttttaacat tgaccttatt tgaagatagg gagatgattg   2400
aggaaagact taaaacatat gctcacctct ttgatgataa ggtgatgaaa cagcttaaac   2460
gtcgccgtta tactggttgg ggacgtttgt ctcgaaaatt gattaatggt attagggata   2520
agcaatctgg caaaacaata ttagattttt tgaaatcaga tggttttgcc aatcgcaatt   2580
ttatgcagct gatccatgat gatagtttga catttaaaga agacattcaa aaagcacaag   2640
tgtctggaca aggcgatagt ttacatgaac atattgcaaa tttagctggt agccctgcta   2700
ttaaaaaagg tattttacag actgtaaaag ttgttgatga attggtcaaa gtaatggggc   2760
ggcataagcc agaaaatatc gttattgaaa tggcacgtga aaatcagaca actcaaaagg   2820
gccagaaaaa ttcgcgagag cgtatgaaac gaatcgaaga aggtatcaaa gaattaggaa   2880
gtcagattct taaagagcat cctgttgaaa atactcaatt gcaaaatgaa aagctctatc   2940
tctattatct ccaaaatgga agagacatgt atgtggacca agaattagat attaatcgtt   3000
taagtgatta tgatgtcgat cacattgttc cacaaagttt ccttaaagac gattcaatag   3060
acaataaggt cttaacgcgt tctgataaaa atcgtggtaa atcggataac gttccaagtg   3120
aagaagtagt caaaaagatg aaaaactatt ggagacaact tctaaacgcc aagttaatca   3180
ctcaacgtaa gtttgataat ttaacgaaag ctgaacgtgg aggtttgagt gaacttgata   3240
aagctggttt tatcaaacgc caattggttg aaactcgcca aatcactaag catgtggcac   3300
aaattttgga tagtcgcatg aatactaaat acgatgaaaa tgataaactt attcgagagg   3360
ttaaagtgat taccttaaaa tctaaattag tttctgactt ccgaaaagat ttccaattct   3420
ataaagtacg tgagattaac aattaccatc atgcccatga tgcgtatcta aatgccgtcg   3480
ttggaactgc tttgattaag aaatatccaa aacttgaatc ggagtttgtc tatggtgatt   3540
ataaagttta tgatgttcgt aaaatgattg ctaagtctga gcaagaaata ggcaaagcaa   3600
ccgcaaaata tttcttttac tctaatatca tgaacttctt caaaacagaa attacacttg   3660
caaatggaga gattcgcaaa cgccctctaa tcgaaactaa tggggaaact ggagaaattg   3720
tctgggataa agggcgagat tttgccacag tgcgcaaagt attgtccatg ccccaagtca   3780
atattgtcaa gaaaacagaa gtacagacag gcggattctc caaggagtca attttaccaa   3840
aaagaaattc ggacaagctt attgctcgta aaaaagactg ggatccaaaa aaatatggtg   3900
gttttgatag tccaacggta gcttattcag tcctagtggt tgctaaggtg gaaaaaggga   3960
aatcgaagaa gttaaaatcc gttaaagagt tactagggat cacaattatg gaaagaagtt   4020
```

```
cctttgaaaa aaatccgatt gactttttag aagctaaagg atataaggaa gttaaaaaag   4080

acttaatcat taaactacct aaatatagtc tttttgagtt agaaaacggt cgtaaacgga   4140

tgctggctag tgccggagaa ttacaaaaag gaaatgagct ggctctgcca agcaaatatg   4200

tgaatttttt atatttagct agtcattatg aaaagttgaa gggtagtcca gaagataacg   4260

aacaaaaaca attgtttgtg gagcagcata agcattattt agatgagatt attgagcaaa   4320

tcagtgaatt ttctaagcgt gttattttag cagatgccaa tttagataaa gttcttagtg   4380

catataacaa acatagagac aaaccaatac gtgaacaagc agaaaatatt attcatttat   4440

ttacgttgac gaatcttgga gctcccgctg cttttaaata ttttgataca acaattgatc   4500

gtaaacgata tacgtctaca aaagaagttt tagatgccac tcttatccat caatccatca   4560

ctggtcttta tgaaacacgc attgatttga gtcagctagg aggtgactga ctcgagctag   4620

aggcatcaaa taaaacgaaa ggctcagtcg aaagactggg cctttcgttt tatctgttgt   4680

ttgtcggtga acgctctcct gagtaggaca aatccgccgc cctagaccta gcaccctgca   4740

gaactatatg attttccgca gtatatttta gatgaagatt atttcttaat aactaaaaat   4800

atggtataat actcttaata aatgcagtaa tacaggggct tttcaagact gaagtctagc   4860

tgagacaaat agtgcgatta cgaaattttt tagacaaaaa tagtctacga ggttttagag   4920

ctatgctgtt ttgaatggtc ccaaaacnnn nnnnnnnnnn nnnnnnnnnn nnnnnnngtt   4980

ttagagctat gctgttttga atggtcccaa aacttcagca cactgagact tgttgagttc   5040

catgttttag agctatgctg ttttgaatgg tctccattct ctagatgatg attaaggatc   5100

tattttttg ggcggggccg cccaaaaaaa t                                  5131
```

<210> SEQ ID NO 2
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 2

```
taatgggcac aaattttctg tcagtggaga                                     30
```

<210> SEQ ID NO 3
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 3

```
gggcagtcgc ttccaacggt ttgatcgtca                                     30
```

<210> SEQ ID NO 4
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 4

```
gcaaattaaa ctaagcgaaa gccagctgtc                                     30
```

<210> SEQ ID NO 5
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 5
ataccatccc catggtgact cggcggtct 29

<210> SEQ ID NO 6
<211> LENGTH: 4554
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (4401)..(4420)
<223> OTHER INFORMATION: n is a, c, g, or t

<400> SEQUENCE: 6
tccctatcag tgatagagat tgacatccct atcagtgata gagatactga gcacatcagc 60
aggacgcact gaccgaattc attaaagagg agaaaggtgc ggccgcatgc atcaccatca 120
ccatcacatg gataagaaat actcaatagg cttagatatc ggcacaaata gcgtcggatg 180
ggcggtgatc actgatgaat ataaggttcc gtctaaaaag ttcaaggttc tgggaaatac 240
agaccgccac agtatcaaaa aaaatcttat aggggctctt ttatttgaca gtggagagac 300
agcggaagcg actcgtctca aacggacagc tcgtagaagg tatacacgtc ggaagaatcg 360
tatttgttat ctacaggaga tttttcaaa tgagatggcg aaagtagatg atagtttctt 420
tcatcgactt gaagagtctt ttttggtgga agaagacaag aagcatgaac gtcatcctat 480
ttttggaaat atagtagatg aagttgctta tcatgagaaa tatccaacta tctatcatct 540
gcgaaaaaaa ttggtagatt ctactgataa agcggatttg cgcttaatct atttggcctt 600
agcgcatatg attaagtttc gtggtcattt tttgattgag ggagatttaa atcctgataa 660
tagtgatgtg gacaaactat ttatccagtt ggtacaaacc tacaatcaat tatttgaaga 720
aaaccctatt aacgcaagtg gagtagatgc taaagcgatt ctttctgcac gattgagtaa 780
atcaagacga ttagaaaatc tcattgctca gctccccggt gagaagaaaa atggcttatt 840
tgggaatctc attgctttgt cattgggttt gacccctaat tttaaatcaa attttgattt 900
ggcagaagat gctaaattac agctttcaaa agatacttac gatgatgatt tagataattt 960
attggcgcaa attggagatc aatatgctga tttgtttttg gcagctaaga atttatcaga 1020
tgctatttta ctttcagata tcctaagagt aaatactgaa ataactaagg ctcccctatc 1080
agcttcaatg attaaacgct acgatgaaca tcatcaagac ttgactcttt taaaagcttt 1140
agttcgacaa caacttccag aaaagtataa agaaatcttt tttgatcaat caaaaaacgg 1200
atatgcaggt tatattgatg gggagctag ccaagaagaa ttttataaat ttatcaaacc 1260
aattttagaa aaaatggatg gtactgagga attattggtg aaactaaatc gtgaagattt 1320
gctgcgcaag caacggacct ttgacaacgg ctctattccc catcaaattc acttgggtga 1380
gctgcatgct attttgagaa gacaagaaga cttttatcca tttttaaaag acaatcgtga 1440
gaagattgaa aaaatcttga cttttcgaat tccttattat gttggtccat tggcgcgtgg 1500
caatagtcgt tttgcatgga tgactcggaa gtctgaagaa acaattaccc catggaattt 1560
tgaagaagtt gtcgataaag gtgcttcagc tcaatcattt attgaacgca tgacaaactt 1620
tgataaaaat cttccaaatg aaaaagtact accaaaacat agtttgcttt atgagtattt 1680
tacggtttat aacgaattga caaaggtcaa atatgttact gaaggaatgc gaaaaccagc 1740

```
atttctttca ggtgaacaga agaaagccat tgttgattta ctcttcaaaa caaatcgaaa   1800
agtaaccgtt aagcaattaa aagaagatta tttcaaaaaa atagaatgtt ttgatagtgt   1860
tgaaatttca ggagttgaag atagatttaa tgcttcatta ggtacctacc atgatttgct   1920
aaaaattatt aaagataaag atttttttgga taatgaagaa aatgaagata tcttagagga   1980
tattgtttta acattgacct tatttgaaga tagggagatg attgaggaaa gacttaaaac   2040
atatgctcac ctctttgatg ataaggtgat gaaacagctt aaacgtcgcc gttatactgg   2100
ttggggacgt ttgtctcgaa aattgattaa tggtattagg gataagcaat ctggcaaaac   2160
aatattagat tttttgaaat cagatggttt tgccaatcgc aattttatgc agctgatcca   2220
tgatgatagt ttgacattta aagaagacat tcaaaaagca caagtgtctg gacaaggcga   2280
tagtttacat gaacatattg caaatttagc tggtagccct gctattaaaa aaggtatttt   2340
acagactgta aaagttgttg atgaattggt caaagtaatg gggcggcata agccagaaaa   2400
tatcgttatt gaaatggcac gtgaaaatca gacaactcaa aagggccaga aaaattcgcg   2460
agagcgtatg aaacgaatcg aagaaggtat caaagaatta ggaagtcaga ttcttaaaga   2520
gcatcctgtt gaaaatactc aattgcaaaa tgaaaagctc tatctctatt atctccaaaa   2580
tggaagagac atgtatgtgg accaagaatt agatattaat cgtttaagtg attatgatgt   2640
cgatcacatt gttccacaaa gtttccttaa agacgattca atagacaata aggtcttaac   2700
gcgttctgat aaaaatcgtg gtaaatcgga taacgttcca agtgaagaag tagtcaaaaa   2760
gatgaaaaac tattggagac aacttctaaa cgccaagtta atcactcaac gtaagtttga   2820
taatttaacg aaagctgaac gtggaggttt gagtgaactt gataaagctg gttttatcaa   2880
acgccaattg gttgaaactc gccaaatcac taagcatgtg gcacaaattt tggatagtcg   2940
catgaatact aaatacgatg aaaatgataa acttattcga gaggttaaag tgattacctt   3000
aaaatctaaa ttagtttctg acttccgaaa agatttccaa ttctataaag tacgtgagat   3060
taacaattac catcatgccc atgatgcgta tctaaatgcc gtcgttggaa ctgctttgat   3120
taagaaatat ccaaaacttg aatcggagtt tgtctatggt gattataaag tttatgatgt   3180
tcgtaaaatg attgctaagt ctgagcaaga aataggcaaa gcaaccgcaa aatatttctt   3240
ttactctaat atcatgaact tcttcaaaac agaaattaca cttgcaaatg gagagattcg   3300
caaacgccct ctaatcgaaa ctaatgggga aactggagaa attgtctggg ataaagggcg   3360
agattttgcc acagtgcgca aagtattgtc catgccccaa gtcaatattg tcaagaaaac   3420
agaagtacag acaggcggat tctccaagga gtcaatttta ccaaaaagaa attcggacaa   3480
gcttattgct cgtaaaaaag actgggatcc aaaaaaatat ggtggttttg atagtccaac   3540
ggtagcttat tcagtcctag tggttgctaa ggtggaaaaa gggaaatcga agaagttaaa   3600
atccgttaaa gagttactag ggatcacaat tatggaaaga agttcctttg aaaaaaatcc   3660
gattgacttt ttagaagcta aaggatataa ggaagttaaa aaagacttaa tcattaaact   3720
acctaaatat agtctttttg agttagaaaa cggtcgtaaa cggatgctgg ctagtgccgg   3780
agaattacaa aaaggaaatg agctggctct gccaagcaaa tatgtgaatt ttttatattt   3840
agctagtcat tatgaaaagt tgaagggtag tccagaagat aacgaacaaa aacaattgtt   3900
tgtggagcag cataagcatt atttagatga gattattgag caaatcagtg aattttctaa   3960
gcgtgttatt ttagcagatg ccaatttaga taaagttctt agtgcatata acaaacatag   4020
agacaaacca atacgtgaac aagcagaaaa tattattcat ttatttacgt tgacgaatct   4080
tggagctccc gctgctttta aatattttga tacaacaatt gatcgtaaac gatatacgtc   4140
```

```
tacaaaagaa gttttagatg ccactcttat ccatcaatcc atcactggtc tttatgaaac   4200

acgcattgat ttgagtcagc taggaggtga ctgactcgag ctagaggcat caaataaaac   4260

gaaaggctca gtcgaaagac tgggcctttc gttttatctg ttgtttgtcg gtgaacgctc   4320

tcctgagtag gacaaatccg ccgccctaga cctagcaccc tgcagttgac agctagctca   4380

gtcctaggta taatgctagc nnnnnnnnnn nnnnnnnnnn gttttagagc tagaaatagc   4440

aagttaaaat aaggctagtc cgttatcaac ttgaaaaagt ggcaccgagt cggtgctttt   4500

tttctagatg atgattaagg atctattttt ttgggcgggg ccgcccaaaa aaat         4554


<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 7

aaattttctg tcagtggaga                                                 20


<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 8

ttccaacggt ttgatcgtca                                                 20


<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 9

ctaagcgaaa gccagctgtc                                                 20


<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10

catggtgact cggcggtcta                                                 20


<210> SEQ ID NO 11
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 11

atgcgttatt ttcgcctgtg ta                                              22


<210> SEQ ID NO 12
<211> LENGTH: 19
<212> TYPE: DNA
```

<213> ORGANISM: Artificial Sequence
<220> FEATURE:
<223> OTHER INFORMATION: Synthetic Polynucleotide

<400> SEQUENCE: 12
ttagcgttgc cagtgctcg 19

<210> SEQ ID NO 13
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 13
catgcgctcg aggctcagct tgttgattat catatg 36

<210> SEQ ID NO 14
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 14
cataaggagc tctcagcgca gcttgtcggc ca 32

<210> SEQ ID NO 15
<211> LENGTH: 89
<212> TYPE: DNA
<213> ORGANISM: Artificial Sequence
<220> FEATURE:
<223> OTHER INFORMATION: Synthetic Polynucleotide

<400> SEQUENCE: 15
cactgaccga attcattaaa gaggagaaag gtgcggccgc atgcatcacc atcaccatca 60
catggataag aaatactcaa taggcttag 89

<210> SEQ ID NO 16
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 16
ttcgactgag cctttcgttt tatttgatgc ctctagtcag tcacctccta gctgactcaa 60

<210> SEQ ID NO 17
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 17
tatgctgttt tgaatggtct ccattctcta gaggcatcaa ataaaacgaa aggctcagt 59

<210> SEQ ID NO 18
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 18
aaccaaaaaa acaagcgctt tcaaaacgcg tcgacagggt gaagacgaaa gggcctcgtg 60

<210> SEQ ID NO 19
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 19
ctataaaaat aggcgtatca cgaggccc 28

<210> SEQ ID NO 20
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 20
ttgagtattt cttatccatg tgatggtgat gg 32

<210> SEQ ID NO 21
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 21
gagcatgaag accattcagc acactgagac ttgttgagtt c 41

<210> SEQ ID NO 22
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 22
gagcatgaag acccctcgct cgtagactat ttttgtctaa aaaatttcgt 50

<210> SEQ ID NO 23
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 23
gctatcggca caaatagcgt cggatg 26

<210> SEQ ID NO 24
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 24
taagcctatt gagtatttct tatccatcga gg 32

<210> SEQ ID NO 25
<211> LENGTH: 30
<212> TYPE: DNA

<213> ORGANISM: Artificial Sequence
<220> FEATURE:
<223> OTHER INFORMATION: Synthetic Polynucleotide

<400> SEQUENCE: 25
gatagatagt tggatatttc tcatgataag 30

<210> SEQ ID NO 26
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 26
ctgaaataac taaggctccc ctatc 25

<210> SEQ ID NO 27
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 27
gatagggaga tgattgagga aagac 25

<210> SEQ ID NO 28
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 28
cgcatgaata ctaaatacga tgaaaatg 28

<210> SEQ ID NO 29
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 29
catgatgcta gcaccctgca gagcttctag atgatgatta aggatctatt tttttgggcg 60

<210> SEQ ID NO 30
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 30
gtgcatataa caaacataga gac 23

<210> SEQ ID NO 31
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 31
cctcgtgata cgcctatttt tataggttaa tg 32

<210> SEQ ID NO 32
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 32
caccactcat tgccacattc cttgtg 26

<210> SEQ ID NO 33
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 33
cggcttcaaa tttagcgatc tcttc 25

<210> SEQ ID NO 34
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 34
atcgatatcg attccctatc agtgatagag attgac 36

<210> SEQ ID NO 35
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 35
catgatatcg atagggtgaa gacgaaaggg cctcg 35

<210> SEQ ID NO 36
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 36
gatggaattg cccaatatta tgcaccc 27

<210> SEQ ID NO 37
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 37
cactcatcgc agtcggccta ttgg 24

<210> SEQ ID NO 38
<211> LENGTH: 39
<212> TYPE: DNA
<213> ORGANISM: Artificial Sequence
<220> FEATURE:

<223> OTHER INFORMATION: Synthetic Polynucleotide

<400> SEQUENCE: 38
catgatcccg ggggacagca agcgaaccat ttttttggg 39

<210> SEQ ID NO 39
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 39
catgatggta ccatgcatac cactcgactg aagaaggttg 40

<210> SEQ ID NO 40
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 40
catgatggat cctcagattt cctcctgacc agccg 35

<210> SEQ ID NO 41
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 41
catgatcccg gggacagacg tcatactaga tatcaagcga c 41

<210> SEQ ID NO 42
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 42
catgatacta gtggagcaga agagcataca tctggaag 38

<210> SEQ ID NO 43
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 43
acgtctcatt ttcgccagat 20

<210> SEQ ID NO 44
<211> LENGTH: 80
<212> TYPE: DNA
<213> ORGANISM: Artificial Sequence
<220> FEATURE:
<223> OTHER INFORMATION: Synthetic Polynucleotide

<400> SEQUENCE: 44
ggctttacac tttatgcttc cggctcgtat gttgtgtgga attgtgagcg gataacaatt 60
cttttgcttt gccacggaac 80

<210> SEQ ID NO 45
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 45
ttaaactgac gattcaactt tataatcttt gaaataatag tgcttatccc ggtcgtttat 60
ctacgagccg gataacgc 78

<210> SEQ ID NO 46
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 46
ggctttacac tttatgcttc cggctcgtat gttgtgtgga attgtgagcg gataacaatt 60
gctcagcttg ttgattatca tatg 84

<210> SEQ ID NO 47
<211> LENGTH: 80
<212> TYPE: DNA
<213> ORGANISM: Artificial Sequence
<220> FEATURE:
<223> OTHER INFORMATION: Synthetic Polynucleotide

<400> SEQUENCE: 47
ttaaactgac gattcaactt tataatcttt gaaataatag tgcttatccc ggtcgtttat 60
tcagcgcagc ttgtcggcca 80

<210> SEQ ID NO 48
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 48
catgatcccg gggttttatg gacagcaagc gaacc 35

<210> SEQ ID NO 49
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 49
catgatccta ggcgtctaag aaaccattat tatcatgaca ttaacc 46

<210> SEQ ID NO 50
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 50
catgatcccg ggcagaagat cctgcagggc cttc 34

<210> SEQ ID NO 51
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 51
catgatccta ggaaattgta aacgttaata ttttgttaaa attcgc 46

<210> SEQ ID NO 52
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 52
catgagggtc tcacgaggtt ttagagctat gctgttttga atggtcccaa aac 53

<210> SEQ ID NO 53
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 53
catgagggtc tcctgaagtt ttgggaccat tcaaaacagc atagctctaa aac 53

<210> SEQ ID NO 54
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 54
gggcagtcgc ttccaacggt ttga 24

<210> SEQ ID NO 55
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 55
tgacgatcaa accgttggaa gcga 24

<210> SEQ ID NO 56
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 56
tcgtcagttt tagagctatg ctgttttgaa tggtcccaaa ac 42

<210> SEQ ID NO 57
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 57
atttgcgttt tgggaccatt caaaacagca tagctctaaa ac 42

<210> SEQ ID NO 58
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 58
gcaaattaaa ctaagcgaaa gcca 24

<210> SEQ ID NO 59
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 59
gacagctggc tttcgcttag ttta 24

<210> SEQ ID NO 60
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 60
gctgtcgttt tagagctatg ctgttttgaa tggtcccaaa acttcaggag accctcatg 59

<210> SEQ ID NO 61
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 61
ctgcccgttt tgggaccatt caaaacagca tagctctaaa acctcgtgag accctcatg 59

<210> SEQ ID NO 62
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 62
tggtatgttt tgggaccatt caaaacagca tagctctaaa acctcgtgag accctcatg 59

<210> SEQ ID NO 63
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 63
ataccatccc catggtgact cggc 24

<210> SEQ ID NO 64

<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 64
tagaccgccg agtcaccatg ggga 24

<210> SEQ ID NO 65
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 65
ggtctagttt tagagctatg ctgttttgaa tggtcccaaa acttcaggag accctcatg 59

<210> SEQ ID NO 66
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 66
atttgcgttt tgggaccatt caaaacagca tagctctaaa acctcgtgag accctcatg 59

<210> SEQ ID NO 67
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 67
ttccaacggt ttgatcgtca gtttta 26

<210> SEQ ID NO 68
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 68
tgacgatcaa accgttggaa gctagc 26

<210> SEQ ID NO 69
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 69
ctaagcgaaa gccagctgtc gtttta 26

<210> SEQ ID NO 70
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 70

-continued

```
gacagctggc tttcgcttag gctagc                                          26


<210> SEQ ID NO 71
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 71

gagtcagttt tgggaccatt caaaacagca tagctctaaa acctcgtgag accctcatg      59


<210> SEQ ID NO 72
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 72

tgactcccgc tttacggcaa attt                                            24


<210> SEQ ID NO 73
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 73

gcacctaaat ttgccgtaaa gcgg                                            24


<210> SEQ ID NO 74
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 74

aggtgcgttt tagagctatg ctgttttgaa tggtcccaaa acttcaggag accctcatg      59
```

TUNING MICROBIAL POPULATIONS WITH PROGRAMMABLE NUCLEASES

RELATED APPLICATIONS

This application claims the benefit under 35 U.S.C. § 119(e) of U.S. provisional application No. 61/873,894, filed Sep. 5, 2013, and U.S. provisional application No. 62/010,976, filed Jun. 11, 2014, each of which is incorporated by reference herein in its entirety.

FEDERALLY SPONSORED RESEARCH

This invention was made with Government support under Grant No. OD008435 awarded by the National Institutes of Health and under Contract No. HDTRA1-14-1-0007 awarded by the Defense Threat Reduction Agency. The Government has certain rights in the invention.

BACKGROUND OF THE INVENTION

Current antimicrobial paradigms, such as antibiotics, broadly target microbial processes and cannot be specifically targeted against virulence factors or antibiotic-resistance genes, resulting in selection and dissemination of resistance among virulent and non-virulent organisms. Thus, this paradigm is always playing catch-up, as microbial consortia constantly trade and evolve traits to resist sporadic broad-spectrum treatments. As antibiotic resistance continues to spread and multidrug resistant strains continue to emerge, the production of novel antibiotic compounds remains behind.

Recent efforts to compensate for the lag in antibiotic production are directed to synthetic bacterial systems that rely on signal detection of pathogens and respond by producing antimicrobial agents (e.g., quorum-signaling molecules or pyocins). These current synthetic systems cannot directly target existing and emerging virulence factors or antibiotic resistance genes and, thus, are not useful for combating, for example, recombinant biothreat genes (e.g., genes that, when expressed, may be harmful), which may be engineered to be expressed by otherwise innocuous organisms such as probiotic strains of bacteria.

SUMMARY OF THE INVENTION

Various aspects and embodiments of the present disclosure relate to the discovery that engineered autonomously distributed circuits containing programmable nucleases (i.e., "programmable nuclease circuits") can be delivered to microbial organisms in vivo to, for example, mediate sequence-specific elimination of microbial organisms that contain a target gene of interest (e.g., a gene that is harmful to humans). Some embodiments of the present disclosure relate to engineered variants of the Type II CRISPR-Cas (Clustered Regularly Interspaced Short Palindromic Repeats-CRISPR-associated) system of *Streptococcus pyogenes*, which can be used in accordance with the present disclosure to reverse antibiotic resistance in, or specifically destroy, a wide range of microbial organisms. Other programmable nucleases that can be used in accordance with the present disclosure include other CRISPR-Cas systems, engineered TALEN (Transcription Activator-Like Effector Nuclease) variants and engineered zinc finger nuclease (ZFN) variants. Thus, the methods and engineered autonomously distributed circuits provided herein, in some embodiments, may be used to weaken resistance of microbial pathogens to existing antibiotics.

These programmable nuclease circuits may be delivered to microbial organisms using a variety of delivery methods. For example, in some embodiments, programmable nuclease circuits may be delivered to microbial organisms using recombinant bacteriophage and/or phagemids (also referred to as phagemid particles), which may specifically target select microbial cell populations in vivo without infecting, for example, neighboring cells (e.g., non-microbial cells). In other embodiments, broad-host-range bacteriophage and/or phagemid particles may be used to deliver programmable nuclease circuits to microbial organisms, whereby specificity of activity is conferred within the design of the nuclease circuits. In yet other embodiments, programmable nuclease circuits may be delivered to microbial organisms via conjugation using probiotic bacteria, wherein the vectors may be mobilizable such that they can be delivered from a donor to a recipient cell or self-transmissible such that they broadly propagate through a population. It should also be appreciated that programmable nuclease circuits may be delivered to microbial organisms using chemical-based delivery vehicles (e.g., cyclodextrin, calcium phosphate, cationic polymers, cationic liposomes) or nanoparticle-based delivery vehicles (or platforms). In still other embodiments, a combination approach may be taken for delivery, such as, but not limited to, using bacteriophage or nanoparticles to deliver self-transmissible plasmids to a recipient population. Other delivery vehicles/platforms are contemplated herein, including, without limitation, non-chemical-based delivery vehicles (e.g., electroporation, sonoporation, optical transfection), particle-based delivery vehicles (e.g., gene gun, magnetofection, impalefection, particle bombardment), and viral-based delivery vehicles (e.g., use of viruses as carriers). The choice of delivery vehicle/platform will depend, in part, on the type of cell to which the programmable nuclease circuits are delivered as well as the environment of the cells (e.g., in vivo v. in vitro).

Provided herein, in some aspects, is a transformative platform for targeted biothreat (e.g., antibiotic resistance) neutralization with engineered autonomously distributed circuits, or programmable nuclease circuits. The programmable nuclease circuits of the present disclosure enable, in some embodiments, sequence-specific destruction of any gene or nucleotide sequence of interest, including biothreat-causing virulence genes and antibiotic-resistance genes. The circuits can be engineered to specifically attenuate undesirable genes and/or to kill the target host pathogen. In other embodiments, the targeted gene or nucleotide sequence may be used to identify and/or eliminate a particular strain or broader grouping of bacteria (e.g., housekeeping genes, 16S rDNA, and other conserved DNA sequences). This platform can be efficiently and rapidly encoded into synthetic constructs for broad delivery and dissemination in microbial populations via the same mechanisms leveraged by biothreat pathways (e.g., conjugation and bacteriophages) and novel carriers (e.g., artificial gene delivery agents). Thus, the present disclosure is a paradigm shift in combating pathogens because it enables, inter alia, autonomous and distributed neutralization of biothreats at the gene level.

Various aspects of the present disclosure provide methods that comprise delivering to microbial cells (e.g., bacterial cells) in vivo a delivery vehicle with at least one nucleic acid encoding an engineered autonomously distributed circuit, which contains a programmable nuclease that targets a gene or nucleotide sequence of interest. In some embodiments, a nucleic acid encoding an engineered autonomously distributed circuit is stably expressed, while in other embodiments, a nucleic acid encoding an engineered autonomously distributed circuit is transiently expressed. In some embodiments, expression of a nucleic acid encoding an engineered autonomously distributed circuit is inducible.

Some aspects of the present disclosure provide phagemids that comprise an engineered autonomously distributed circuit, which contains at least one nucleic acid encoding a programmable nuclease that targets a gene or nucleotide sequence of interest.

Other aspects of the present disclosure provide bacteriophages that comprise an engineered autonomously distributed circuit, which contains at least one nucleic acid encoding a programmable nuclease that targets a gene or nucleotide sequence of interest.

Also provided in various aspects of the present disclosure are donor bacterial cells (e.g., probiotic bacterial cells and/or commensal bacterial cells) that comprise an engineered autonomously distributed circuit, which contains at least one nucleic acid encoding a programmable nuclease that targets a gene or nucleotide sequence of interest.

Additional aspects of the present disclosure provide nucleic acids encoding an engineered autonomously distributed circuit, which contains a programmable nuclease that targets a virulence factor or an antibiotic resistance gene. Also provided herein are phagemids and bacteriophages that comprise nucleic acids encoding engineered autonomously distributed circuits.

Yet other aspects of the present disclosure provide libraries that comprise a plurality of nucleic acids, each encoding an engineered autonomously distributed circuit, which contains a programmable nuclease that targets a virulence factor or an antibiotic resistance gene.

Various aspects of the present disclosure also provide methods that comprise culturing the microbial cells (e.g., bacterial cells) from a sample, delivering to the cultured microbial cells a delivery vehicle with at least one nucleic acid encoding an engineered autonomously distributed circuit, which contains a programmable nuclease that targets a gene or nucleotide sequence of interest, and determining whether or not the microbial cells that contain the programmable nuclease survive, wherein death of the microbial cells indicates that the sample comprises microbial cells with the gene of interest. In some embodiments, the sample is of a subject (e.g., a patient such as a human patient). In some embodiments, the sample is biological fluid sample (e.g., urine, blood (plasma or serum), mucosa), a tissue sample or a cell sample.

In some embodiments, the methods further comprise diagnosing the subject (e.g., a human). In some embodiments, the methods further comprise treating the subject (e.g., a human).

In some embodiments, the programmable nucleases provided herein are RNA-guided nucleases. Thus, in some embodiments, the engineered autonomously distributed circuits provided herein contain a Cas9 nuclease, a guide RNA (gRNA), and/or a transactivating small RNA (tracrRNA), with some or all regions derived from a CRISPR-Cas system (e.g., Type II CRISPR-Cas system of *Streptococcus pyogenes*). In some embodiments, the gRNA and the tracrRNA are each encoded separately (either on the same nucleic acid or different nucleic acids) to produce separate molecules. In some embodiments, the gRNA and the tracrRNA are encoded by a single nucleic acid to produce a chimeric (e.g., hybrid) single-guide RNA molecule (Jinek, M., et al. *Science* 337, 816-821 (2012)).

In other embodiments, the programmable nucleases are transcriptional activator like (TAL)-effector nucleases (TALENs).

In yet other embodiments, the programmable nucleases are zinc finger nucleases (ZFNs).

In some embodiments, the microbial cells are Gram-negative bacterial cells, Gram-positive bacterial cells, or a combination thereof.

In some embodiments, the microbial cells are pathogenic bacterial cells. For example, the pathogenic microbial cells may be extended-spectrum beta-lactamase-producing (ESBL) *Escherichia coli*, ESBL *Klebsiella pneumonia, Pseudomonas aeruginosa*, vancomycin-resistant *Enterococcus* (VRE), methicillin-resistant *Staphylococcus aureus* (MRSA), multidrug-resistant (MDR) *Acinetobacter baumannii*, MDR *Enterobacter* spp. bacterial cells or a combination thereof. Non-ESBL microbial cells are also contemplated herein. In some embodiments, the microbial cells are non-pathogenic bacterial cells (e.g., probiotic and/or commensal bacterial cells). In some embodiments, the microbial cells form microbial flora (e.g., natural human microbial flora). Thus, the present disclosure contemplates microbial cells that are members of the phyla *Actinobacteria, Bacteroidetes, Proteobacteria, Firmicutes*, or others, or a combination thereof. In some embodiments, the microbial cells are used in industrial or environmental bioprocesses (e.g., bioremediation).

In some embodiments, the gene of interest is located episomally, while in other embodiments, the gene of interest is located chromosomally. In yet other embodiments, the gene of interest is located extracellularly (e.g., in the environment, in a neighboring cell, or in a bacteriophage) and is targeted upon receipt via horizontal gene transfer.

In some embodiments, the gene of interest is a virulence factor gene or a toxin gene. In other embodiments, the gene of interest is an antibiotic resistance gene. In yet other embodiments, the gene of interest is a remodeling gene. In still other embodiments, the gene of interest is a modulatory gene.

In some embodiments, the delivery vehicles are bacteriophages or engineered particles derived from bacteriophages. For example, in some embodiments, the delivery vehicles are phagemids.

In other embodiments, the delivery vehicles are probiotic bacterial cells comprising a conjugative plasmid.

In some embodiments, the programmable nucleases are operably linked to an inducible promoter.

Also provided herein are methods that comprise delivering to microbial cells in vivo (a) a delivery vehicle with at least one nucleic acid encoding an engineered autonomously distributed circuit that contains a programmable nuclease that targets a gene or nucleotide sequence of interest, and (b) a nucleic acid encoding an SOS-responsive reporter construct.

BRIEF DESCRIPTION OF THE DRAWINGS

The accompanying drawings are not intended to be drawn to scale. In the drawings, each identical or nearly identical component illustrated in various figures is represented by a like numeral. For purposes of clarity, not every component may be labeled in every drawing.

DETAILED DESCRIPTION OF THE INVENTION

Figure 1:
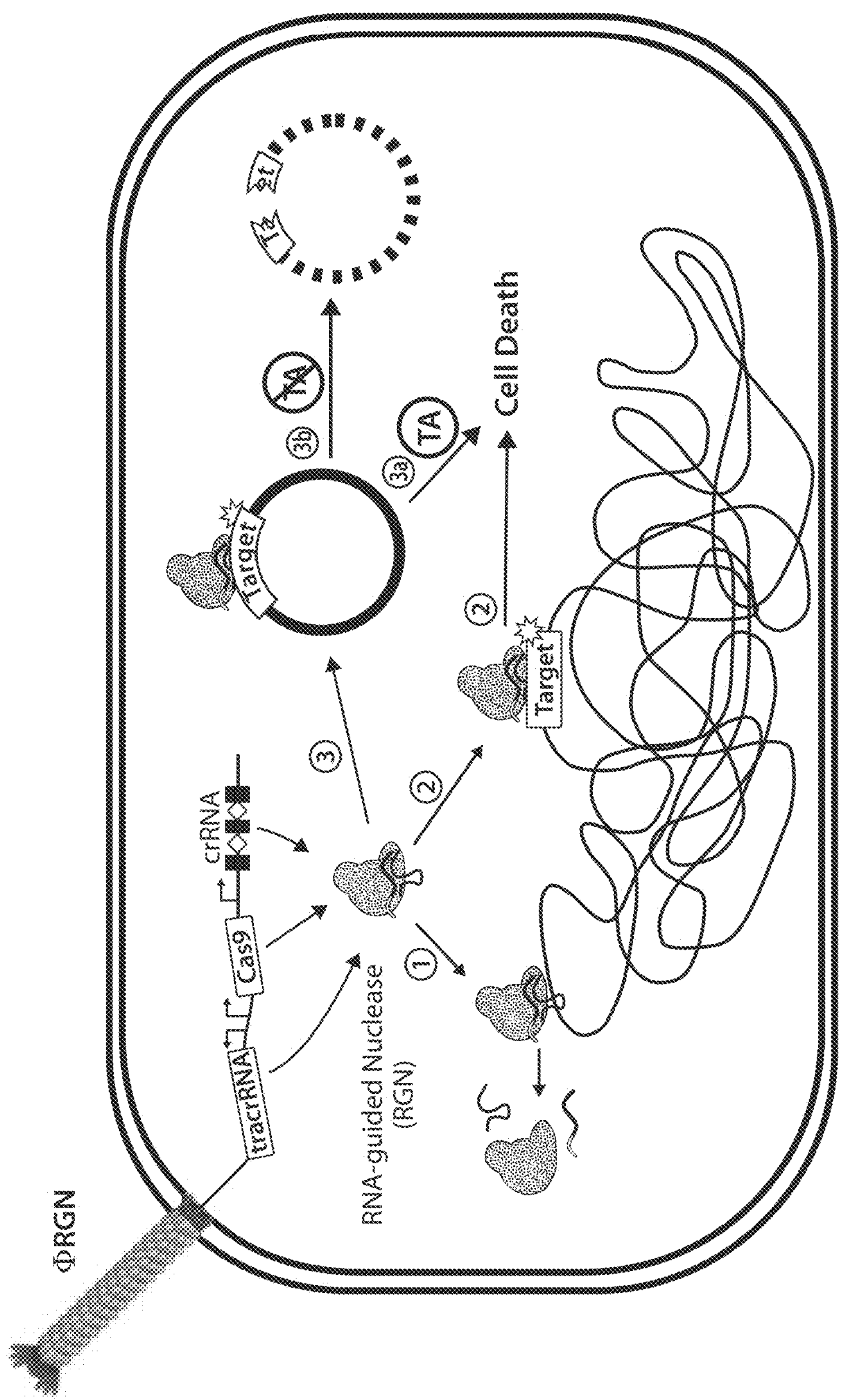
FIG. 1 shows a schematic of an example of how bacteriophage-delivered RGN constructs differentially affect host cell physiology in a sequence-dependent manner. If the target sequence is: (1) absent, the RGN exerts no effect; (2) chromosomal, RGN activity is cytotoxic; (3) episomal, the RGN leads to either (3a) cell death or (3b) plasmid loss, depending on the presence or absence of toxin-antitoxin (TA) systems, respectively.

Antimicrobial resistance is a major global problem exacerbated by global travel, antibiotic overuse, horizontal gene transfer, bacterial evolution and a dearth of new antimicrobial agents (Boucher, H. W., et al. *Clinical Infectious Diseases* 48, 1-12 (2009)). Troublesome pathogens include vancomycin-resistant enterococci (VRE), methicillin-resistant *Staphylococcus aureus* (MRSA), extended-spectrum beta-lactamase-producing (ESBL) *Escherichia coli* and *Klebsiella pneumoniae*, and multidrug-resistant (MDR) *Acinetobacter baumannii, Pseudomonas aeruginosa* and *Enterobacter* spp. New classes of antimicrobials are needed, but few are being developed (Walsh, C. *Nat Rev Microbiol* 1, 65-70 (2003)). The antimicrobial pipeline is especially dry for MDR Gram-negative bacteria (Boucherm, H. W., et al. (2009)), resulting in sicker patients, longer hospitalizations, increased morbidity and mortality, and high economic costs (Hall-Stoodley, L., et al. *Nat Rev Microbiol* 2, 95-108 (2004); Wise, R. J. *Antimicrob Chemother.* 54, 306-310 (2004); Hall, B. G. *Nat Rev Microbiol* 2, 430-435 (2004)). Thus, there is a large unmet need for new therapeutic agents to treat MDR bacterial infections.

In addition to natural evolutionary processes, exponential improvements in DNA synthesis technologies enable the accelerated capability to engineer new pathogens or revive old pathogens. A fundamental challenge of detecting and neutralizing engineered biothreats is that they are linked to underlying genes (e.g., toxin genes, virulence genes and antibiotic-resistance genes), which can be readily mobilized into new cellular backgrounds.

Engineered autonomously distributed circuits containing programmable nucleases (i.e., "programmable nuclease circuits") provide a platform for protecting against, inter alia, toxin genes, virulence genes and antibiotic-resistance genes.

Programmable RNA-Guided Nucleases—CRISPR-Cas System

In some embodiments, the programmable nuclease circuits of the invention use components of the clustered, regularly interspaced, short palindromic repeats (CRISPR)-CRISPR-associated (Cas) system to selectively cleave DNA encoding a gene of interest such as, for example, a toxin gene, a virulence factor gene, an antibiotic resistance gene, a remodeling gene or a modulatory gene. In some embodiments, the programmable nuclease circuits of the present disclosure use components of the Type II CRISPR-Cas system to selectively cleave DNA encoding a gene of interest such as, for example, a toxin gene, a virulence factor gene, an antibiotic resistance gene, a remodeling gene or a modulatory gene. CRISPR-Cas systems are used by various bacteria and archaea to mediate defense against viruses and other foreign nucleic acid. Short segments of foreign DNA, called spacers, are incorporated into the genome between CRISPR repeats and serve as a 'memory' of past exposures. CRISPR spacers are then used to recognize and silence exogenous genetic elements in a manner analogous to RNAi in eukaryotic organisms. Recent work has shown that Type II CRISPR-Cas systems can be engineered to direct targeted double-stranded DNA breaks in vitro to specific sequences. Programmable RNA-guided nucleases (RGNs) consist of two components: a short ~100 nucleotide single guide RNA (gRNA), containing 20 variable nucleotides at the 5' end involved in base pairing with a target DNA sequence, and the Cas9 nuclease, which cleaves the target DNA (Jinek, M., et al. *Science* 337, 816-821 (2012)).

The CRISPR-Cas system of *Streptococcus pyogenes* enables effective, programmable RGNs for genome editing in human, zebrafish, and microbes (Mali, P., et al. *Science* 339, 823-826 (2013); Jinek, M., et al. *Science* 337, 816-821 (2012); Jiang, W., et al. *Nat Biotechnol* 31, 233-239 (2013); Hwang, W. Y., et al. *Nat Biotechnol* 31, 227-229 (2013); Deltcheva, E., et al. *Nature* 471, 602-607 (2011); Cong, L., et al. *Science* 339, 819-823 (2013); Cho, S. W., et al. *Nat Biotechnol* 31, 230-232 (2013); Bikard, D., et al. *Cell Host & Microbe* 12, 177-186 (2012)). The specificity of CRISPR-Cas is dictated by the identity of spacer sequences flanked by direct repeats encoded in the CRISPR locus, which are transcribed and processed into mature guide RNAs (gRNA) (Jinek, M. et al. (2012)). With the aid of a trans-activating small RNA (tracrRNA), gRNAs license the Cas9 endonuclease to introduce double-stranded breaks in target DNA sequences (protospacers) (Jinek, M. et al. (2012); Bikard, D., et al. (2012)). Thus, through simple modifications of spacers in the CRISPR loci, an RGN can direct cleavage of almost any DNA sequence with the only design restriction being a NGG motif immediately 3' of the protospacer (Jinek, M. et al. (2012)). Natural CRISPR loci have been discovered with up to 58 spacers to simultaneously license Cas9 to induce double stranded breaks at 58 different DNA sequences (Gunderson, F. F., et al. *mBio* 4(2013)). Thus, a single programmable nuclease circuit may be engineered to target at least 58 different DNA sequences, as described elsewhere herein.

In some embodiments of the present disclosure, the engineered autonomously distributed circuits of the present disclosure contain components of the CRISPR-Cas system, including a Cas9 nuclease, a guide RNA (gRNA) (also referred to herein as CRISPR RNA (crRNA)), and a trans-activating small RNA (tracrRNA) (e.g., dual-guide system). In some embodiments, this system is employed using a Cas9 nuclease and a chimeric single-guide RNA (sgRNA) that combines the crRNA and tracrRNA into a single transcript (referred to herein as a "single-guide system") (Jinek, M., et al. *Science* 337, 816-821 (2012)).

Programmable TAL Effector Nucleases—TAL/TALEN System

In some embodiments, the programmable nuclease circuits of the present disclosure use components of the TAL/TALEN system to selectively cleave DNA encoding a gene of interest such as, for example, a toxin gene, a virulence factor gene, an antibiotic resistance gene, a remodeling gene or a modulatory gene. Transcriptional activator-like (TAL) effectors are proteins that can be engineered to target specific gene sequences. The genes were originally discovered in a bacterial plant pathogen that uses the TAL effectors to alter host gene expression. TAL effector nucleases (TALENs) are novel classes of sequence-specific nucleases, created by the fusion of a TAL effector (TALE) DNA binding domain to the catalytic head of an endonuclease (N). For example, when a TALE is fused to a nuclease known as Fold, the resulting TALEN can dimerize with a second TALEN and cleave DNA flanked by left and right target sites (Christian, M. et al. *Genetics* 186, 757-61 (2010)).

The first component of a TALEN is the TALE domain. In the nucleus they bind specific sequences within gene promoters to modulate host resistance mechanisms. Each TALE contains a highly conserved central region consisting of varying numbers of repeat units of typically 33 to 35 amino acids that confer specific DNA sequence recognition to the TALE protein. These repeat units contain high levels of identity with the exception of two variable amino acids at positions 12 and 13. These residues, termed the Repeat-Variable Di-residues (RVDs), confer DNA-binding specificity to the repeat region. The mechanism of DNA recognition of a TALE is therefore based on a simple code whereby one RVD recognizes one nucleotide of DNA sequence and ensures that the DNA binding domain of each TALE is capable of targeting large recognition sites with high precision (15-30 nucleotides).

The second component of a TALEN is the catalytic domain of an endonuclease that introduces DNA double strand breaks (DSBs) in vitro and in vivo, and which is fused to the TALE DNA-binding domain.

Thus, in some embodiments of the present disclosure, the engineered autonomously distributed circuits of the present disclosure contain components of the TAL/TALEN system, including a transcriptional activator like effector (TALE) fused to an endonuclease.

Programmable Zinc Finger Nucleases

In some embodiments, the programmable nuclease circuits of the present disclosure use zinc finger nucleases (ZFNs) to selectively cleave DNA encoding a gene of interest such as, for example, a toxin gene, a virulence factor gene, an antibiotic resistance gene, a remodeling gene or a modulatory gene. ZFNs are artificial restriction enzymes generated by fusing a zinc finger DNA-binding domain to a DNA-cleavage domain (Carroll, et al. *Nat Protoc,* 1(3), 1329-41 (2006)) Zinc finger domains can be engineered to target unique DNA sequences. The DNA-binding domains of individual ZFNs typically contain between three and six individual zinc finger repeats and can each recognize between 9 and 18 base pairs. The non-specific cleavage domain from the type II restriction endonuclease FokI is typically used as the cleavage domain in ZFNs (Kim, et al., *Proc Natl Acad Sci USA,* 93(3), 1156-60 (1996)). This cleavage domain dimerizes to cleave DNA (Bitinaite, et al. *Proc Natl Acad Sci USA* 95(18), 10570-5 (1998)) and thus a pair of ZFNs target non-palindromic DNA sites. In some embodiments, ZFNs are engineered by fusing the cleavage domain to the C-terminus of each zinc finger domain. In order to allow the two cleavage domains to dimerize and cleave DNA, the two individual ZFNs bind opposite strands of DNA with their C-termini a certain distance apart. In some embodiments, the linker sequences between the zinc finger domain and the cleavage domain requires the 5' edge of each binding site to be separated by 5 to 7 base pairs (bp) (Cathomen, et al. *Mol. Ther.* 16(7), 1200-7 (2008)).

Target Genes

Programmable nuclease circuits may be used to target most genes including, without limitation, genes or single nucleotide polymorphisms (SNPs) that confer resistance to traditional small molecule antimicrobials, genes that confer virulence traits to pathogens (e.g., *Escherichia coli, Shigella dysenteriae, Yersinia pestis, Francisella tularensis, Bacillus anthracis, Staphylococcus aureus, Streptococcus pyogenes, Vibrio cholerae, Pseudomonas aeruginosa, Klebsiella pneumoniae, Acinetobacter baumannii*, and *Salmonella enterica* Typhi), highly conserved genes that can typify microbial species, genera or phyla for the purposes of, e.g., remodeling complex microbial communities, and genes that encode enzymes involved in biochemical pathways with products that can modulate host physiology.

Examples of genes that confer aminoglycoside resistance include, without limitation, aph, aac and aad variants and other genes that encode aminoglycoside-modifying enzymes. Examples of genes with SNPs that confer aminoglycoside resistance include, without limitation, rpsL, rrnA and rrnB.

Examples of genes that confer beta-lactam resistance include, without limitation, genes that encode beta-lactamase (bla) (e.g., TEM, SHV, CTX-M, OXA, AmpC, IMP, VIM, KPC, NDM-1, family beta-lactamases) and mecA.

Examples of genes with SNPs that confer daptomycin resistance include, without limitation, mprF, yycFG, rpoB and rpoC.

Examples of genes that confer macrolide-lincosamide-streptogramin B resistance include, without limitation, ermA, ermB and ermC.

Examples of genes that confer quinolone resistance include, without limitation, qnrA, qnrS, qnrB, qnrC and qnrD. Examples of genes with SNPs that confer quinolone resistance include, without limitation, gyrA and parC.

Examples of genes with SNPs that confer trimethoprim/sulfonamide resistance include, without limitation, the dihydrofolate reductase (DHFR) and dihydropteroate synthase (DHPS) genes.

Examples of genes that confer vancomycin resistance include, without limitation, vanA (e.g., vanRS and vanHAX), vanB and vanC operons.

In some embodiments, the engineered autonomously distributed circuits may be used to target SNPs, which cause overexpression of genes that encode multi-drug efflux pumps, such as acrAB, mexAB, mexXY, mexCD, mefA, msrA and tetL.

Examples of genes that confer virulence traits to *Escherichia coli* (e.g., O157:H7) include, without limitation, stx1 and stx2 (encode Shiga-like toxins) and espA (responsible for induction of enterocyte effacement (LEE) A/E lesions). Other examples of genes that confer virulence traits to *Escherichia coli* include fimA (fimbriae major subunit), csgD (curli regulator) and csgA.

Examples of genes that confer virulence traits to *Shigella dysenteriae* include, without limitation, stx1 and stx2.

An example of a gene that confers virulence traits to *Yersinia pestis* is yscF (plasmid-borne (pCD1) T3SS external needle subunit).

An example of a gene that confers virulence traits to *Francisella tularensis* is fslA.

An example of a gene that confers virulence traits to *Bacillus anthracis* is pag (Anthrax toxin, cell-binding protective antigen).

Examples of genes that confer virulence traits to *Vibrio cholerae* include, without limitation, ctxA and ctxB (cholera toxin), tcpA (toxin co-regulated pilus), and toxT (master virulence regulator).

Examples of genes that confer virulence traits to *Pseudomonas aeruginosa* include, without limitation, genes that encode for the production of siderophore pyoverdine (e.g., sigma factor pvdS, biosynthetic genes pvdL, pvdI, pvdJ, pvdH, pvdA, pvdF, pvdQ, pvdN, pvdM, pvdO, pvdP, transporter genes pvdL, pvdR, pvdT and opmQ), genes that encode for the production of siderophore pyochelin (e.g., pchD, pchC, pchB, pchA, pchE, pchF and pchG, and genes that encode for toxins (e.g., exoU, exoS and exoT).

Examples of genes that confer virulence traits to *Klebsiella pneumoniae* include, without limitation, fimA (adherence, type I fimbriae major subunit), and cps (capsular polysaccharide).

Examples of genes that confer virulence traits to *Acinetobacter baumannii* include, without limitation, ptk (capsule polymerization) and epsA (assembly).

Examples of genes that confer virulence traits to *Salmonella enterica* Typhi include, without limitation, hilA (invasion, SPI-1 regulator), ssrB (SPI-2 regulator), and those associated with bile tolerance, including efflux pump genes acrA, acrB and tolC.

Examples of highly conserved genes that can typify microbial species, genera or phyla for the purposes of remodeling complex microbial communities (referred to herein as "remodeling" genes) include, without limitation, ribosomal components rrnA, rpsL, rpsJ, rplO, rpsM, rplC, rpsH, rplP, and rpsK, transcription initiation factor infB, and tRNA synthetase pheS.

Examples of genes encoding enzymes involved in biochemical pathways with products that can modulate host physiology (referred to herein as "modulatory" genes include, without limitation, (1) genes encoding enzymes involved in deoxycholate production linked to hepatocellular carcinoma, (2) genes encoding enzymes involved in polysaccharide A production by *Bacteroides fragilis*, leading to development of regulatory T cells (TREG), IL-10 response and increased TH1 cell numbers, (3) genes encoding enzymes involved in butyrate production leading to secretion of inducible antimicrobial peptides, (4) genes encoding enzymes involved in short-chain fatty acid production leading to increased energy harvest, obesity, inflammatory modulation and gastrointestinal wound healing, (5) genes encoding enzymes involved in transformation of choline into methylamines, which can disrupt glucose homeostasis, leading to non-alcoholic fatty liver disease and cardiovascular disease, (6) genes encoding enzymes involved in the generation of neuromodulatory compounds such as γ-aminobutyric acid, noradrenaline, 5-HT, dopamine and acetylcholine, and (7) genes encoding enzymes involved in the formation of lactic acid and propionic acid linked to anxiety.

Any of the foregoing genes or any other gene (e.g., biothreat gene) may be targeted by the programmable nuclease circuits of the present disclosure.

Delivery Vehicles

Programmable nuclease circuits may be loaded into vehicles for target, or broad, delivery and dissemination including, without limitation, engineered phagemids (Lu, T. K., et al. *Current Opinion in Microbiology* 14, 524-531 (2011)), bacteriophages and broad-host-range and plasmids (e.g., conjugative plasmids) delivered via transfer-competent probiotic bacteria. Other delivery vehicles contemplated herein include, without limitation, chemical-based delivery vehicles (e.g., cyclodextrin, calcium phosphate, cationic polymers, cationic liposomes), nanoparticle-based delivery vehicles (or platforms), non-chemical-based delivery vehicles (e.g., electroporation, sonoporation, optical transfection), particle-based delivery vehicles (e.g., gene gun, magnetofection, impalefection, particle bombardment, cell-penetrating peptides), and viral-based delivery vehicles (e.g., use of viruses as carriers). The choice of delivery vehicle/platform will depend, in part, on the type of cell to which the programmable nuclease circuits are delivered as well as the environment of the cells (e.g., in vivo v. in vitro). In some embodiments, microbial cells may be naturally competent and take up DNA from the environment on their own. In some embodiments, two or more different bacteriophages or phagemids or other combination of delivery vehicles may be used together as a delivery cocktail (Goodridge, L. D. *Current Pharmaceutical Biotechnology* 11, 15-27 (2010)). These delivery platforms enable the introduction and distribution of programmable nuclease circuits in microbial populations, where they can, in some instances, autonomously spread.

Phagemids

In some embodiments of the present disclosure, programmable nuclease circuits may be loaded into engineered phagemids, or phasmids, for delivery to microbial cell populations. As used herein, a phagemid refers to a phage-derived vector containing the replication origin of a plasmid and the packaging site of a bacteriophage.

Examples of phagemids that may be used in accordance with the invention include, without limitation, M13-derived phagemids containing the f1 origin for filamentous phage packaging such as, for example, pBluescript II SK (+/−) and KS (+/−) phagemids, pBC SK and KS phagemids, pADL and P1-based phagemids (see, e.g., Westwater C A et al., *Microbiology* 148, 943-50 (2002); Kittleson J T et al., *ACS Synthetoc Biology* 1, 583-89 (2012); Mead D A et al., *Biotechnology* 10, 85-102 (1988)). Other phagemids may be used in accordance with the present disclosure and, for example, can be made to work with packaging systems from natural, engineered or evolved bacteriophage.

Bacteriophages

In some embodiments of the present disclosure, programmable nuclease circuits, or phagemids containing programmable nuclease circuits, may be loaded into naturally-occurring, engineered (e.g., rationally engineered), or adaptively evolved bacteriophage for delivery to microbial cell populations, e.g., endogenous microbial cells. A bacteriophage, or phage, is a virus that infects and replicates in bacteria. Bacteriophages are composed of proteins that encapsulate a DNA or RNA genome and may have relatively simple or elaborate structures. Their genomes may encode as few as four genes, and as many as hundreds of genes. Bacteriophages replicate within bacteria following the injection of their genome into the cytoplasm and do so using either a lytic cycle, which results in bacterial cell lysis, or a lysogenic (non-lytic) cycle, which leaves the bacterial cell intact. The bacteriophages of the present disclosure are, in some embodiments, non-lytic (also referred to as lysogenic or temperate). Non-lytic phage may also include those that are actively secreted from infected cells in the absence of lysis, including, without limitation, filamentous phage such as, for example, M13, fd, IKe, CTX-ϕ, Pf1, Pf2 and Pf3. Thus, after phage delivery of a programmable nuclease circuit to a bacterial cell, the bacterial cell may remain viable and able to stably maintain expression of the circuit. In some embodiments, lytic bacteriophage may be used as delivery vehicles. When used with phagemid systems, naturally lytic phage serve as cargo shuttles and do not inherently lyse target cells.

Examples of non-lytic bacteriophage for use in accordance with the present disclosure include, without limitation, Myoviridae (P1-like viruses; P2-like viruses; Mu-like viruses; SPO1-like viruses; phiH-like viruses); Siphoviridae (λ-like viruses, γ-like viruses, T1-like viruses; T5-like viruses; c2-like viruses; L5-like viruses; psiM1-like viruses; phiC31-like viruses; N15-like viruses); Podoviridae (phi29-like viruses; P22-like viruses; N4-like viruses); Tectiviridae (Tectivirus); Corticoviridae (Corticovirus); Lipothrixviridae (Alphalipothrixvirus, Betalipothrixvirus, Gammalipothrixvirus, Deltalipothrixvirus); Plasmaviridae (Plasmavirus); Rudiviridae (Rudivirus); Fuselloviridae (Fusellovirus); Inoviridae (Inovirus, Plectrovirus, M13-like viruses, fd-like viruses); Microviridae (Microvirus, Spiromicrovirus, Bdellomicrovirus, Chlamydiamicrovirus); Leviviridae (Levivirus, Allolevivirus) and Cystoviridae (Cystovirus). Such phages may be naturally occurring or engineered phages. In some embodiments, the bacteriophage is a coliphage (e.g., infects *Escherichia coli*). In some embodiments, the bacteriophage of the present disclosure target bacteria other than *Escherichia coli*, including, without limitation, *Bacteroides thetaiotamicron* (e.g., B1), *B. fragilis* (e.g., ATCC 51477-B1, B40-8, Bf-1), *B. caccae* (e.g., phiHSC01), *B. ovatus* (e.g., phiHSC02), *Clostridium difficile* (e.g., phiC2, phiC5, phiC6, phiC8, phiCD119, phiCD27), *Klebsiella pneumoniae* (e.g., KPO1K2, K11, Kpn5, KP34, JD001), *Staphylococcus aureus* (e.g., phiNM1, 80alpha), *Enterococcus faecalis* (e.g., IME-EF1), *Enterococcus faecium* (e.g., ENB6, C33), and *Pseudomonas aeruginosa* (e.g., phiKMV, PAK-P1, LKD16, LKA1, delta, sigma-1, J-1). Other bacteriophage may be used in accordance with the present disclosure.

In some embodiments, the bacteriophage of the present disclosure is an M13 bacteriophage. M13 is a filamentous bacteriophage of the family Inoviridae and is composed of circular single-stranded DNA. M13 phages are about 900 nm long and 6-7 nm in diameter with 5 proteins. The minor coat protein, P3, attaches to the receptor at the tip of the F pilus of an *Escherichia coli* host cell. Thus, in some embodiments, the methods comprise delivering to bacterial cells a recombinant M13 bacteriophage that is engineered to contain at least one programmable nuclease circuit.

It should be appreciated that the bacteriophages of the present disclosure can be isolated from any environment where bacteria exist. In some embodiments, the bacteriophages of the invention are isolated from (e.g., collected from, obtained from) stool or sewage. In other embodiments, the bacteriophages of the present disclosure are isolated from terrestrial or marine environments. Isolated bacteriophages may be further modified by rational design including, without limitation, alterations in host range determination factors such as the addition, deletion, or swapping of components of tail fibers, capsule binding and/or degrading enzymes, phage counter defense genes (immunity to restriction, anti-CRISPR genes, antitoxins or other products to subvert programmed cell death), biocontainment modules, and modifications involved in the generation of phagemid packaging systems (e.g. modification or deletion of packaging site from phage genome). These components and unknown components may also be modified through adaptive evolution designed to improve efficiency of delivery or expand the host range of the phages.

Broad-Host-Range and Conjugative Plasmids

In some embodiments of the present disclosure, programmable nuclease circuits may be loaded into broad-host-range and conjugative plasmids for delivery to microbial cell populations, e.g., endogenous microbial cells. Conjugative transfer of bacterial plasmids is the primary route of broad host range DNA transfer between different genera of bacteria and is the most efficient way of horizontal gene spread. Conjugative transfer is thus considered one of the major reasons for the increase in the number of bacteria exhibiting multiple-antibiotic resistance. Various aspects of the present disclosure are directed to exploiting the natural phenomena of conjugative transfer of plasmids to deliver programmable nuclease circuits to microbial cells in vivo, which prevents and/or reverses, for example, antibiotic resistance in the cells.

To promote propagation of programmable nuclease circuits, the present disclosure contemplates the use of plasmids with broad-host-range origins of replication. Such plasmid origins include, without limitation, those derived from major broad-host-range incompatibility groups IncQ (e.g., RSF1010, R300B, R1162), IncW (e.g., pSa, pR388), IncP (e.g., R18, R68, RK2, RP1, RP4), IncN and IncU (e.g., RA3), and pBBR1 (Lale, R., et al. *Strain Engineering*, Vol. 765 (ed. Williams, J. A.) 327-343 (Humana Press, 2011)). Other broad-host-range and conjugative plasmids may be used in accordance with the invention.

Mobile Genetic Elements

In some embodiments of the invention, mobile genetic elements other than conjugative vectors can be used to facilitate transfer into target strains. Such elements may include, without limitation, integrative conjugative elements (e.g., SXT, PAPI-1), integrative and mobilizable elements (e.g., SGI1), cis-mobilizable elements, conjugative transposons (e.g., Tn916, Tn1545, Tn5276, Tn5397, CTnDOT), mobile pathogenicity islands (e.g., SaPI1), and prophages (e.g., P1, Lambda, 933W, phiNM1, 80alpha), among others.

Donor Bacteria

In some embodiments of the present disclosure, programmable nuclease circuits, or broad-host-range and conjugative plasmids, may be loaded into donor bacteria (e.g., probiotic bacteria and/or commensal bacteria) for delivery to microbial cell populations, e.g., endogenous microbial cells. Probiotic bacteria, for example, are live bacteria that may confer a health benefit on the host and/or, at the very least, are not harmful (e.g., not pathogenic) to the host. Commensal bacteria (also referred to as commensal microflora), as another example, include bacteria present on body surfaces covered by epithelial cells that are exposed to the external environment (e.g., gastrointestinal and respiratory tract, vaginal, skin). Commensal bacteria are found, for example, in normal microflora and indigenous microbiota. As discussed above, bacterial plasmids are transferred from bacteria to bacteria through conjugation. Thus, aspects of the invention contemplate the use of donor bacteria (e.g., probiotic bacteria and/or commensal bacteria) loaded with plasmids containing programmable nuclease circuits to deliver the circuits to microbial cells (e.g., pathogenic microbial cells) in vivo. In other embodiments of the present disclosure, probiotic bacteria may be loaded with non-lytic or inducible bacteriophage that can express and generate bacteriophage-based delivery particles in situ.

Examples of probiotic bacteria for use in accordance with the present disclosure include, without limitation, *Bacillus coagulans* GBI-30, 6086, *Bifidobacterium animalis* subsp. *lactis* BB-12, *Bifidobacterium longum* subsp. *infantis*, *Escherichia coli* Nissle 1917, *Lactobacillus acidophilus* NCFM, *Lactobacillus paracasei* St11 (or NCC2461), *Lactobacillus johnsonii* La1 (also referred to as *Lactobacillus* LC1, *Lactobacillus johnsonii* NCC533), *Lactobacillus plantarum* 299v, *Lactobacillus reuteri* ATCC 55730 (*Lactobacillus reuteri* SD2112), *Lactobacillus reuteri Protectis* (DSM 17938, daughter strain of ATCC 55730), *Lactobacillus reuteri Prodentis* (DSM 17938/ATCC 55730 and ATCC PTA 5289 in combination), *Lactobacillus rhamnosus* GG, *Saccharomyces boulardii*, mixture of *Lactobacillus rhamnosus* GR-1 and *Lactobacillus reuteri* RC-14, a mixture of *Lactobacillus acidophilus* NCFM and *Bifidobacterium bifidum* BB-12, a mixture of *Lactobacillus acidophilus* CL1285 and *Lactobacillus casei* LBC80R, a mixture of *Lactobacillus plantarum* HEAL 9 and *Lactobacillus paracasei* 8700:2, *Lactobacillus bulgaricus, Lactococcus thermophiles* and/or *Lactobacillus bifidus*. In some embodiments, probiotic bacteria for use in accordance with the present disclosure may be a mixture of any two or more of the foregoing strains.

In some embodiments, live probiotic bacterial cells may be derived/obtained/isolated from, and/or delivered in vivo in, fermented dairy products and probiotic fortified foods (e.g., pickled vegetables, fermented bean paste (e.g., tempeh, miso, doenjang), kefir, buttermilk or karnemelk, kimchi, pao cai, sauerkraut, soy sauce, zha cai). In other embodiments, the probiotic bacteria may be delivered in vivo as tablets, capsules, powders and/or sachets containing the bacteria in freeze dried form. Alternatively, in some embodiments, probiotic bacteria may be delivered by means of a fecal microbiota transplant.

Microbial/Bacterial Cells

Bacteria are small (typical linear dimensions of around 1 micron), non-compartmentalized organisms, with at least one circular DNA chromosomes and ribosomes of 70S. As used herein, the term "bacteria" encompasses all variants of bacteria (e.g., endogenous bacteria, which naturally reside in a closed system, environmental bacteria or bacteria released for bioremediation or other efforts). Bacterial cells of the present disclosure include bacterial subdivisions of *Eubacteria* and *Archaebacteria*. *Eubacteria* can be further subdivided into Gram-positive and Gram-negative *Eubacteria*, which depend upon a difference in cell wall structure. Also included herein are those classified based on gross morphology alone (e.g., cocci, bacilli). In some embodiments, the bacterial cells are Gram-negative cells, and in some embodiments, the bacterial cells are Gram-positive cells. Examples of bacterial cells of the present disclosure include, without limitation, cells from *Yersinia* spp., *Escherichia* spp., *Klebsiella* spp., *Acinetobacter* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp., or *Lactobacillus* spp. In some embodiments, the bacterial cells are from *Bacteroides thetaiotaomicron, Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinobycetemcomitans, cyanobacteria, Escherichia coli, Helicobacter pylori, Selnomonas ruminatium, Shigella sonnei, Zymomonas mobilis, Mycoplasma mycoides, Treponema denticola, Bacillus thuringiensis, Staphlococcus lugdunensis, Leuconostoc oenos, Corynebacterium xerosis, Lactobacillus plantarum, Lactobacillus rhamnosus, Lactobacillus casei, Lactobacillus acidophilus, Streptococcus* spp., *Enterococcus faecalis, Bacillus coagulans, Bacillus ceretus, Bacillus*

*popillae, Synechocystis* strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Zymomonas mobilis, Streptomyces phaechromogenes*, or *Streptomyces ghanaenis*. Thus, the bacteriophage of the present disclosure may target (e.g., specifically target) a bacterial cell from any one or more of the foregoing genus and/or species of bacteria. Other bacterial cells and microbes may also be targeted. As used herein, "endogenous" bacterial cells may refer to non-pathogenic bacteria that are part of a normal internal ecosystem such as bacterial flora.

In some embodiments, bacterial cells of the present disclosure are anaerobic bacterial cells (e.g., cells that do not require oxygen for growth). Anaerobic bacterial cells include facultative anaerobic cells such as, for example, *Escherichia coli, Shewanella oneidensis* and *Listeria monocytogenes*. Anaerobic bacterial cells also include obligate anaerobic cells such as, for example, *Bacteroides* and *Clostridium* species. In humans, for example, anaerobic bacterial cells are most commonly found in the gastrointestinal tract. Thus, the bacteriophage of the present disclosure may target (e.g., specifically target) anaerobic bacterial cells.

Genetic Elements and Engineering

The programmable nuclease circuits of the present disclosure contain at least one genetic element that can regulate gene/protein expression. A "genetic element," as used herein, refers to a nucleotide sequence that has a role in gene expression. For example, nucleic acids (e.g., recombinant nucleic acids) encoding proteins, promoters, enhancers and terminators are considered to be genetic elements. The programmable nuclease circuits of the invention may be engineered using, for example, standard molecular cloning methods (see, e.g., *Current Protocols in Molecular Biology*, Ausubel, F. M., et al., New York: John Wiley & Sons, 2006; Molecular Cloning: A Laboratory Manual, Green, M. R. and Sambrook J., New York: Cold Spring Harbor Laboratory Press, 2012; Gibson, D. G., et al., *Nature Methods* 6(5):343-345 (2009), the teachings of which relating to molecular cloning are herein incorporated by reference).

Nucleic Acids

As used herein, the term "nucleic acid" refers to at least two nucleotides covalently linked together, and in some instances, may contain phosphodiester bonds (e.g., a phosphodiester "backbone"). In some embodiments, a nucleic acid of the present disclosure may be considered to be a nucleic acid analog, which may contain other backbones comprising, for example, phosphoramide, phosphorothioate, phosphorodithioate, O-methylphophoroamidite linkages, and/or peptide nucleic acids. Nucleic acids (e.g., components, or portions, of the nucleic acids) of the present disclosure may be naturally occurring or engineered. Engineered nucleic acids include recombinant nucleic acids and synthetic nucleic acids. "Recombinant nucleic acids" may refer to molecules that are constructed by joining nucleic acid molecules and, in some embodiments, can replicate in a living cell. "Synthetic nucleic acids" may refer to molecules that are chemically or by other means synthesized or amplified, including those that are chemically or otherwise modified but can base pair with naturally occurring nucleic acid molecules. Recombinant and synthetic nucleic acids also include those molecules that result from the replication of either of the foregoing.

The nucleic acids may be single-stranded (ss) or double-stranded (ds), as specified, or may contain portions of both single-stranded and double-stranded sequence. The nucleic acid may be DNA, both genomic and cDNA, RNA or a hybrid/chimeric, where the nucleic acid contains any combination of deoxyribo- and ribonucleotides, and any combination of bases, including uracil, adenine, thymine, cytosine, guanine, inosine, xanthine, hypoxanthine, isocytosine, and isoguanine.

Some aspects of the present disclosure provide methods that include delivering to microbial cells in vivo a delivery vehicle with at least one nucleic acid encoding an engineered autonomously distributed circuit that contains a programmable nuclease that targets a gene or nucleotide sequence of interest. It should be understood that components of the circuit, including the programmable nuclease, may be encoded by a single nucleic acid (e.g., on the same plasmid or other vector) or by multiple different (e.g., independently-replicating) nucleic acids.

Promoters

The programmable nuclease circuits of the present disclosure may contain nucleic acids with promoter sequences, or promoters, operably linked to a nucleotide sequence encoding a gene product of interest. As used herein, a "promoter" refers to a control region of a nucleic acid sequence at which initiation and rate of transcription of the remainder of a nucleic acid sequence are controlled. A promoter may also contain sub-regions at which regulatory proteins and molecules may bind, such as RNA polymerase and other transcription factors. Promoters may be constitutive, inducible, activatable, repressible, tissue-specific or any combination thereof.

A promoter drives expression or drives transcription of the nucleic acid sequence that it regulates. Herein, a promoter is considered to be "operably linked" when it is in a correct functional location and orientation in relation to a nucleic acid sequence it regulates to control ("drive") transcriptional initiation and/or expression of that sequence.

A promoter may be classified as strong or weak according to its affinity for RNA polymerase (and/or sigma factor); this is related to how closely the promoter sequence resembles the ideal consensus sequence for the polymerase. The strength of a promoter may depend on whether initiation of transcription occurs at that promoter with high or low frequency. Different promoters with different strengths may be used to construct programmable nuclease circuits with different levels of gene/protein expression (e.g., the level of expression initiated from a weak promoter is lower than the level of expression initiated from a strong promoter).

A promoter may be one naturally associated with a gene or sequence, as may be obtained by isolating the 5' non-coding sequences located upstream of the coding segment of a given gene or sequence. Such a promoter can be referred to as "endogenous." Similarly, an activator/enhancer may be one naturally associated with a nucleic acid sequence, located either within or downstream or upstream of that sequence.

In some embodiments, a coding nucleic acid segment may be positioned under the control of a recombinant or heterologous promoter, which refers to a promoter that is not normally associated with the encoded nucleic acid sequence in its natural environment. A recombinant or heterologous enhancer refers to an enhancer not normally associated with a nucleic acid sequence in its natural environment. Such promoters or enhancers may include promoters or enhancers of other genes; promoters or enhancers isolated from any other prokaryotic cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR) (see U.S. Pat. Nos. 4,683,202 and 5,928,906).

Inducible Promoters

As used herein, an "inducible promoter" is one that is characterized by initiating or enhancing transcriptional activity when in the presence of, influenced by or contacted by an inducer or inducing agent. An "inducer" or "inducing agent" may be endogenous or a normally exogenous condition, compound or protein that contacts a programmable nuclease circuit in such a way as to be active in inducing transcriptional activity from the inducible promoter.

Inducible promoters for use in accordance with the present disclosure function in a microbial cell such as a bacterial cell. Examples of inducible promoters for use herein include, without limitation, bacteriophage promoters (e.g. Pls1con, T3, T7, SP6, PL) and bacterial promoters (e.g. Pbad, PmgrB, Ptrc2, Plac/ara, Ptac, Pm), or hybrids thereof (e.g. PLlacO, PLtetO). Examples of bacterial promoters for use in accordance with the present disclosure include, without limitation, positively regulated *E. coli* promoters such as positively regulated $\sigma^{70}$ promoters (e.g., inducible pBad/araC promoter, Lux cassette right promoter, modified lamdba Prm promote, plac Or2-62 (positive), pBad/AraC with extra REN sites, pBad, P(Las) TetO, P(Las) CIO, P(Rhl), Pu, FecA, pRE, cadC, hns, pLas, pLux), $\sigma^{S}$ promoters (e.g., Pdps), $\sigma^{32}$ promoters (e.g., heat shock) and $\sigma^{54}$ promoters (e.g., glnAp2); negatively regulated *E. coli* promoters such as negatively regulated $\sigma^{70}$ promoters (e.g., Promoter (PRM+), modified lamdba Prm promoter, TetR-TetR-4C P(Las) TetO, P(Las) CIO, P(Lac) IQ, RecA_DlexO_D-LacO1, dapAp, FecA, Pspac-hy, pcI, plux-cI, plux-lac, CinR, CinL, glucose controlled, modifed Pr, modifed Prm+, FecA, Pcya, rec A (SOS), Rec A (SOS), EmrR_regulated, BetI_regulated, pLac_lux, pTet_Lac, pLac/Mnt, pTet/Mnt, LsrA/cI, pLux/cI, LacI, LacIQ, pLacIQ1, pLas/cI, pLas/Lux, pLux/Las, pRecA with LexA binding site, reverse BBa_R0011, pLacI/ara-1, pLaclq, rrnB P1, cadC, hns, PfhuA, pBad/araC, nhaA, OmpF, RcnR), $\sigma^{S}$ promoters (e.g., Lutz-Bujard LacO with alternative sigma factor $\sigma^{38}$), $\sigma^{32}$ promoters (e.g., Lutz-Bujard LacO with alternative sigma factor $\sigma^{32}$), and $\sigma^{54}$ promoters (e.g., glnAp2); negatively regulated *B. subtilis* promoters such as repressible *B. subtilis* $\sigma^{A}$ promoters (e.g., Gram-positive IPTG-inducible, Xyl, hyper-spank) and $\sigma^{B}$ promoters. Other inducible microbial promoters and/or bacterial promoters may be used in accordance with the present disclosure.

The administration or removal of an inducer results in a switch between activation and inactivation of the transcription of the operably linked nucleic acid sequence (e.g., nucleic acid encoding a gene product of interest). Thus, as used herein, the active state of a promoter operably linked to a nucleic acid sequence refers to the state when the promoter is actively driving transcription of the nucleic acid sequence (i.e., the linked nucleic acid sequence is expressed). Conversely, the inactive state of a promoter operably linked to a nucleic acid sequence refers to the state when the promoter is not actively driving transcription of the nucleic acid sequence (i.e., the linked nucleic acid sequence is not expressed).

An inducible promoter for use in accordance with the present disclosure may be induced by (or repressed by) one or more physiological condition(s), such as changes in pH, temperature, radiation, osmotic pressure, saline gradients, cell surface binding, and the concentration of one or more extrinsic or intrinsic inducing agent(s). The extrinsic inducer or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Inducible promoters for use in accordance with the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some embodiments, the inducer used in accordance with the present disclosure is an N-acyl homoserine lactone (AHL), which is a class of signaling molecules involved in bacterial quorum sensing. Quorum sensing is a method of communication between bacteria that enables the coordination of group based behavior based on population density. AHL can diffuse across cell membranes and is stable in growth media over a range of pH values. AHL can bind to transcriptional activators such as LuxR and stimulate transcription from cognate promoters. In some embodiments, the inducer used in accordance with the present disclosure is anhydrotetracycline (aTc), which is a derivative of tetracycline that exhibits no antibiotic activity and is designed for use with tetracycline-controlled gene expression systems, for example, in bacteria.

Other inducible promoter systems are known in the art and may be used in accordance with the present disclosure.

Enhancers

In some embodiments of the present disclosure, a promoter may or may not be used in conjunction with an "enhancer," which refers to a cis-acting regulatory sequence involved in the transcriptional activation of a nucleic acid sequence downstream of the promoter. The enhancer may be located at any functional location before or after the promoter.

Terminators

In some embodiments, a programmable nuclease circuit may contain a terminator sequence, or terminator. A "terminator," as used herein, is a nucleic acid sequence that causes transcription to stop. A terminator may be unidirectional or bidirectional. It is comprised of a DNA sequence involved in specific termination of an RNA transcript by an RNA polymerase. A terminator sequence prevents transcriptional activation of downstream nucleic acid sequences by upstream promoters. Thus, in certain embodiments, a terminator that ends the production of an RNA transcript is contemplated. A terminator may be necessary in vivo to achieve desirable gene/protein expression levels.

The most commonly used type of terminator is a forward terminator. When placed downstream of a nucleic acid sequence that is usually transcribed, a forward transcriptional terminator will cause transcription to abort. In some embodiments, bidirectional transcriptional terminators are provided, which usually cause transcription to terminate on both the forward and reverse strand. In some embodiments, reverse transcriptional terminators are provided, which usually terminate transcription on the reverse strand only.

In prokaryotic systems, terminators usually fall into two categories (1) rho-independent terminators and (2) rho-dependent terminators. Rho-independent terminators are generally composed of palindromic sequence that forms a stem loop rich in G-C base pairs followed by a string of uracil bases.

Terminators for use in accordance with the present disclosure include any terminator of transcription described herein or known to one of ordinary skill in the art. Examples of terminators include, without limitation, the termination sequences of genes such as, for example, the bovine growth hormone terminator, and viral termination sequences such as, for example, the T0 terminator, the TE terminator, Lambda T1 and the T1T2 terminator found in bacterial systems. In some embodiments, the termination signal may be a sequence that cannot be transcribed or translated, such as those resulting from a sequence truncation.

Other genetic elements are known in the art and may be used in accordance with the present disclosure.

Recombinase-Based Programmable Nuclease Circuits

In some embodiments of the present disclosure, the microbial cells (e.g., bacterial cells) may be functionalized with recombinase-based programmable nuclease circuits. A "recombinase," as used herein, is a site-specific enzyme that recognizes short DNA sequence(s), which sequence(s) are typically between about 30 base pairs (bp) and 40 bp, and that mediates the recombination between these recombinase recognition sequences, which results in the excision, integration, inversion, or exchange of DNA fragments between the recombinase recognition sequences. For example, in some embodiments, recombinant bacteriophages of the present disclosure may be engineered to deliver at least two programmable nuclease circuits, one containing a nucleic acid with an inducible promoter operably linked to a nucleic acid encoding a recombinase, and the other containing a nucleic acid with a promoter operably linked to a nucleotide sequence encoding a gene product of interest and optionally containing a terminator, wherein at least one of the promoter and terminator is flanked by a forward and a reverse recognition site of the recombinase. In such embodiments, expression of the gene product of interest of one circuit is regulated by recombinase activity, or inactivity, of the other circuit.

Recombinases can be classified into two distinct families: serine recombinases (e.g., resolvases and invertases) and tyrosine recombinases (e.g., integrases), based on distinct biochemical properties. Serine recombinases and tyrosine recombinases are further divided into bidirectional recombinases and unidirectional recombinases. Examples of bidirectional serine recombinases for use herein include, without limitation, β-six, CinH, ParA and γδ; and examples of unidirectional serine recombinases include, without limitation, Bxb1, ϕC31, TP901, TG1, φBT1, R4, φRV1, φFC1, MR11, A118, U153 and gp29. Examples of bidirectional tyrosine recombinases for use herein include, without limitation, Cre, FLP, and R; and unidirectional tyrosine recombinases include, without limitation, Lambda, HK101, HK022 and pSAM2. The serine and tyrosine recombinase names stem from the conserved nucleophilic amino acid residue that the recombinase uses to attack the DNA and which becomes covalently linked to the DNA during strand exchange.

The outcome of recombination depends, in part, on the location and orientation of two short repeated DNA sequences that are to be recombined, typically less than 30 bp long. Recombinases bind to these repeated sequences, which are specific to each recombinase, and are herein referred to as "recombinase recognition sequences" or "recombinase recognition sites." Thus, as used herein, a recombinase is "specific for" a recombinase recognition site when the recombinase can mediate inversion or excision between the repeat nucleotide sequences. As used herein, a recombinase may also be said to recognize its "cognate recombinase recognition sites," which flank an intervening genetic element (e.g., promoter, terminator, or output nucleic acid sequence). A genetic element is said to be "flanked" by recombinase recognition sites when the element is located between and immediately adjacent to two repeated nucleotide sequences.

Recombinases can also be classified as irreversible or reversible. As used herein, an "irreversible recombinase" refers to a recombinase that can catalyze recombination between two complementary recombination sites, but cannot catalyze recombination between the hybrid sites that are formed by this recombination without the assistance of an additional factor. Thus, an "irreversible recognition site" refers to a recombinase recognition site that can serve as the first of two nucleotide recognition sequences for an irreversible recombinase and that is modified to a hybrid recognition site following recombination at that site. A "complementary irreversible recognition site" refers to a recombinase recognition site that can serve as the second of two nucleotide recognition sequences for an irreversible recombinase and that is modified to a hybrid recombination site following homologous recombination at that site.

Irreversible recombinases, and nucleic acids that encode the irreversible recombinases, are described in the art and can be obtained using routine methods. Examples of irreversible recombinases include, without limitation, phiC31 ((φC31) recombinase, coliphage P4 recombinase (Ow & Ausubel, *J. Bacteriol.* 155, 704-713 (1983)), coliphage lambda integrase (Lorbach et al., *J. Mol. Biol.,* 296, 1175-81 (2000)), Listeria A118 phage recombinase (Loessner et al., *Mol. Micro.* 35, 324-340 (2000)), and actinophage R4 Sre recombinase (Matsuura et al., *J Bacteriol.* 178, 3374-3376 (1996)), HK101, HK022, pSAM2, Bxb1, TP901, TG1, φpBT1, φRV1, φFC1, MR11, U153 and gp29.

Conversely, a "reversible recombinase" refers to a recombinase that can catalyze recombination between two complementary recombinase recognition sites and, without the assistance of an additional factor, can catalyze recombination between the sites that are formed by the initial recombination event, thereby reversing it. The product-sites generated by recombination are themselves substrates for subsequent recombination. Examples of reversible recombinase systems include, without limitation, the Cre-lox and the Flp-frt systems, R, β-six, CinH, ParA and γδ.

In some embodiments, the recombinase is serine recombinase. Thus, in some embodiments, the recombinase is considered to be irreversible. In some embodiments, the recombinase is a tyrosine recombinase. Thus, in some embodiments, the recombinase is considered to be reversible.

The recombinases provided herein are not meant to be exclusive examples of recombinases that can be used in embodiments of the present disclosure. The complexity of the programmable nuclease circuits of the present disclosure can be expanded by mining databases for new orthogonal recombinases or designing synthetic recombinases with defined DNA specificities (Groth, A. C. & Calos, M. P. *J Mol Biol* 335, 667-678, (2004); Gordley, R. M., et al. *Proc Natl Acad Sci USA* 106, 5053-5058 (2009)). Other examples of recombinases that are useful in the programmable nuclease circuits described herein are known to those of skill in the art, and any new recombinase that is discovered or generated is expected to be able to be used in the different embodiments of the invention.

Programmable Nuclease Circuit Libraries

Provided herein are libraries of (e.g., a plurality of) programmable nuclease circuits, which are engineered to target a myriad of plasmid and chromosomal genes of interest (e.g., biothreat genes, remodeling genes, modulatory genes). The libraries of the present disclosure may contain any number of programmable nuclease circuits, each engineered to destroy/attenuate a target gene of interest. For example, the present disclosure contemplates "biothreat control" libraries of programmable nuclease circuits that target genes or single nucleotide polymorphisms (SNPs) that confer resistance to traditional small molecule antimicrobials, genes that confer virulence traits to pathogens, highly conserved genes that can typify microbial species, genera or phyla for the purposes of, e.g., remodeling complex microbial communities, and genes that encode enzymes involved in biochemical pathways with products that can modulate host physiology. Such pre-engineered libraries are particularly useful if the need to address a biothreat is immediate. A library of the present disclosure may contain, for each gene target, at least two (e.g., at least 3, at least 4, at least 5, at least 10, at least 25) programmable nuclease circuits targeting different loci of the gene target, thereby increasing efficiency and efficacy of gene target destruction/attenuation.

The present disclosure also contemplates multiplexed programmable nuclease circuit libraries wherein multiple guide RNA sequences are encoded into a single circuit to enable simultaneous targeting of several genes of interest. Natural CRISPR loci have been found to contain 58 spacers to simultaneously license Cas9 to induce double stranded breaks at 58 different DNA sequences (Gunderson, F. F., et al. *mBio* 4(2013)). Thus, in some embodiments, a programmable nuclease circuit may be engineered to target 2 to 60 different loci within the same gene target or across multiple gene targets. For example, a programmable nuclease circuit may be engineered to target 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 different DNA sequences. In some embodiments, a programmable nuclease circuit may be engineered to target more than 60 different loci within the same gene target or across multiple gene targets. For example, a programmable nuclease circuit may be engineered to target 65, 70, 75, 80, 85, 90, 95, 100 or more different DNA sequences.

Applications

Various aspects and embodiments of the present disclosure are directed to the use of programmable nucleases circuits to specifically target existing or new biothreat genes (e.g., harmful genes such as toxin genes, virulence genes, antibiotic resistance genes) or other genes or nucleotide sequences of interest in microbial/bacterial pathogens in vivo, as described elsewhere herein. The programmable nuclease circuits may be used, in some embodiments, to eliminate plasmid-borne biothreat genes (or other genes or nucleotide sequences of interest) or destroy, or put substantial selective pressure against, cells with chromosomally integrated biothreat genes (or other genes or nucleotide sequences of interest).

The programmable nuclease circuits may be delivered to microbial/bacterial cells alone or together with an antibiotic or other antimicrobial agent. Examples of antibiotics and antimicrobial agents that may be used in accordance with the present disclosure include, without limitation, aminoglycosides, ansamycins, carbapenems, cephalosporins ($1^{st}$-$5^{th}$ generation), glycopeptides, lincosamides, lipopeptides, macrolides, monobactams, nitrofurans, oxazolidonones, penicillins (and combinations with penecillins), polypeptides, quinolones, sulfonamides, tetracyclines, drugs against mycobacteria, and others.

Examples of aminoglycosides include, without limitation, Amikacin, Gentamicin, Kanamycin, Neomycin, Netilmicin, Tobramycin, Paromomycin and Spectinomycin.

Examples of ansamycins include, without limitation, Geldanamycin, Herbimycin and Rifaximin (streptomycin).

Examples of carbapenems include, without limitation, Ertapenem, Doripenem, Imipenem/Cilastatina and Meropenem.

Examples of cephalosporins include, without limitation, Cefadroxil, Cefazolin, Cefalotin or Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil and Ceftobiprole.

Examples of glycopeptides include, without limitation, Teicoplanin, Vancomycin and Telavancin.

Examples of lincosamides include, without limitation, Clindamycin and Lincomycin.

An example of a lipopeptide includes, without limitation, Daptomycin.

Examples of macrolides include, without limitation, Azithromycin, Clarithromycin, Dirithromycin, Erythromycin, Roxithromycin, Troleandomycin, Telithromycin and Spiramycin.

An example of a monobactams includes, without limitation, Aztreonam.

Examples of nitrofurans include, without limitation, Furazolidone and Nitrofurantoin.

Examples of oxazolidonones include, without limitation, Linezolid, Posizolid, Radezolid and Torezolid.

Examples of penicillins include, without limitation, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin and penicillin combinations (e.g., amoxicillin/clavulanate, ampicillin/sulbactam, piperacillin/tazobactam, ticarcillin/clavulanate).

Examples of polypeptides include, without limitation, bacitracin, colistin and polymyxin B.

Examples of quinolones include, without limitation, Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin and Temafloxacin.

Examples of sulfonamides include, without limitation, Mafenide, Sulfacetamide, Sulfadiazine, Silver sulfadiazine, Sulfadimethoxine, Sulfamethizole, Sulfamethoxazole, Sulfanilimide (archaic), Sulfasalazine, Sulfisoxazole, Trimethoprim-Sulfamethoxazole(Co-trimoxazole) (TMP-SMX) and Sulfonamidochrysoidine(archaic).

Examples of tetracyclines include, without limitation, Demeclocycline, Doxycycline, Minocycline, Oxytetracycline and Tetracycline.

Examples of drugs against mycobacteria include, without limitation, Clofazimine, Dapsone, Capreomycin, Cycloserine, Ethambutol, Ethionamide, Isoniazid, Pyrazinamide, Rifampicin (Rifampin in US), Rifabutin, Rifapentine and Streptomycin.

Examples of other antibiotic and antimicrobial agents include, without limitation, Arsphenamine, Chloramphenicol, Fosfomycin, Fusidic acid, Metronidazole, Mupirocin, Platensimycin, Quinupristin/Dalfopristin, Thiamphenicol, Tigecycline, Tinidazole and Trimethoprim.

In some embodiments, programmable nuclease circuits of the present disclosure may be used to target components of the CRISPR-Cas system in bacteria. Bacteria have evolved the CRISPR-Cas system defense mechanism to cope with various environmental stressors, including virus (e.g., bacteriophage) attack. By targeting components of the CRISPR-Cas system using the programmable nuclease circuits of the present disclosure, bacterial defenses, for example, to bacteriophage infection can be weakened. Thus, in some embodiments, provided herein are methods that comprise culturing bacterial cells and delivering to the cultured bacterial cells a delivery vehicle with at least one nucleic acid encoding an engineered autonomously distributed circuit that contains a programmable nuclease that targets a component of the CRISPR-Cas system (e.g., Cas9 nuclease, a guide RNA (gRNA), and/or a transactivating small RNA (tracrRNA) derived from the Type II CRISPR-Cas system of *Streptococcus pyogenes*, or derived from other CRISPR-Cas systems).

Also contemplated herein, in some embodiments, is the use of programmable nuclease circuits to identify bacteria that contain a gene or SNP of interest (e.g., an antibiotic resistance gene). Thus, in some embodiments, provided herein are methods that comprise culturing the bacterial cells of a sample, delivering to the cultured bacterial cells a delivery vehicle with at least one nucleic acid encoding an engineered autonomously distributed circuit that contains a programmable nuclease that targets a gene or nucleotide sequence of interest, and determining whether or not the bacterial cell survives, wherein bacterial cell death indicates the sample comprises bacterial cells with the gene of interest. Such methods may be useful in clinical applications to identify samples (e.g., biological fluid or tissue samples) from a subject that may contain (e.g., are suspected of containing), for example, antibiotic resistant bacterial cells. In some embodiments, the methods further comprise diagnosing the subject, or deciding on a course of therapy for the subject, based on whether or not the sample from the subject contains, for example, antibiotic resistant bacterial cells (or bacterial cells containing other genes of interest). Such methods of the present disclosure are particularly useful if, for example, a subject undergoing treatment for a bacterial infection is non-responsive to a particular antibiotic. In such cases, the methods of the present disclosure may be used to determine whether or not the subject is infected with pathogenic bacterial cells (e.g., MDR bacterial cells) that are resistant to the particular antibiotic being used to treat the subject (or to other antibiotics that may be considered as an alternative treatment).

In some embodiments, programmable nuclease circuits of the present disclosure may be used as a diagnostic. As indicated above and shown below in the Examples, programmable nuclease circuits can be used to detect nucleic acid mutations, including single nucleotide mutations. The programmable nuclease circuits can also be used to detect the presence or absence of genes (e.g., antibiotic resistance genes) and/or gene copy number. This may be achieved, for example, by coupling a programmable nuclease circuit to an SOS-responsive reporter construct, which includes, for example, an SOS-responsive promoter operably linked to a gene encoding a reporter molecule, such as green fluorescent protein (GFP). Other reporter molecules (e.g., other fluorescent reporter molecules) are contemplated herein. The SOS response is a response to DNA damage in which the cell cycle is arrested, and DNA repair and mutagenesis are induced. The response involves the RecA protein, which when stimulated by single-stranded DNA, is involved in the inactivation of the LexA repressor, thereby inducing the SOS response. Upon induction of DNA damage by a programmable nuclease reaching its target sequence (e.g., a mutated sequence or a sequence of a gene of interest), the cellular SOS response is activated. When the SOS response is activated in the presence of an SOS-responsive reporter construct, transcription of the reporter molecule is concomitantly activated.

Thus, in some embodiments, programmable nuclease circuits may be coupled with, for example, an SOS-responsive reporter construct to detect nucleic acid mutations associated with, for example, antibiotic resistance genes and/or virulence genes in bacterial cells (e.g., bacterial cell niches). In some embodiments, programmable nuclease circuits may be coupled with a reporter construct that responds to a signal resulting from DNA cleavage to detect other genes of interest and/or gene copy number. For example, a programmable nuclease circuit may be coupled with an SOS-responsive reporter construct.

In some embodiments, provided herein are methods of diagnosing a subject (e.g., a human subject) having bacteria that contain virulance factor and/or and antibiotic resistance gene. In some embodiments, the methods comprise administering to a subject (a) a delivery vehicle with at least one nucleic acid encoding an engineered autonomously distributed circuit that contains a programmable nuclease that targets a gene or nucleotide sequence of interest, and (b) a nucleic acid encoding an SOS-responsive reporter construct.

Also contemplated herein, in some embodiments, is the use of programmable nuclease circuits to sculpt the composition of bacterial populations (e.g., complex bacterial populations). For example, programmable nuclease circuits may be used to selectively remove bacteria with specific genomic contents, such as, for example, antibiotic resistance loci and/or virulence loci and/or metabolic pathways. Selective removal of such targeted loci can be achieved without affecting neighboring cells that do not contain the targeted loci. Thus, in some embodiments, programmable nuclease circuits are used to selectively knockdown bacteria that contain target DNA sequences while allowing the remaining non-target bacteria to dominate the population. By pairing RGNs with broad-host-range phages or conjugative plasmids (Westwater, C. et al. *Microbiology* 148, 943-50 (2002); Filutowicz, M. et al. *Plasmid* 60, 38-44 (2008)), targeted 'bacterial knockdown,' in some embodiments, may be used to selectively remove virulence genes and/or antibiotic resistance genes in pathogenic and/or commensal bacterial populations, enable functional studies of complex microbiota, and/or complement additive therapies, such as probiotics, for microbiome-associated disease by, for example, clearing specific niches and/or removing defined genes from bacterial populations.

Compositions and Kits

Also provided herein are compositions and kits that comprise any one or more of the phagemids, bacteriophages, probiotic bacterial cells, nucleic acids and/or libraries of the present disclosure. The compositions and kits may further comprise additional reagents such as buffers, salts and the like. In some embodiments, the compositions are pharmaceutical compositions optionally comprising one or more pharmaceutical carriers and/or excipients.

EXAMPLES

As used herein, for simplicity, engineered autonomously distributed circuits that contain a programmable nuclease of the present disclosure will be referred to as "programmable nuclease circuits." A programmable nuclease circuit of the present disclosure may express an RNA-guided nuclease (RGN) ("programmable RGN circuit"), a TAL effector nuclease (TALEN) ("programmable TALEN circuit"), or a zinc finger nuclease (ZFN) ("programmable ZFN circuit").

By packaging programmable nuclease circuits into non-lytic bacteriophage particles or harnessing mobilizable plasmids for high-efficiency delivery, conditional-lethality devices with high specificity, modularity, and multiplexability against undesired DNA sequences can be implemented, in some embodiments (FIG. 1).

Example 1: RNA-Guided Nucleases Mediate Sequence-Specific Cellular Cytotoxicity

Figure 2:
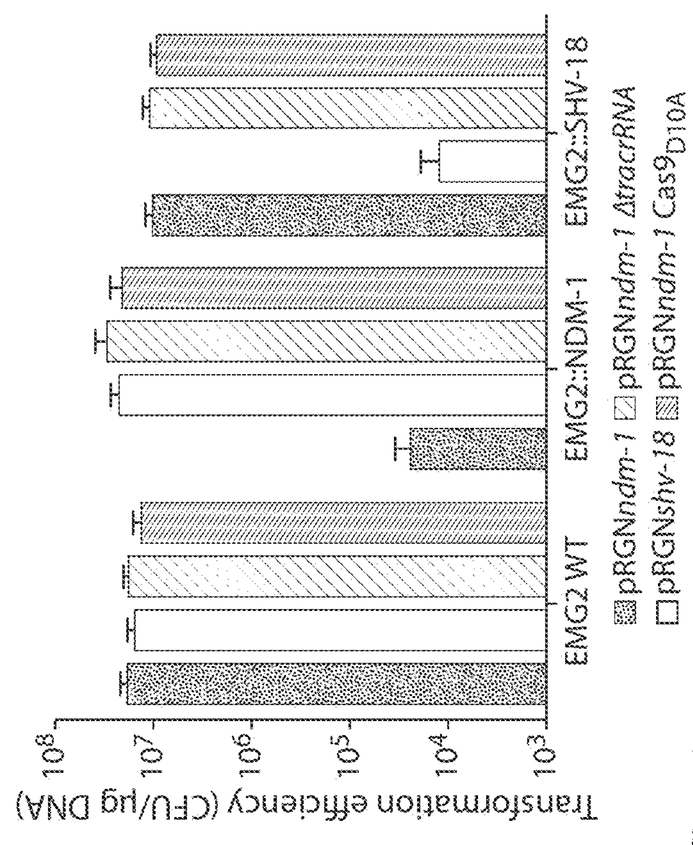
FIG. 2 shows a schematic design (left) and graph of transformation efficiency validation (right) of programmable RGN constructs. Plasmids pRGNndm-1 (black bars), pRGNshv-18 (white bars), pRGNndm-1 ΔtracrRNA (light gray bars), and pRGNndm-1 $Cas9_{D10A}$ (dark gray bars) were transformed into competent wild-type EMG2 (EMG2 WT) as well as otherwise isogenic strains containing chromosomally integrated $bla_{NDM-1}$ (EMG2::NDM-1) or $bla_{SHV-18}$ (EMG2::SHV-18). Transformants were enumerated on selective media to determine transformation efficiencies, which demonstrated the specific incompatibility of an RGN construct and its cognate protospacer (n=4).
Figure 2:
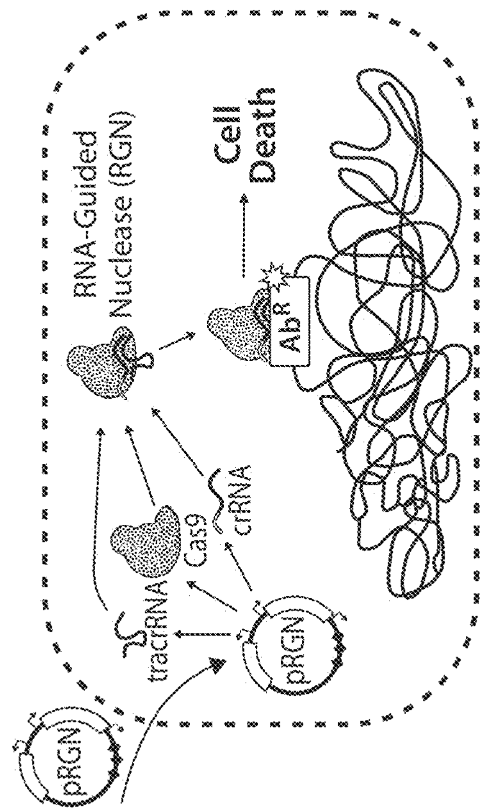

To establish RNA-guided nuclease (RGN) functionality in mediating sequence-specific cytotoxicity, programmable nuclease circuits were designed to induce double-stranded breaks in $bla_{SHV-18}$ or $bla_{NDM-1}$, which encode extended spectrum and pan-resistance to β-lactam antibiotics, respectively (Table 1) (Rasheed, J. K. et al. *Antimicrob. Agents Chemother.* 44, 2382-8 (2000); Rasheed, J. K et al. *Emerg. Infect. Dis.* 19, 870-8 (2013)). Transformation of plasmid-borne RGNs (pRGNs) into *E. coli* containing a chromosomal copy of these target genes resulted in nearly a thousand-fold decrease in transformation efficiency as compared to wild-type cells lacking the target (FIG. 2). Transformation efficiency was calculated using the following formula:

$$\text{Transformation Efficiency} = \frac{cfu/\text{mL}}{\mu g\ DNA\ \text{transformed}}$$

Figure 20A:
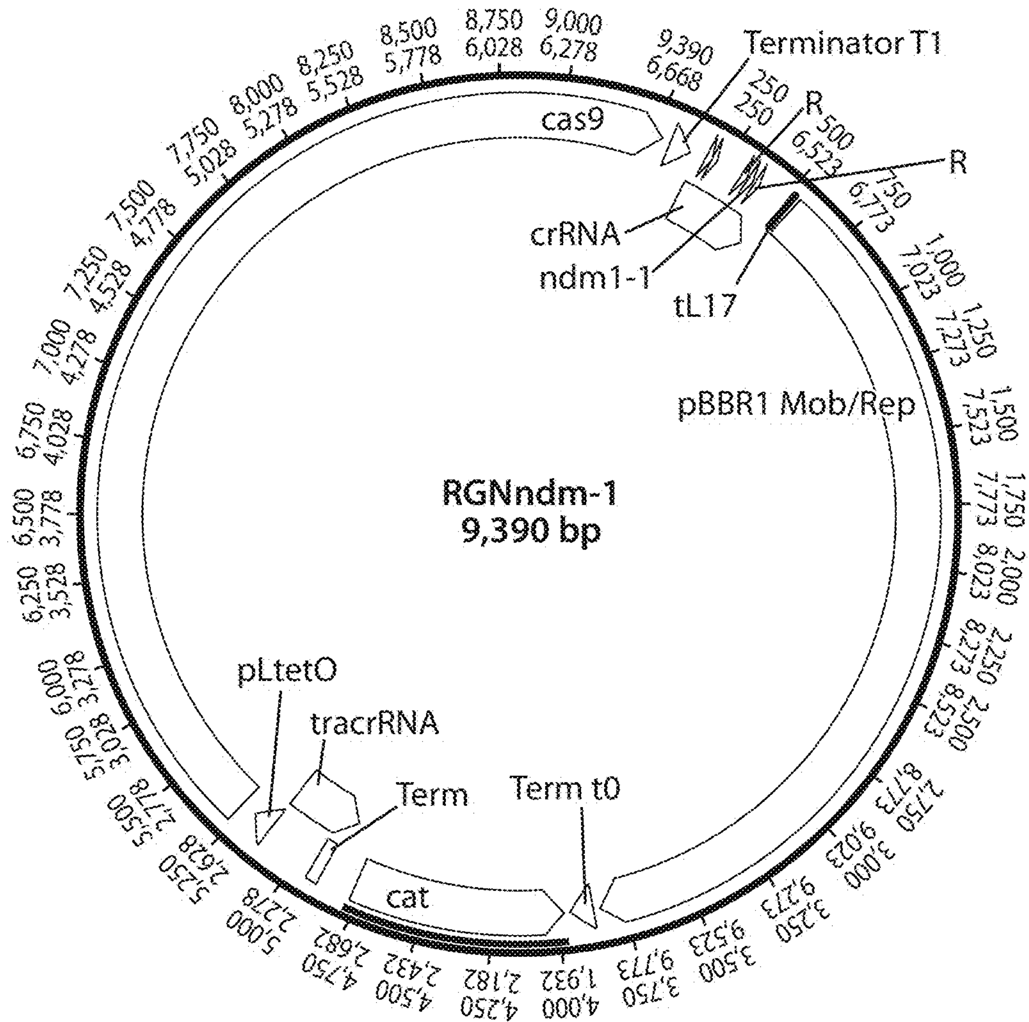
FIG. 20A shows a vector map of an example of a programmable RNA-guided nuclease (RGN) circuit targeting the beta-lactamase gene, $bla_{NDM-1}$, which confers broad resistance to beta-lactam antibiotics, including carbapenems.

FIG. 20A illustrates a vector map of an example of a programmable nuclease circuit targeting the beta-lactamase gene, $bla_{NDM-1}$. These results corroborate the mutual exclusivity between CRISPR-Cas and a cognate locus (Bikard, D. et al. *Cell Host Microbe* 12, 177-86 (2012); Gomaa, A. A. et al. *MBio* 5, (2013)).

TABLE 1

| Minimum Inhibitory Concentration (MIC) (μg/mL) | | | | | | | |
|---|---|---|---|---|---|---|---|
| Strain | AMP | CAZ | CTX | IPM | OFX | CIP | GEN |
| EMG2 Wild-Type | 2 | 0.25 | ≤0.0625 | 0.25 | 0.125 | ≤0.03125 | 4 |
| EMG2 $gyrA_{D87G}$ | 4 | 0.25 | ≤0.0625 | 0.25 | 0.5 | 0.125 | 4 |
| EMG2 pNDM-1 | >64 | >64 | >64 | 32 | 0.125 | ≤0.03125 | >64 |
| EMG2 pSHV-18 | 64 | 1 | 0.25 | 0.25 | 0.125 | ≤0.03125 | >64 |

Figure 3:
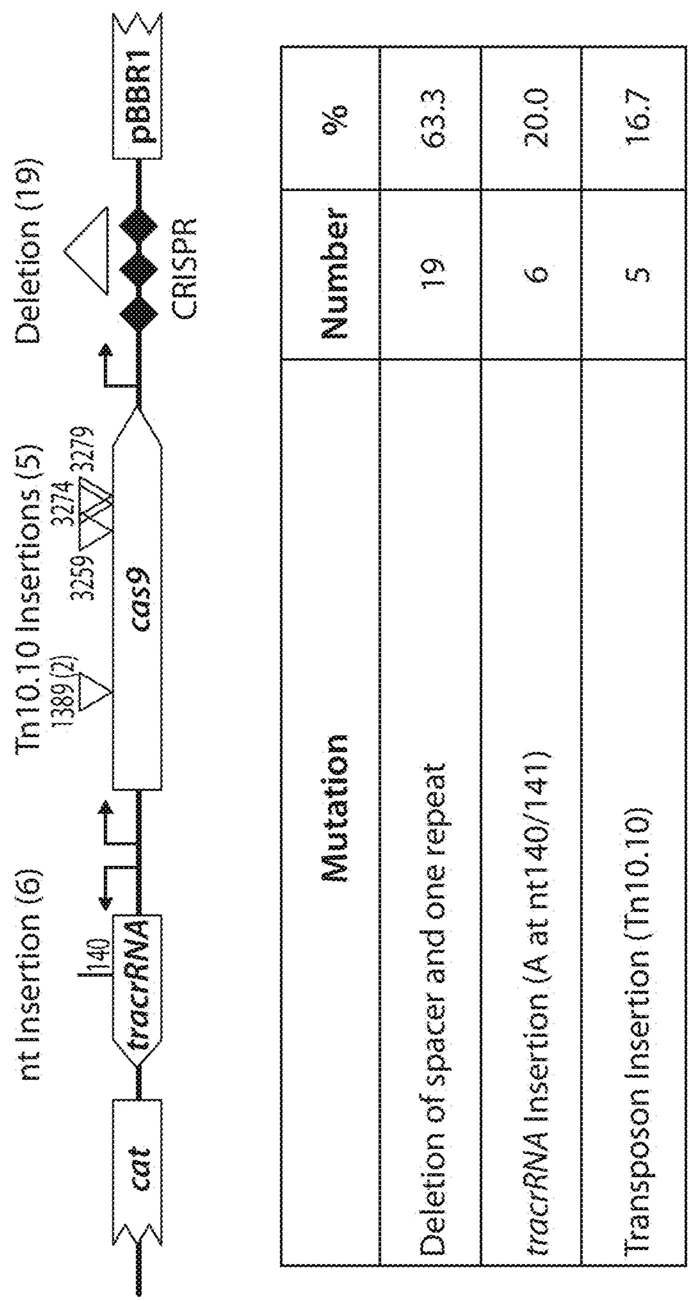
FIG. 3 shows a characterization of escape mutants that tolerated transformation of a cytotoxic RGN construct. EMG2::NDM-1 or EMG2::SHV-18 colonies that tolerated transformation of the pRGNndm-1 or pRGNshv-18 plasmids (FIG. 4) were re-isolated and sequenced to identify escape mutations. Spacer deletion in the CRISPR locus, point mutations in tracrRNA, and transposon insertions in cas9 led to RGN inactivation in successful transformants. Five escape mutants from three independent experiments were sequenced per strain (n=30).

AMP = ampicillin;
CAZ = ceftazidime;
CTX = cefotaxime;
IPM = imipenem;
OFX = ofloxacin;
CIP = ciprofloxacin;
GEN = gentamicin Sequence analysis of 30 escape mutants, cells that received an RGN plasmid despite the presence of a target sequence, revealed that tolerance was exclusively due to a defective construct, frequently resulting from deletion of the targeting spacer within the crRNA locus (FIG. 3). Furthermore, deletion of the tracrRNA as well as inactivation of the nuclease domain of Cas9 ($Cas9_{D10A}$) abrogated the loss of transformation efficiency in cells that harbored a target sequence. Thus, a catalytically active endonuclease (e.g., Cas9), tracrRNA, and crRNA (also referred to as guide RNA (gRNA)) are necessary and sufficient to mediate sequence-specific cytotoxicity in *E. coli* (FIG. 1).

Figure 21:
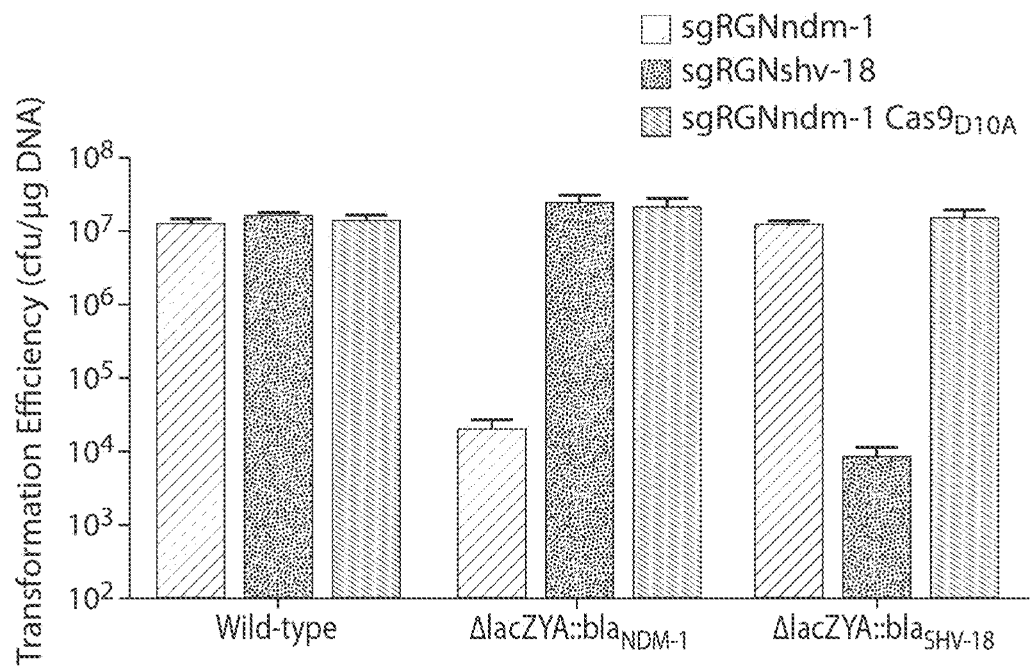
FIG. 21 shows a graph of the transformation efficiency of cells that contain single-guide RGNs and the cognate target sequence. Only a catalytically active Cas9 and cognate crRNA are necessary and sufficient to mediate RGN-mediated killing using the single guide-RNA system.

Similarly, introduction of single-guide RGNs (ssRGN), utilizing a single hybrid/chimeric gRNA in place of the natural crRNA and required tracrRNA adaptor (Jinek, M. et al. Science 337, 816-21 (2012)), demonstrated similar reductions in transformation efficiency when introduced into cells containing the cognate target sequence (FIG. 21). Only a catalytically active endonuclease and cognate crRNA are necessary and sufficient to mediate RGN-mediated killing using the single guide-RNA system.

Example 2: RNA-Guided Nucleases are Effective Against High-Copy-Number Plasmids

Figure 4:
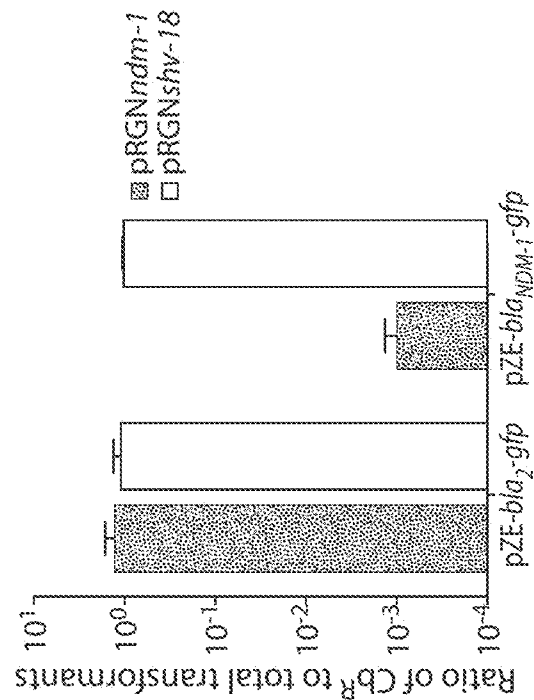
FIG. 4 shows a schematic design (left) and graph of carbenicillin resistance validation (right) of programmable RGN constructs. Plasmids pRGNndm-1 (black bars) and pRGNshv-18 (white bars) were transformed into EMG2 cells containing either pZE-$bla_{NDM-1}$-gfp or pZE-$bla_{Z}$-gfp plasmids. Transformants, first selected in appropriate antibiotic media, were enumerated on LB+chloramphenicol (Cm) or LB+Cm+carbenicillin (Cb) agar to calculate the ratio of transformants retaining Cb resistance to total transformants (n=9). Error bars indicate s.e.m. of at least four independent biological replicates.
Figure 4:
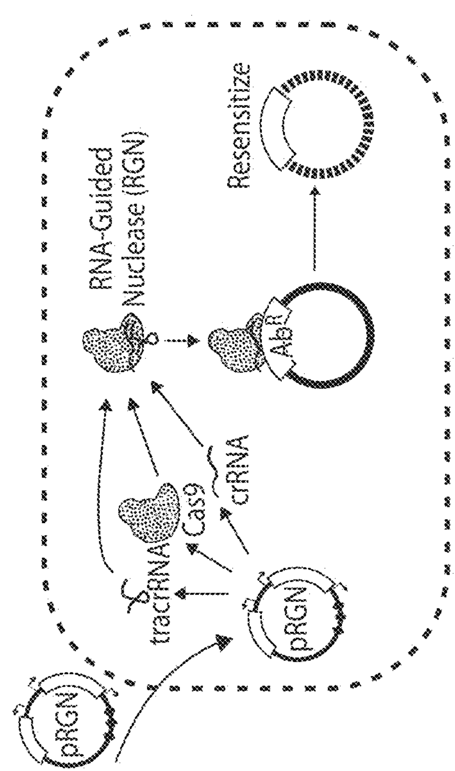
Figure 5:
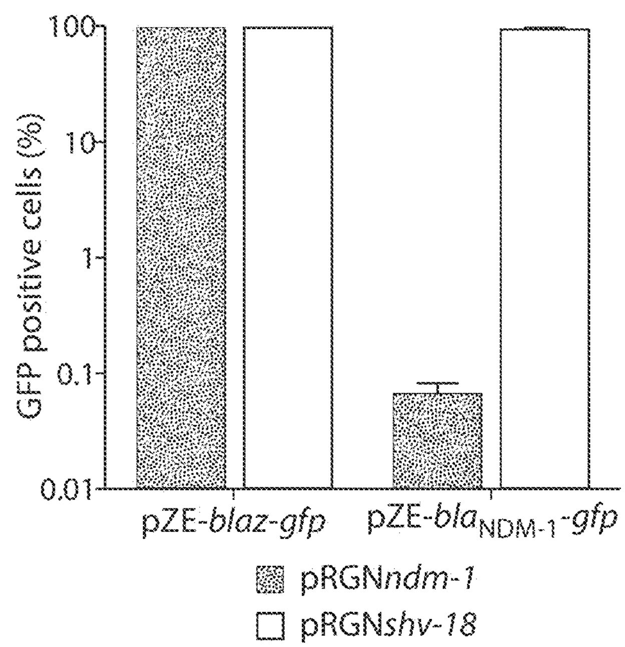
FIG. 5 shows a graph showing that loss of a high-copy GFP-expressing plasmid in cells transformed with pRGNndm-1 leads, as evidenced by flow cytometry. EMG2 cells containing either pZE-$bla_{Z}$-gfp or pZE-$bla_{NDM-1}$-gfp plasmids were transformed with pRGNndm-1 (black bars) or pRGNshv-18 (white bars) plasmids and transformants were selected overnight in LB+Cm. Plasmid loss was determined by calculating the percentage of GFP positive cells following gating by forward and side scatter. Error bars indicate s.e.m. of measurements from three independent experiments, each with three biological replicates (n=9).

Antibiotic resistance genes, such as $bla_{SHV-18}$ and $bla_{NDM-1}$, often reside on large, multi-copy plasmids capable of autonomous transfer in microbial populations, leading to horizontal dissemination of drug resistance (Nordmann, P. et al. *Trends Mol. Med.* 18, 263-72 (2012)). RGN activity against high-copy plasmids was verified with a GFP-expressing, ColE1-derived vector containing a standard β-lactamase selectable marker (pZE-$bla_Z$-gfp) (Lutz, R. & Bujard, H. *Nucleic Acids Res.* 25, 1203-10 (1997)) or $bla_{NDM-1}$ (pZE-$bla_{NDM-1}$-gfp). Vectors bearing this ColE1 origin are present at copy numbers of 50-70 per cell (Lutz, R. & Bujard, H., 1997). Transformation of pRGNndm-1, a plasmid-borne RGN targeting $bla_{NDM-1}$, into cells containing pZE-$bla_{NDM-1}$-gfp led to a three-log reduction in carbenicillin-resistant transformants, whereas transformation of pRGNndm-1 into cells containing target-free pZE-$bla_Z$-gfp did not lead to any significant reduction in resistant transformants (FIG. 4). Similarly, transformation of pRGNndm-1 into cells possessing pZE-$bla_{NDM-1}$-gfp led to an approximately thousand-fold decrease in GFP-expressing cells, as measured by flow cytometry, but no significant decrease was found with transformation of pRGNndm-1 into cells possessing pZE-$bla_Z$-gfp (FIG. 5). The activity of programmable nuclease circuits is therefore sufficient to exclude even high-copy antibiotic resistance plasmids from cells and can re-sensitize an already resistant microbial population to antibiotics. This strategy could be used to control gene expression in synthetic gene circuits through the molecular deletion of plasmids from cells.

Figure 25:
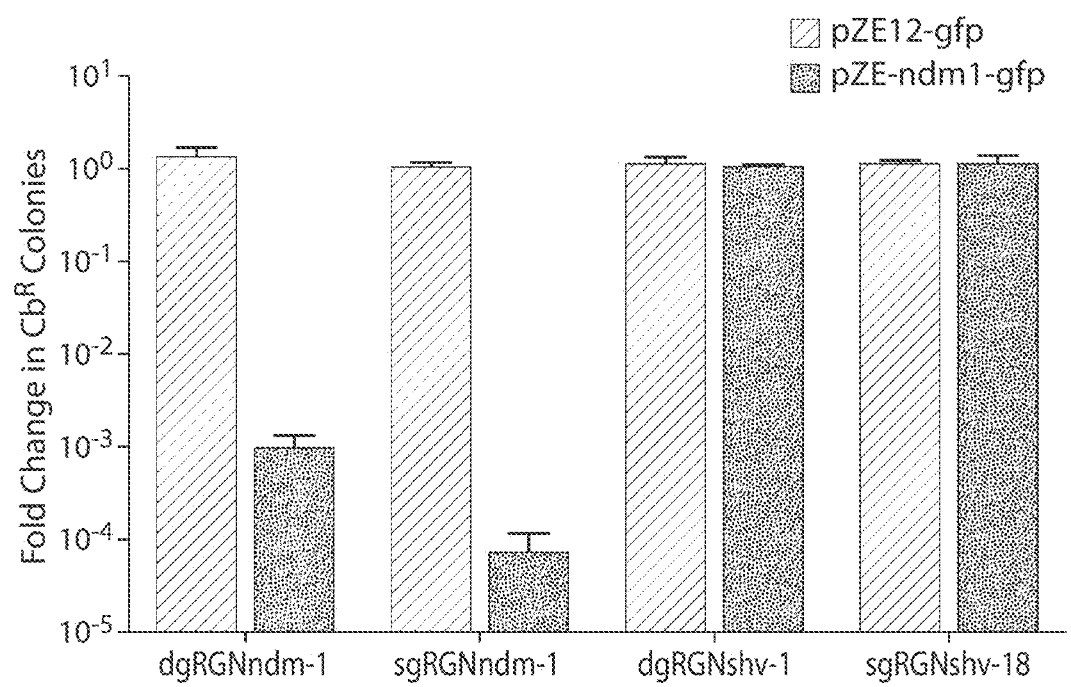
FIG. 25 shows a graph of the fold change in carbenicillin resistant colonies of bacterial cells containing high copy plasmids (ColE1-derived) that contained either the bla or $bla_{NDM-1}$ gene as the resistance marker (named pZE12-gfp and pZE-ndm1-gfp, respectively) and single or dual-guide RGNs targeting $bla_{NDM-1}$ or $bla_{SHV-18}$.

Further, because many antibiotic resistance genes are encoded on episomes, whether programmable nuclease circuits can induce plasmid loss in *Escherichia coli* (*E. coli*) was explored. Wild-type EMG2 cells were first transformed with high copy plasmids (ColE1-derived) that contained either the bla or $bla_{NDM-1}$ gene as the resistance marker (named pZE12-gfp and pZE-ndm1-gfp, respectively). These plasmid-containing cells were made chemically competent using a TSS protocol, and transformed with single (Cas9 and hybrid/chimeric gRNA) or dual-guide (Cas9, tracrRNA, and crRNA) RGNs targeting $bla_{NDM}$-1 or $bla_{SHV-18}$. Following a 90 minute recovery in SOC, cultures were diluted 1:100 in fresh LB chloramphenicol to select for transformants and incubated for 16 hours until saturation. The samples were plated on LB plates supplemented with chloramphenicol and carbenicillin or with chloramphenicol only. Introduction of a cognate RGN into cells bearing a $bla_{NDM-1}$ containing plasmid induced potent loss of plasmid as measured by the ratio of carbenicillin resistant to total number of colonies (FIG. 25). Thus, in addition to toxicity with chromosomal targets, programmable dual-guide and single-guide RGN circuits can induce plasmid loss of episomal targets.

Figure 6:
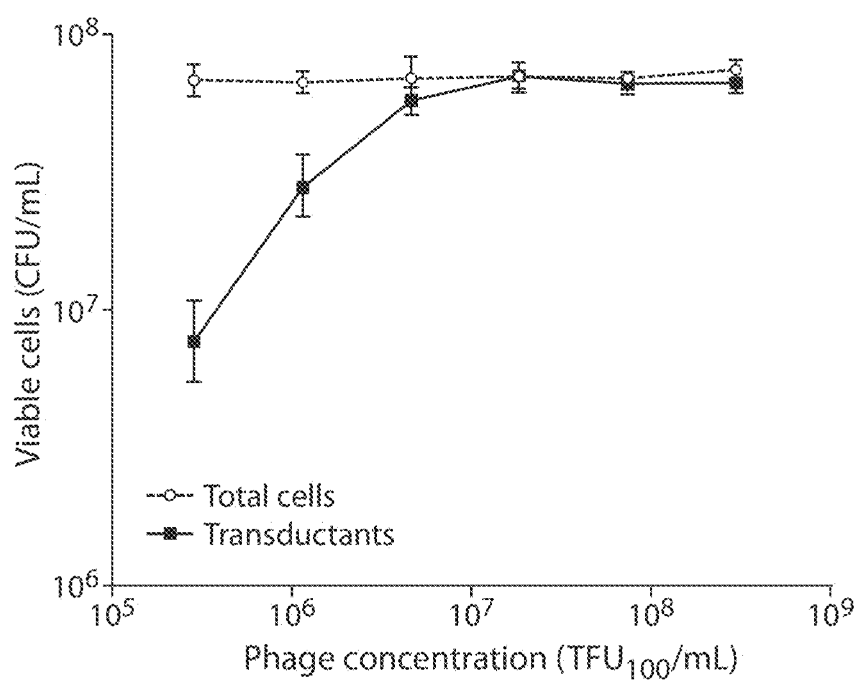
FIG. 6 shows titrating delivery of ΦRGNndm-1. Approximately $6.5\times10^6$ CFU/mL of EMG2 wild-type cells were incubated with dilutions of ΦRGNndm-1 phagemid for 2 hours and plated onto LB (circles) and LB+kanamycin (Km) (squares) to determine the highest dilution of the purified ΦRGN stock able to transduce approximately 100% of the recipient cell population (defined as $TFU_{100}$/mL). Error bars indicate s.e.m. of three independent experiments (n=3).
Figure 7:
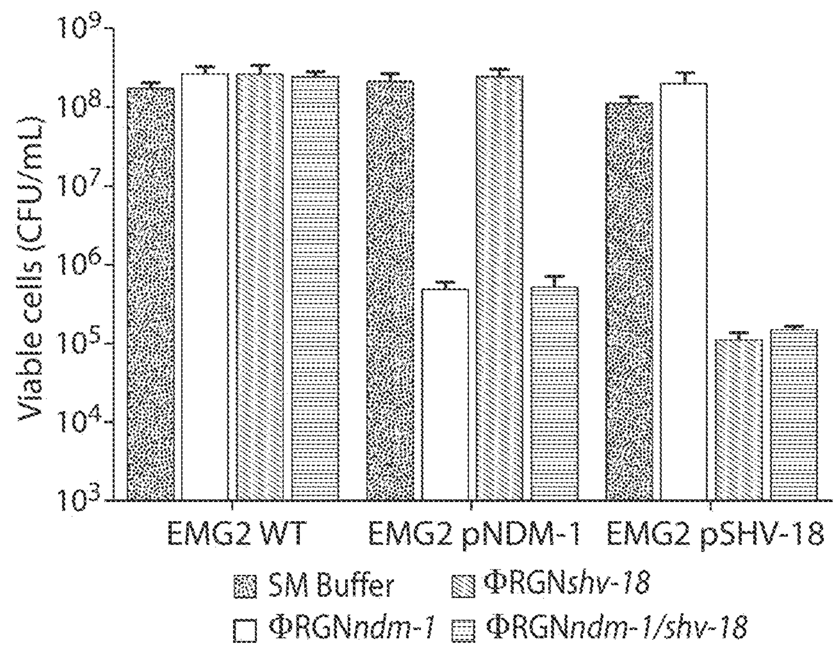
FIG. 7 shows treatment of EMG2 WT or EMG2 containing native resistance plasmids, pNDM-1 (encoding $bla_{NDM-1}$) or pSHV-18 (encoding $bla_{SHV-18}$), with SM buffer (black bars), ΦRGNndm-1 (white bars), ΦRGNshv-18 (light gray bars), or multiplexed ΦRGNndm-1/shv-18 (dark gray bars) at a multiplicity of infection (MOI) ~20 showed sequence-dependent cytotoxicity as evidenced by a strain-specific reduction in viable cell counts.

Example 3: RNA-Guided Nucleases are Delivered with High Efficiency to Bacterial Cells The viability of programmable nuclease circuits as an antimicrobial therapy hinges, in some instances, on high-efficiency delivery of genetic constructs to bacterial cells. Bacteriophages are natural predators of prokaryotes and are highly adept at injecting DNA into host cells. To use phage particles for programmable nuclease circuit delivery, phagemid vectors were engineered by pairing the $bla_{NDM-1}$ or $bla_{SHV-18}$ RGN constructs with an f1 origin for packaging into M13 particles. Phage-packaged RGNndm-1 ("ΦRGNndm-1") was capable of comprehensively transducing a population of *E. coli* EMG2 (FIG. 6). Treatment of EMG2 housing native plasmids conjugated from clinical isolates containing $bla_{NDM-1}$ (pNDM-1) or $bla_{SHV-18}$ (pSHV-18) with the cognate ΦRGNs resulted in 2-3-log reductions in viable cells even in the absence of any selection (FIG. 7). Furthermore, programmable nuclease circuits engendered no toxicity against wild-type EMG2 or EMG2 containing non-cognate plasmids (FIG. 7).

Figure 22:
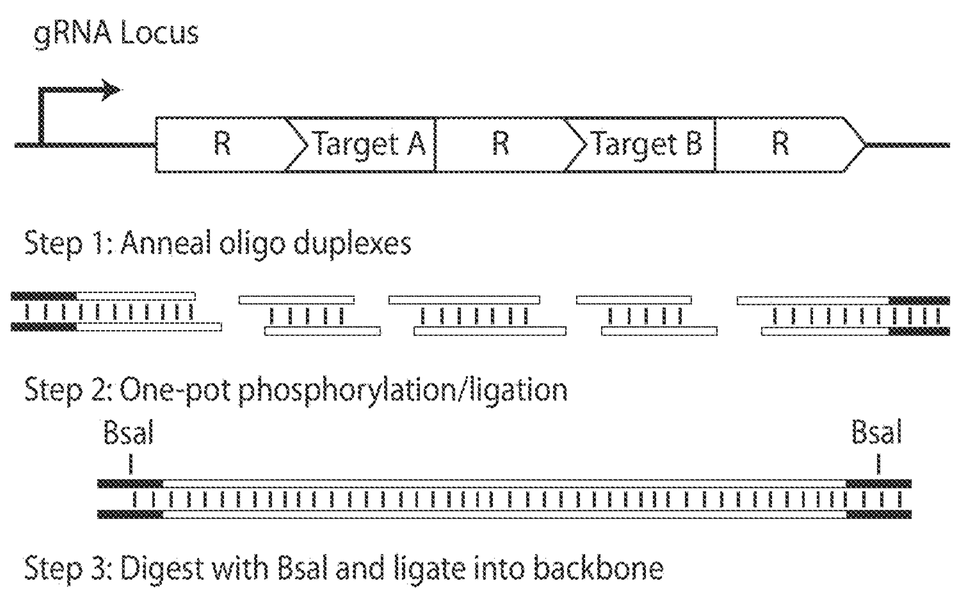
FIG. 22 shows an oligo-based assembly strategy of the present disclosure for multiplexed gRNAs, which enables straightforward construction of multiple gRNAs within a single expression cassette. "R" represents the repeats in the CRISPR locus.

CRISPR-Cas antimicrobials can be multiplexed to target multiple different genetic loci. To mitigate the occurrence of variants that may arise due to modifications of gene target sequences or programmable nuclease circuits, for example, multiplexed programmable nuclease circuits may be designed to target genes at multiple protospacers such that target inactivation is mediated by more than one guide RNA (gRNA). Natural CRISPR loci can contain up to 58 spacers to simultaneously license Cas9 to induce double stranded breaks at 58 different DNA sequences (Gunderson, F. F., et al. *mBio* 4(2): 1-11 (2013)). Thus, engineered CRISPR loci can target multiple genes to create multi-functional, highly selective antimicrobial devices. Herein, an efficient one-step DNA assembly strategy was created to redirect the CRISPR-Cas system against multiple heterologous targets (e.g., Target A, Target B, etc.) with only short, inexpensive, DNA oligonucleotides (FIG. 22). For example, multiple double-stranded oligonucleotides (referred to as "oligo duplexes" can be annealed, phosphorylated/ligated, and then digested and inserted into a vector backbone (FIG. 22). In some embodiments, multiplexed programmable nuclease circuits may exhibit greater selective pressure against plasmid-borne genes and greater cytotoxicity against cells with chromosomal genes of interest. In some embodiments, programmable nuclease circuits that simultaneously target multiple different antibiotic-resistance genes and virulence genes may be created (e.g., targeting two, three, four or five different targets).

Figure 20B:
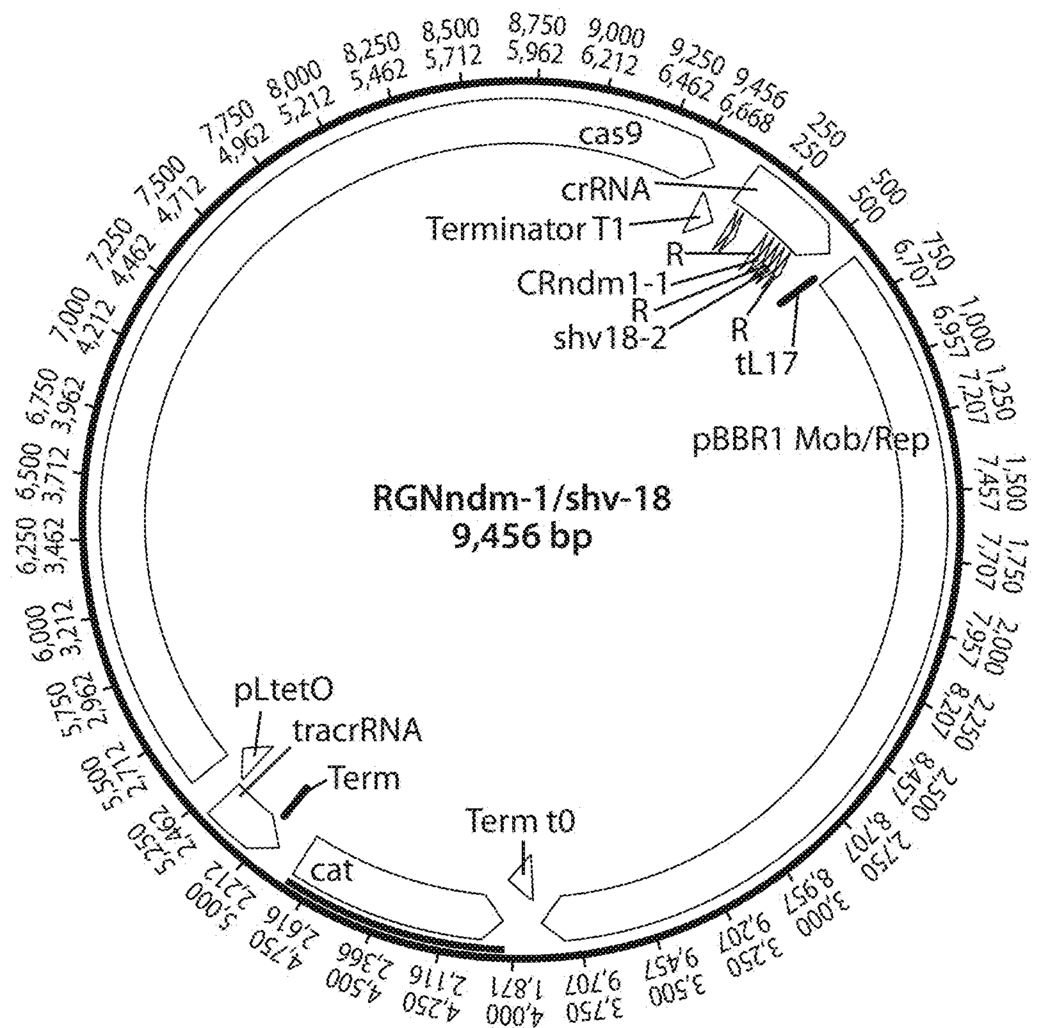
FIG. 20B shows a vector map of an example of a programmable RNA-guided nuclease (RGN) circuit targeting $bla_{NDM-1}$ and $bla_{SHV-18}$.

In order to exact multiplexed targeting by a single construct, an programmable nuclease circuit was engineered to contain spacers from both the $bla_{NDM-1}$- and $bla_{SVH-18}$-targeting RGNs (ΦRGNndm-1/shv-18). ΦRGNndm-1/shv-18 generated 2-3-log reductions in viable cells counts of both EMG2 pNDM-1 and EMG2 pSHV-18, but not of wild-type EMG2 (FIG. 7). FIG. 20B illustrates a vector map of an example of a programmable RGN circuit targeting $bla_{NDM-1}$ and $bla_{SHV-18}$. The plasmid, pRGNndm-1/shv-18, shown in FIG. 20B, contains nucleotide sequence encoding tracrRNA, Cas9 protein, crRNA targeting $bla_{NDM-1}$ and crRNA targeting $bla_{SHV-18}$.

Example 4: RNA-Guided Nucleases Detect Single Nucleotide Mutations

Figure 8:
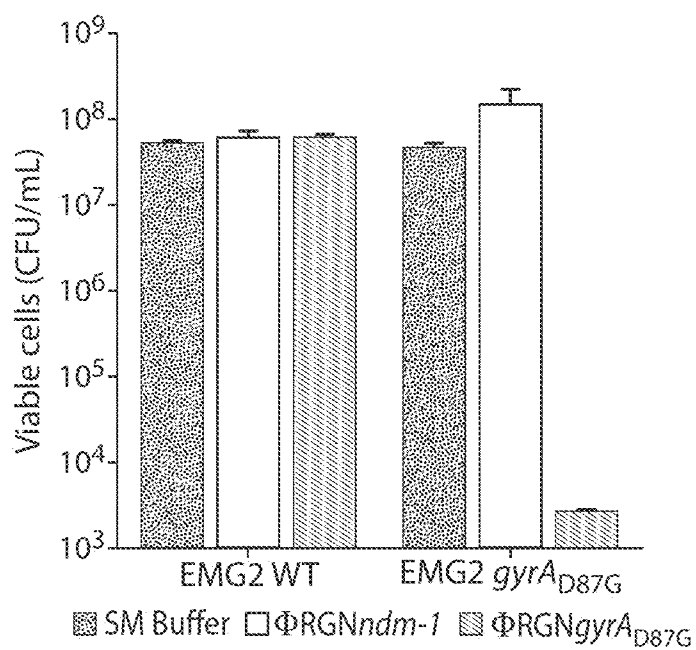
FIG. 8 shows a graph of a viable cell count. *E. coli* EMG2 WT or EMG2 $gyrA_{D87G}$ populations were treated with SM buffer (black bars), ΦRGNndm-1 (white bars), or $ΦRGNgyrA_{D87G}$ (gray bars) at MOI ~20, and viable cells were determined by plating onto LB agar. Error bars represent s.e.m. of three independent experiments (n=3).

In addition to antibiotic-modifying enzymes, such as β-lactamases, alterations in host proteins constitute a major antibiotic resistance mechanism (Jacoby, G. A. *Clin. Infect. Dis.* 41 Suppl 2, S120-6 (2005)). CRISPR-Cas systems show exquisite sequence specificity, where single base pair mutation in, or proximal to, the protospacer-adjacent motif (PAM) can fully abrogate activity. Due to the specificity of the CRISPR-Cas system in prokaryotes, it was suspected that programmable nuclease circuits could discriminate between susceptible and resistant strains that differ by a single nucleotide mutation in DNA gyrase (gyrA), which confers resistance to quinolone antibiotics (Table 1) (Jacoby, G. A. (2005)). Indeed, $ΦRGNgyrA_{D87G}$ exhibited specific cytotoxicity only towards quinolone-resistant *E. coli* harboring the $gyrA_{D87G}$ mutation and not towards otherwise isogenic strains with the wild-type gyrA gene (FIG. 8).

Figure 23:
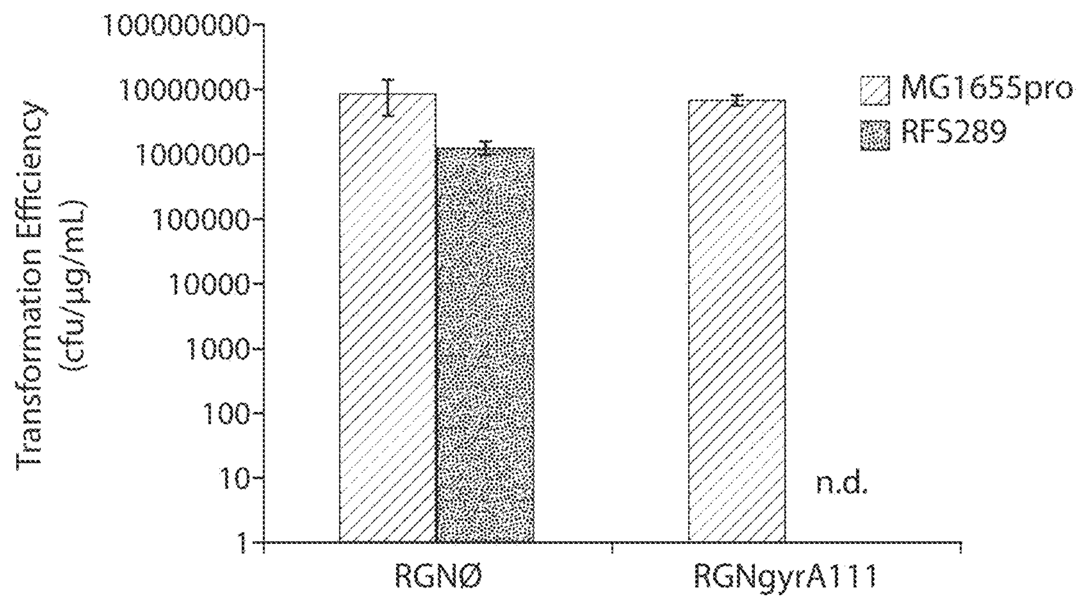
FIG. 23 shows a graph of data demonstrating that RGNs can detect single nucleotide polymorphisms that confer antibiotic resistance in the *E. coli* genome.

To further exploit this sensitivity to detect small nucleotide polymorphisms (SNPs) in the *E. coli* genome that confer resistance to quinolones, a programmable RGN circuit was designed to specifically target the gyrA gene in the quinolone-resistant RFS289 *E. coli* strain, which contains a $gyr_{A111}$ mutation. RFS289 and a similar wild-type strain, MG1655pro, were transformed with either RGNØ or $RGNgyr_{A111}$, and the transformation efficiency of each strain was determined by counting colony forming units (cfu) of transformants following plating on LB chloramphenicol plates. $RGNgyr_{A111}$ was specifically toxic to RFS289, although the wild-type and mutant sequences differed by only a single base pair (FIG. 23). Based on these results and the selective toxicity of RGNs, the present disclosure contemplates the use of programmable nuclease circuits to identify SNPs in bacterial genomes.

Example 5: RNA-Guided Nucleases Mediate Rapid Killing of Target Cells

Figure 9:
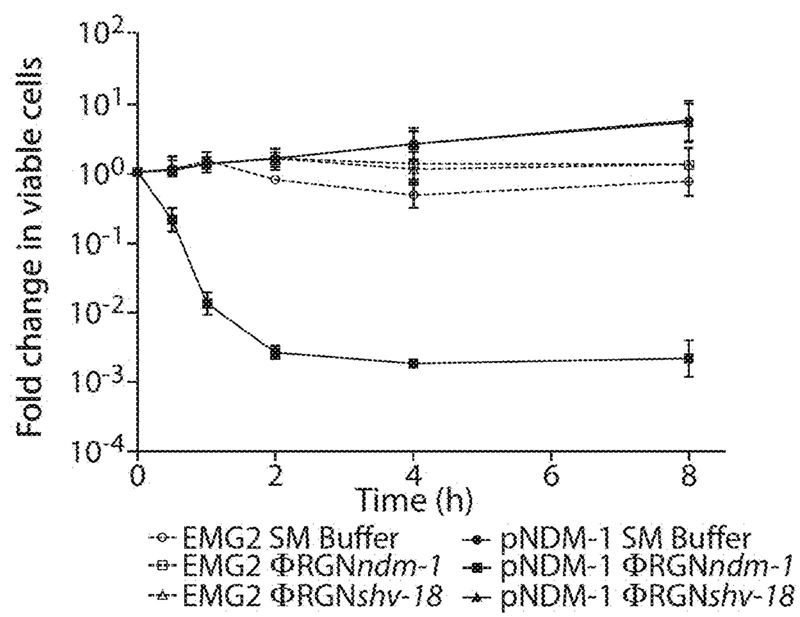
FIG. 9 shows a time-course treatment of EMG2 WT (dashed) or EMG2 pNDM-1 (solid) with SM buffer (circles), ΦRGNndm-1 (squares), or ΦRGNshv-18 (triangles) at MOI ~20. Data represent the fold change in viable colonies at indicated time points relative to time 0 hour.
Figure 10A:
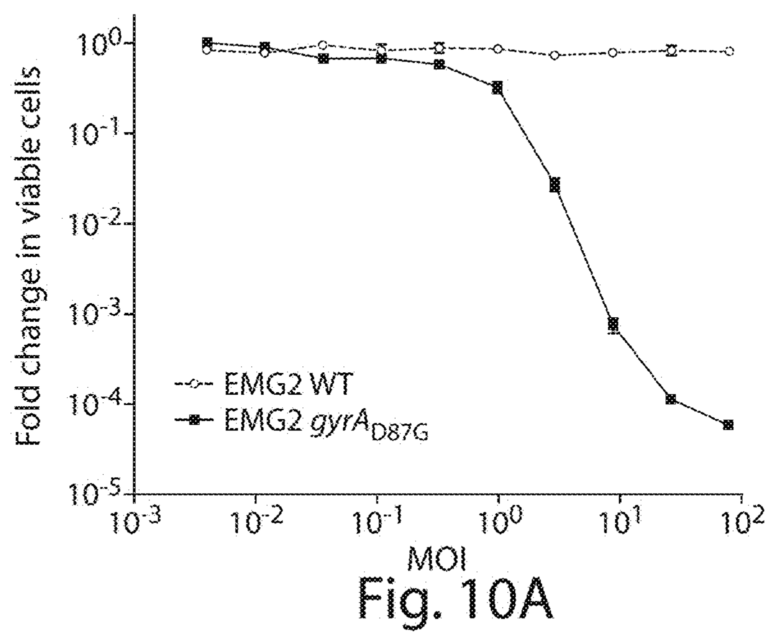
FIGS. 10A and 10B show a dose response of target cells to ΦRGNndm-1. Approximately $6.5\times10^6$ CFU/mL of EMG2 WT (circles) or EMG2 pNDM-1 (squares) cells were treated with increasing concentrations of ΦRGNndm-1 particles for two hours. Viable cells were determined by plating onto non-selective LB agar. ΦRGNndm-1 concentration was expressed as $TFU_{100}$/mL, which was defined as the bacterial concentration at which the highest dilution of phagemid can transduce approximately 100% of the population. Error bars indicate s.e.m. of three independent experiments (n=3).
Figure 10B:
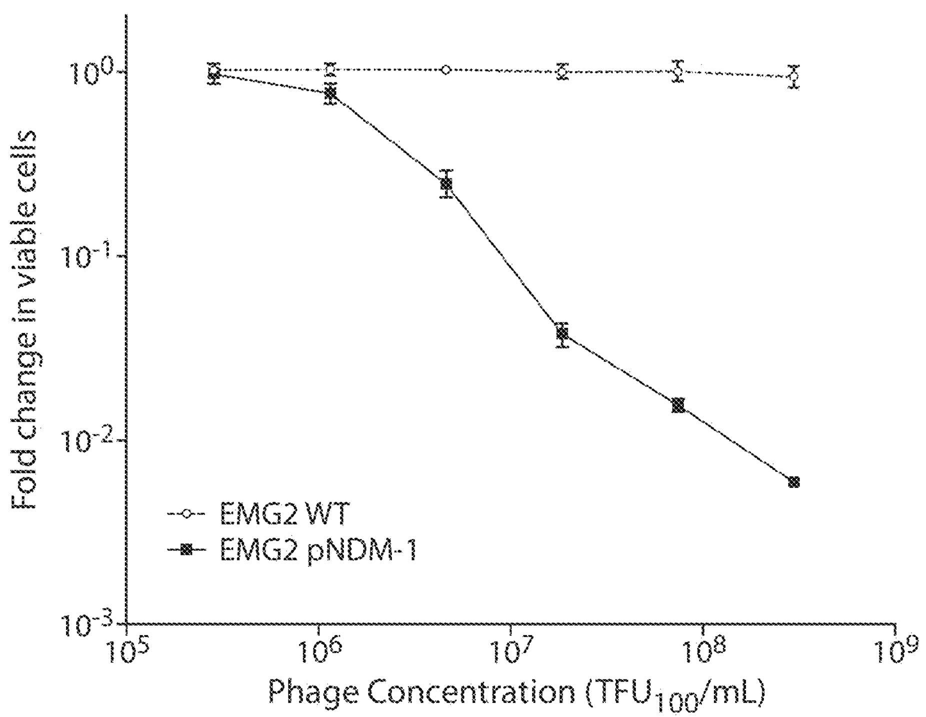

Killing curves revealed that ΦRGNs mediated rapid killing of target cells, with viable cell counts that decayed exponentially ($t_{1/2}$~13 minutes) and maximal bactericidal effect achieved by 2-4 hours (FIG. 9). Moreover, ΦRGN antimicrobial activity increased with phagemid particle concentration (FIGS. 10A and 10B).

Figure 11:
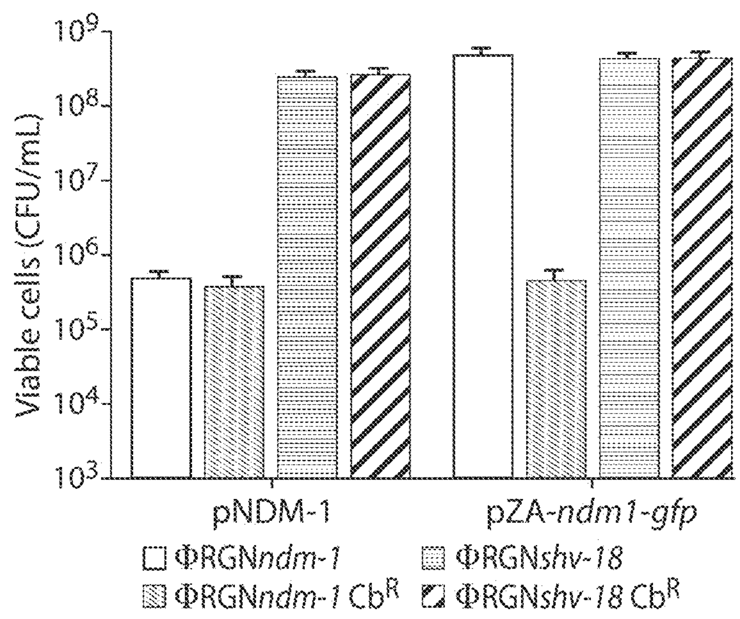
FIG. 11 shows a graph of viable cell counts. EMG2 *E. coli* containing the natural pNDM-1 plasmid or the $bla_{NDM-1}$ gene in a synthetic expression vector (pZA-ndm1-gfp) were treated with either ΦRGNndm-1 (white bars) or ΦRGNshv-18 (gray bars) at MOI ~20 and plated onto both non-selective LB (solid bars) and LB+carbenicillin (Cb) (hatched bars) to select for $bla_{NDM-1}$-containing cells. ΦRGNndm-1 treatment of cells harboring pNDM-1 resulted in a reduction in viability in the absence of selection, whereas ΦRGNndm-1 treatment of cells with pZA-ndm1-gfp demonstrated similar cytotoxicity only under selective pressure for plasmid maintenance (n=3).
Figure 12:
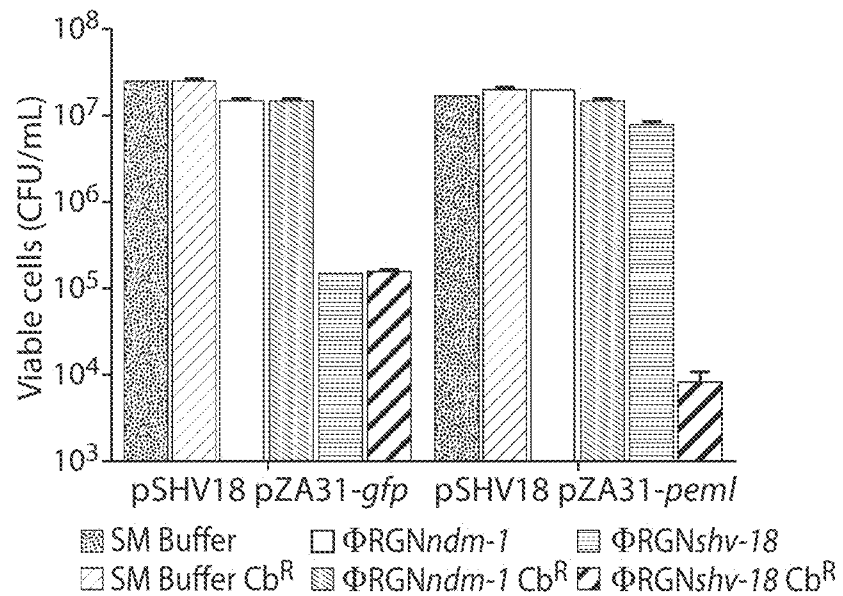
FIG. 12 shows a graph of viable cell counts. EMG2 pSHV-18 complemented with the cognate antitoxin(pZA31-pemI) or a control vector (pZA31-gfp) was treated with SM buffer (black bars), ΦRGNndm-1 (white bars), or ΦRGNshv-18 (gray bars). Cultures were plated on LB (solid bars) and LB+Cb (hatched bars) and colonies were enumerated to assess cytotoxicity or plasmid loss (n=3).

It was intriguing to observe that targeted cleavage of $bla_{NDM-1}$ in their native plasmids was lethal to host cells, whereas targeted cleavage of the same gene in a standard Lutz-based cloning vector ("pZA-ndm-1-gfp") was not (FIG. 11). Therefore, ΦRGN-induced plasmid loss in itself does not elicit lethality, but rather another component present in the native resistance plasmid must be responsible for this effect. It was hypothesized that targeting the native pNDM-1 and pSHV-18 plasmids with ΦRGNndm-1 and ΦRGNshv-18 caused cytotoxicity by artificially activating plasmid-borne toxin-antitoxin systems. Addiction modules are components of natural plasmids that ensure the persistence of these plasmids in bacterial populations by inducing death of daughter cells that fail to inherit episomes following cell division. These systems traditionally contain a labile antitoxin which quenches the lethal activity of a stable toxin, such that disruption of antitoxin production upon plasmid loss leads to de-repression of toxin activity and stasis or programmed cell death (Hayes, F. *Science* 301, 1496-9 (2003)). Analysis of the sequenced pSHV-18 plasmid revealed the presence of a unique toxin-antitoxin module, pemIK, which is commonly found among ESBL isolates (Mnif, B. et al. *J. Antimicrob. Chemother.* 65, 1599-603 (2010)). ΦRGNshv-18 treatment of EMG2 pSHV-18 complemented with the PemI antitoxin expressed in trans abrogated cytotoxicity and instead resulted in resensitization of this multidrug-resistant strain to a first-line β-lactam antibiotic (FIG. 12). Addiction modules can therefore dictate the outcome of ΦRGN activity on episomal targets, as their presence leads to cytotoxicity and their absence to plasmid loss.

Example 6: RNA-Guided Nucleases Target Intimin, a Virulence Factor of Enterohemorrhagic *Escherichia coli*

Figure 13:
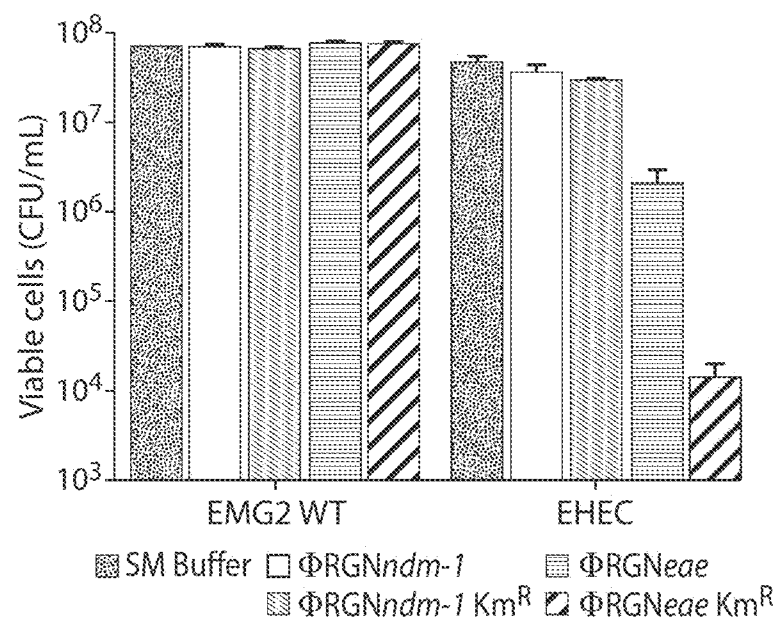
FIG. 13 shows a graph of viable cell counts. *E. coli* EMG2 WT cells or ATCC 43888 F' (EHEC) cells were treated with SM buffer (black bars), ΦRGNndm-1 (white bars), or ΦRGNeae (gray bars) at MOI~100 and plated onto LB agar (solid bars) to enumerate total cell number or LB+kanamycin (Km) (hatched bars) to select for transductants (n=3).
Figure 14A:
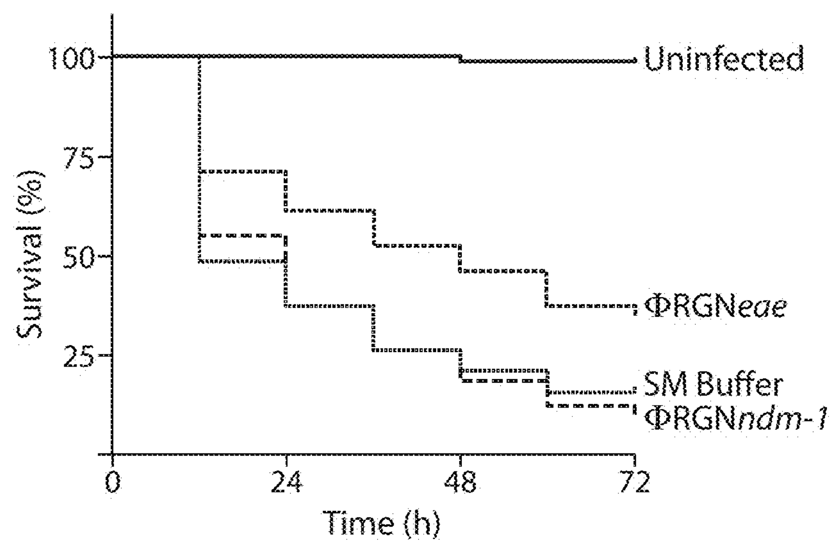
FIG. 14A shows a graph of survival curves. *Galleria mellonella* larvae were injected with either PBS (uninfected) or approximately $4\times10^5$ colony forming units (CFU) of EHEC. Subsequent administration of ΦRGNeae at MOI ~30 significantly improved survival compared to SM buffer or ΦRGNndm-1 treatment (Log-rank test, $p<0.001$). Survival curves represent an aggregate of four independent experiments, each with 20 worms per treatment group (n=80).
Figure 14B:
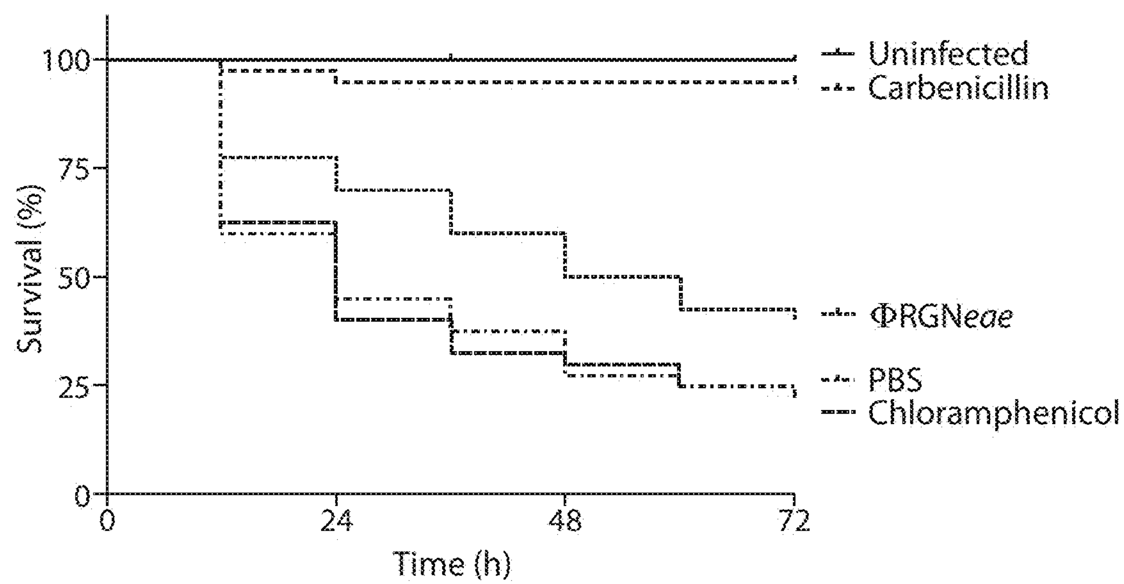
FIG. 14B shows a graph of survival curves, comparing ΦRGNeae to conventional antibiotic treatment of EHEC-infected *Galleria mellonella* larvae. *G. mellonella* larvae (n=40) were injected with PBS or approximately $3\times10^5$ colony forming units (CFU) of EHEC. Larvae were subsequently treated with PBS, ΦRGNeae at MOI ~30, chloramphenicol, or carbenicillin. The antibiotics were both applied at a concentration of 32 mg/kg, corresponding to the CLSI resistance breakpoints for Enterobacteriaceae (32 μg/mL). Administration of ΦRGNeae significantly improved survival compared to untreated and chloramphenicol treated larvae (Log-rank test, $p<0.05$).
Figure 15:
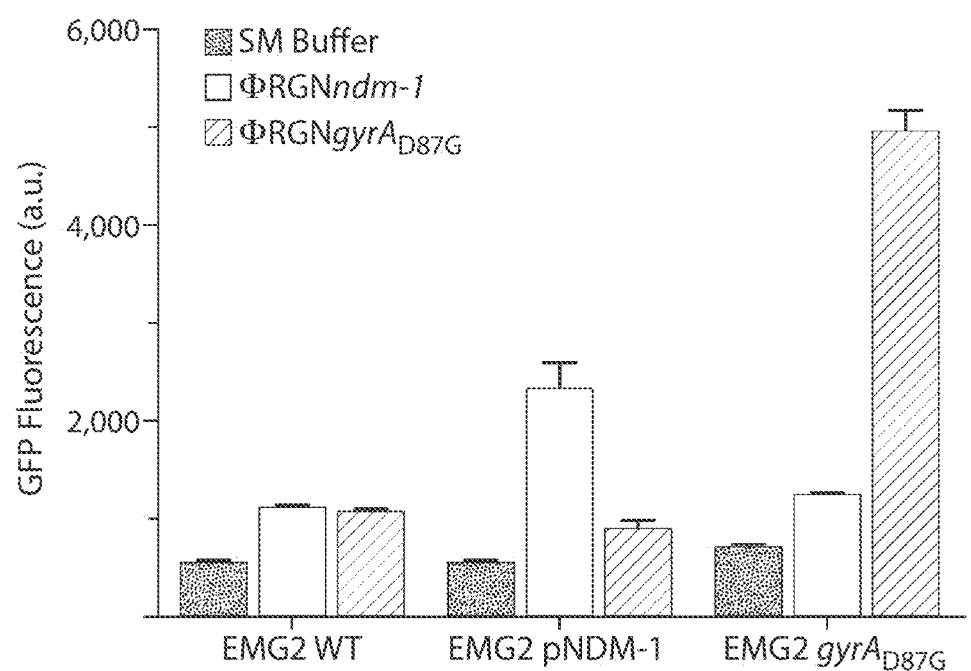
FIG. 15 shows a graph of GFP fluorescence. ΦRGN-induced DNA damage in cells that possess the cognate target sequence can be assayed with an SOS-responsive fluorescent reporter construct (pZA3LG) by flow cytometry (n=4). For all panels, error bars indicate s.e.m. of at least three biological replicates.
Figure 16A:
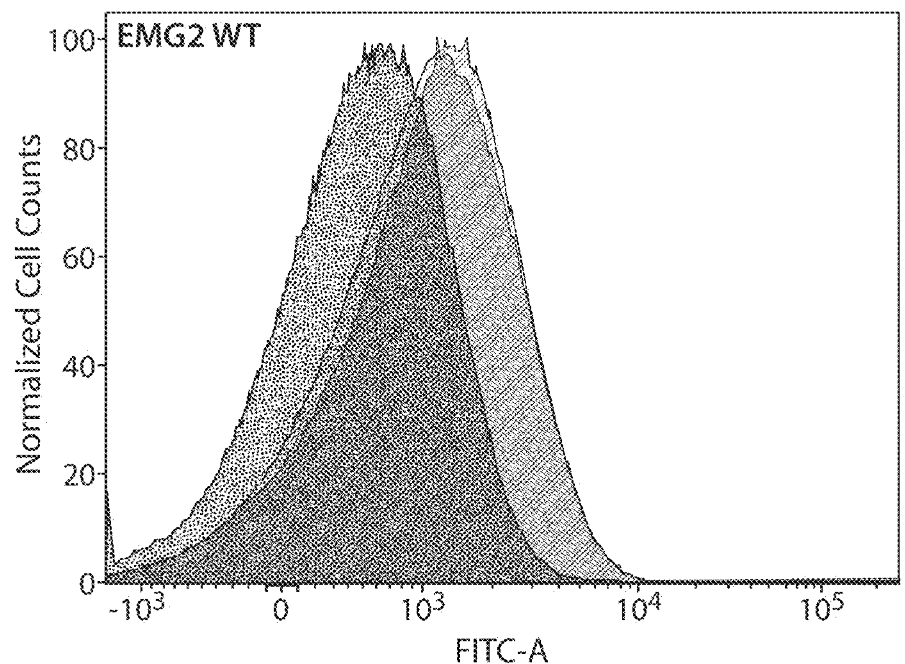
FIGS. 16A-16C show that treatment of *E. coli* with ΦRGNs induces DNA damage and an SOS response in cells that possess a cognate target sequence. EMG2 WT (FIG. 16A), EMG2 gyr$A_{D87G}$ (FIG. 16B), and EMG2 pNDM-1 (FIG. 16C) containing the pZA3LG reporter plasmid were treated with either SM buffer (16A:left curve; 16B:left curve; 16C:left curve), ΦRGNndm-1 (16A:right curve; 16B: middle curve; 16C: right curve), or ΦRGNgyr$A_{D87G}$ (16A: middle curve; 16B:right curve; 16C:middle curve). GFP expression on pZA3LG is under the control of the SOS-responsive PL(lexO) promoter. Injection of single-stranded phagemid DNA led to a mild induction of an SOS response, whereas RGN activity in cells which possess a cognate target sequence led to strong induction of SOS. Histograms were generated by combining data from four biological replicates and are normalized to the mode of the population.
Figure 16B:
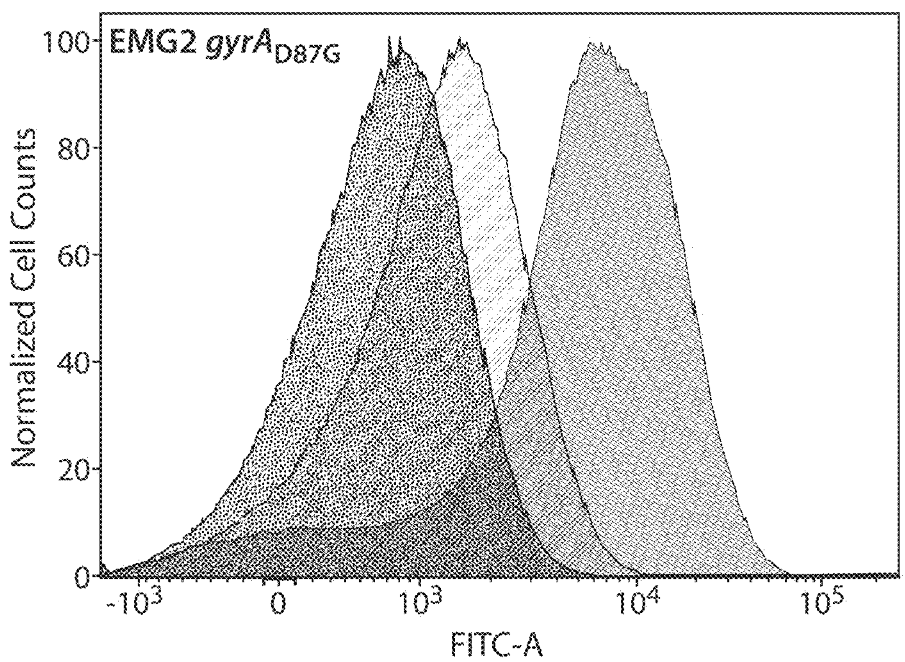
Figure 16C:
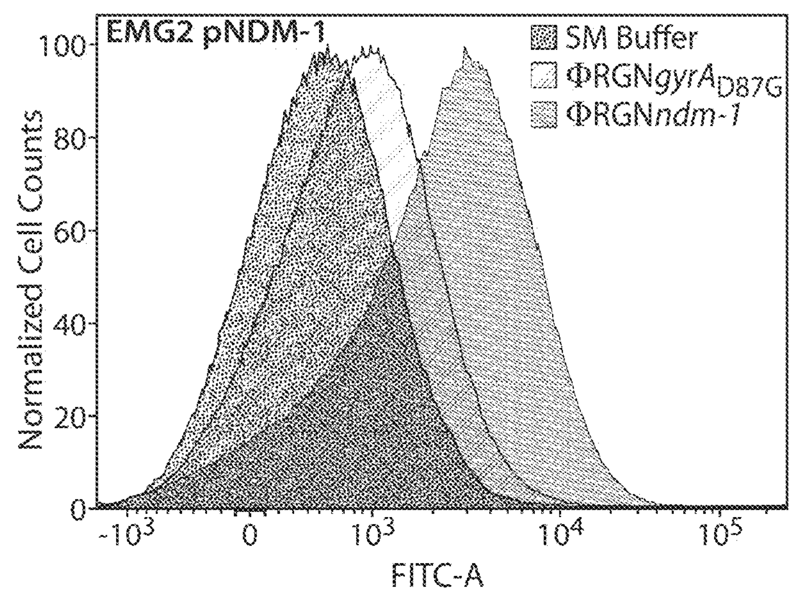

To further demonstrate the versatility of programmable nuclease circuits for specifically combating pathogens, a ΦRGN was designed to target intimin, a virulence factor of enterohemorrhagic *E. coli* O157:H7 (EHEC) necessary for intestinal colonization and pathology. Encoded by the eae gene, intimin is a cell-surface adhesin that mediates intimate attachment to the host epithelium, permitting subsequent disruption of intestinal tight junctions and effacement of microvilli (Kaper, J. B. et al. *Nat. Rev. Microbiol.* 2, 123-40 (2004)). Treatment of EHEC with ΦRGNeae resulted in a 20-fold reduction in viable cell counts; this cytotoxicity was increased an additional 100-fold under selection for ΦRGNeae transductants (FIG. 13). Furthermore, ΦRGN treatment was assessed in *Galleria mellonella* larvae, an infection model that has grown increasingly popular for providing virulence data predictive for higher-order mammals (Desbois, A. P. & Coote, P. J. *Adv. Appl. Microbiol.* 78, 25-53 (2012)). This model has also been used to evaluate antimicrobials including the antibiotics daptomycin, vancomycin, and penicillin against methicillin resistant *Staphylococcus aureus* (Desbois, A. P. & Coote, P. J. *J. Antimicrob. Chemother.* 66, 1785-90 (2011)) and various bacteriophages against the cystic fibrosis opportunist Burkholderia cenocepacia (Seed, K. D. & Dennis, J. J. *Antimicrob. Agents Chemother.* 53, 2205-8 (2009)), among others (Desbois, A. P. & Coote, P. J. (2012)). Administration of ΦRGNeae to EHEC-infected *G. mellonella* larvae significantly improved survival over no treatment or an off-target ΦRGN control (FIG. 14A). Moreover, ΦRGNeae was significantly more effective than chloramphenicol treatment, to which the EHEC strain was resistant (FIG. 14B). Though carbenicillin, to which the bacteria were susceptible, was superior to ΦRGNeae treatment (FIG. 14B), these data support RGNs as viable alternatives for cases where bacteria are highly resistant to existing antibiotics Improvements in delivery and killing efficiency with ΦRGNeae may further improve survival in the *G. mellonella* model. The in vivo efficacy of ΦRGNs points to its potential therapeutic capacity and suggests its utility as a sequence-specific antimicrobial.

Example 7: RNA-Guided Nucleases Induces DNA Damage and an SOS Response in Cells

Apart from their therapeutic potential, RGN activity can be coupled with a fluorescence reporter to assay the presence of target sequences in bacterial cultures. *E. coli* and other bacteria respond to chromosomal double-stranded breaks by inducing DNA repair through the activation of the SOS response (Pennington, J. M. & Rosenberg, S. M. *Nat Genet* 39, 797-802 (2007)). Using a SOS-responsive GFP reporter plasmid (Dwyer, D. J. et al. *Mol Syst Biol* 3, (2007)), a 8-fold and 4-fold increase in fluorescence was observed in cells containing a chromosomal (gyrAD87G) or plasmid-borne (blaNDM-1) target site, respectively, when treated with their cognate ΦRGNs relative to untreated cells (FIG. 15 and FIGS. 16A-16C). These results both confirm that programmable nuclease circuits can induce DNA damage in target cells and can be coupled with SOS-based reporters to detect specific genes or sequences, even at the single-nucleotide level, for diagnostic purposes.

Figure 17:
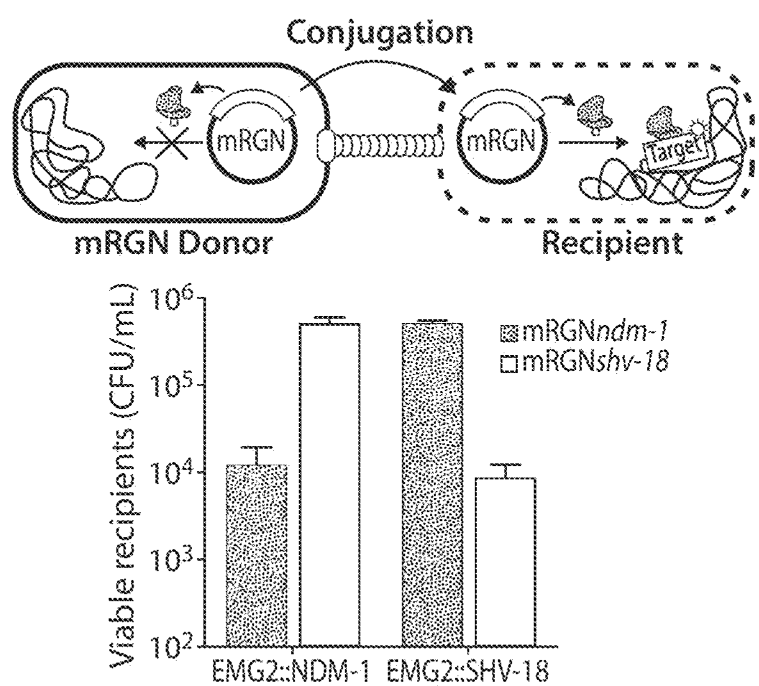
FIG. 17 shows a schematic design (top) of mobilizable RGNs (mRGNs) conjugated into target bacteria for selective removal of multidrug resistance. The graph (below) shows viable cell recipients. S17-1 λpir donor cells possessing mRGNndm-1 (black bars) or mRGNshv-18 (white bars) were mated at a donor:recipient ratio of 340±66:1 for 3 hours with EMG2 recipient cells containing chromosomally integrated ESBL resistance genes. Cultures were plated on LB+Cb to select for surviving recipient cells. Error bars indicate s.e.m. of nine independent biological replicates (n=9).
Figure 18:
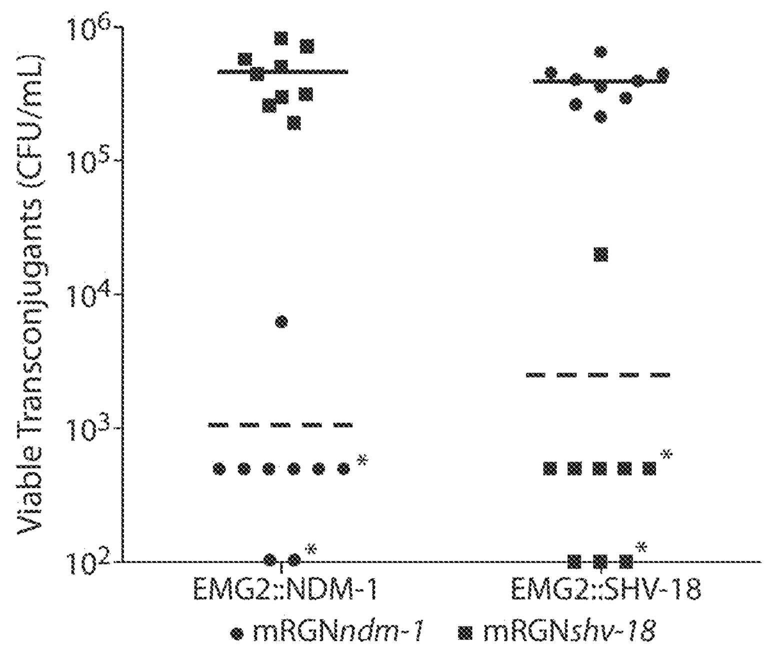
FIG. 18 shows a graph showing that transfer of incompatible mRGNs into *E. coli* yields reduced numbers of transconjugants. EMG2 strains that contain $bla_{NDM-1}$ (EMG2::NDM-1) or $bla_{SHV-18}$ (EMG2::SHV-18) integrated into their chromosome were mated with S17-1 λpir donor strains containing either mRGNndm-1 (circles) or mRGN-shv-18 (squares). Following three hours of mating, cell mixtures were plated onto LB+Cm+Cb to select for transconjugants. Transfer of an mRGN into cells containing the cognate target sequence (dashed line) reduced the number of viable transconjugants to the limit of detection (*) (100 CFU/mL or 500 CFU/mL for three or six of the biological replicates, respectively) in almost all cases. Nine biological replicates were performed for each condition (n=9).

Example 8: Mobilizable RNA-Guided Nucleases are Conjugated into Target Bacteria for Selective Removal of Multidrug Resistance To expand the utility of programmable nuclease circuits, R1162, a mobilizable broad-host-range IncQ-type plasmid (Meyer, R. *Plasmid* 62, 57-70 (2009)), was used as another platform to shuttle RGNs into target cells. This approach was used to selectively remove multidrug-resistant *E. coli*. High-efficiency mobilization of R1162 was achieved using *E. coli* S17-1, which has the conjugative machinery of plasmid RP4 integrated into its chromosome (Simon, R. et al. *Nat. Biotechnol.* 1, 784-791 (1983)). Although constrained by requirements for cell-cell contact, conjugative plasmids tend to possess the largest host ranges amongst all forms of horizontal gene transfer (Smillie, C. et al. *Microbiol. Mol. Biol. Rev.* 74, 434-52 (2010)) and there are no known recipient factors necessary for DNA uptake (Pérez-Mendoza, D. & de la Cruz, F. *BMC Genomics* 10, 71 (2009)). After 3-hour matings, transfer of a mobilizable RGN (mRGN) enabled a 40-60-fold reduction of carbenicillin-resistant recipient cells possessing target chromosomal antibiotic resistance determinants in the absence of any selection for the mRGN in the target cells (FIG. 17). Transfer of mRGNs into target cells yielded a 2-3 log reduction in transconjugants compared to controls, implying that conjugation efficiency, as opposed to RGN activity, sets the limit on mRGN efficacy in this context (FIG. 18).

Figure 19:
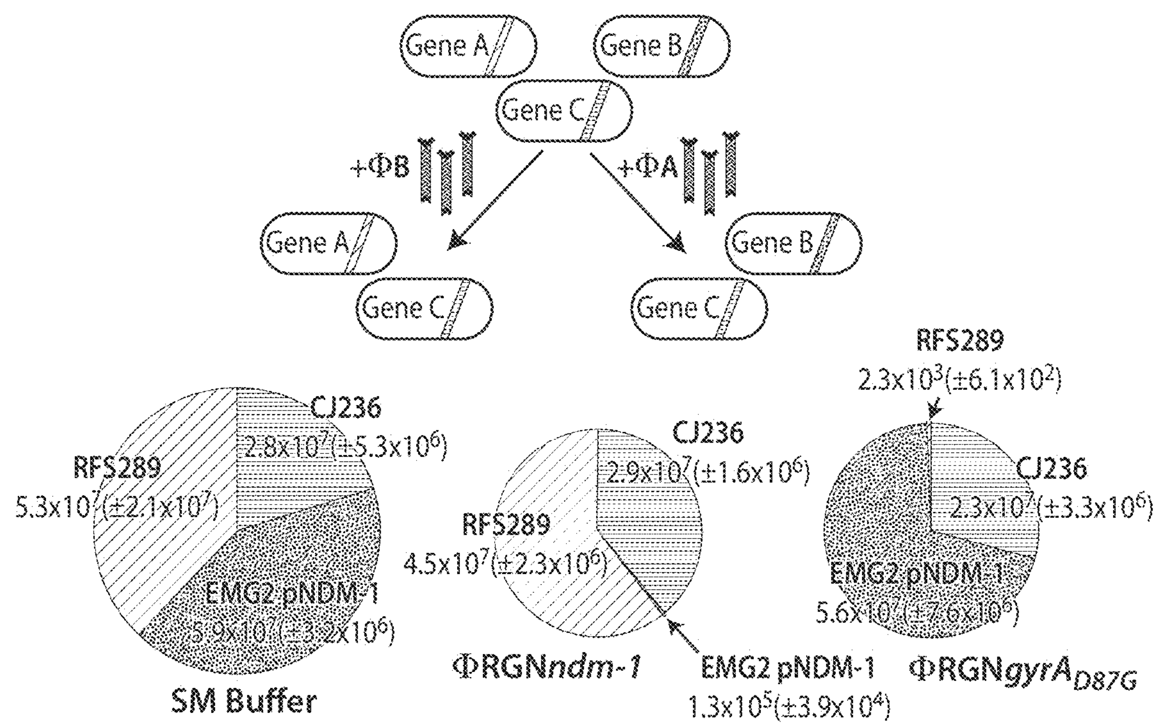
FIG. 19 shows that ΦRGNs can programmably remodel a synthetic microbial consortium. A synthetic population composed of three different *E. coli* strains was treated with SM buffer, ΦRGNndm-1 or ΦRGNgyr$A_{D87G}$ at an MOI ~100 and plated onto LB with chloramphenicol (Cm), streptomycin (Sm), or ofloxacin (Ofx) to enumerate viable cells of *E. coli* CJ236, EMG2 pNDM-1, or RFS289 strains, respectively. Circle area is proportional to total population size and numbers represent viable cell concentrations (CFU/mL) of each strain after the indicated treatment. The 95% confidence interval based on three independent experiments is indicated in parentheses (n=3).

Example 9: RNA-Guided Nucleases Sculpt the Composition of Complex Bacterial Populations In addition to implementing targeted antimicrobial therapies, programmable nuclease circuits can be used to sculpt the composition of complex bacterial populations (FIG. 19). Current therapies involving prebiotic, probiotic, and drug-based modification of the human microbiota have demonstrated potential for alleviating various disease states, but remain poorly characterized in terms of off-target effects and the specific mechanisms by which they act (Sonnenburg, J. L. & Fischbach, M. A. *Sci. Transl. Med.* 3, 78ps12 (2011)). In concert with the host range of the delivery vehicle, sequence-specific RGN activity can selectively remove bacteria with specific genomic contents. This can reduce the prevalence of unwanted genes, including antibiotic resistance and virulence loci, or metabolic pathways from bacterial communities without affecting bystanders. To demonstrate 'bacterial knockdowns' using RGNs, a synthetic consortium comprised of three *E. coli* strains with differential antibiotic resistance profiles was constructed. A β-lactam-resistant *E. coli* EMG2 pNDM-1, quinolone-resistant RFS289 (conferred by the chromosomal $gyrA_{D87G}$ variant), and chloramphenicol-resistant CJ236 were used. Application of ΦRGNndm-1 elicited >400-fold killing of EMG2 pNDM-1, while leaving RFS289 and CJ236 cell populations intact. Treatment with $ΦRGNgyrA_{D87G}$ resulted in >20,000-fold killing of RFS289 without a concomitant reduction in EMG2 pNDM-1 or CJ236 (FIG. 19). These results demonstrate that programmable nuclease circuits can selectively knockdown bacteria that contain target DNA sequences while allowing the remaining non-target bacteria to dominate the population. By pairing programmable nuclease circuits with broad-host-range phages or conjugative plasmids (Westwater, C. et al. *Microbiology* 148, 943-50

(2002); Filutowicz, M. et al. *Plasmid* 60, 38-44 (2008)), targeted 'bacterial knockdown' can selectively remove virulence and antibiotic resistance genes in pathogenic or commensal bacterial populations, enable functional studies of complex microbiota, and complement additive therapies, such as probiotics, for microbiome-associated disease by clearing specific niches or removing defined genes from bacterial populations.

Example 10: "Immunizing" Bacteria

Figure 24:
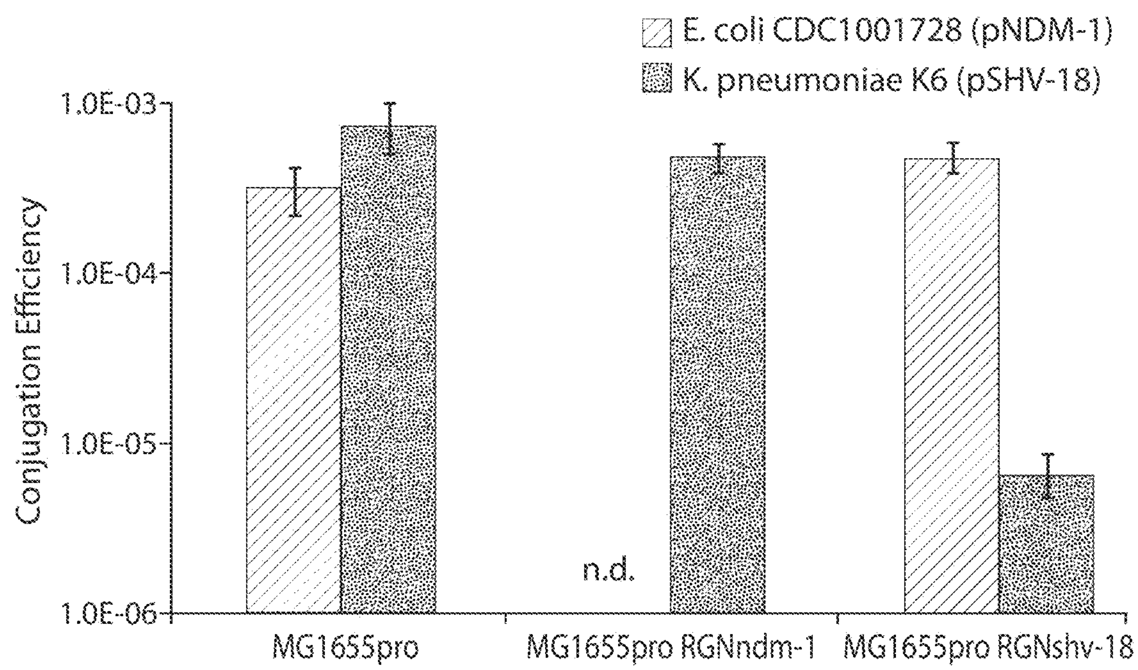
FIG. 24 shows graphs of data demonstrating that MG1655pro cells containing an RGN construct targeting either the $bla_{NDM-1}$ or $bla_{SHV-18}$ gene protects from receipt of a conjugative plasmid from *E. coli* CDC1001728 (containing a plasmid with $bla_{NDM-1}$) or *K. pneumoniae* (containing a plasmid with $bla_{SHV-18}$).

Programmable nuclease circuits delivered on plasmids in *E. coli* can prevent the incoming conjugation of plasmids with $bla_{NDM-1}$ and $bla_{SHV-18}$ antibiotic-resistance genes from clinical isolates of *Escherichia coli* (*E. coli*) and *Klebsiella pneumoniae* (*K. pneumonia*) (FIG. 24). Overnight cultures of donor cells (*K. pneumoniae* K6 containing a conjugative plasmid with the $bla_{SHV-18}$ gene or *E. coli* CDC1001728 containing a conjugative plasmid with the $bla_{NDM-1}$ gene) and recipient cells (*E. coli* MG1655pro, *E. coli* MG1655pro containing single-cutter $RGN_{ndm-1}$, or *E. coli* MG1655pro containing $RGN_{shv-18}$ cassettes) were grown overnight. These cells were grown to mid-log phase, mixed in equal ratios, centrifuged, resuspended, spotted onto sterile Whatman® No. 1 filters, placed on LB agar, and incubated at 37° C. for 1 hour. Filters were then removed and cells were recovered by vortexing. Cells were then serially diluted onto selective agar plates containing 50 μg/mL of carbenicillin (to select for donors), 100 μg/mL of streptinomycin (to select for recipients), and 50 μg/mL of carbenicillin plus 100 μg/mL of streptinomycin (to select for transconjugants, i.e., recipient cells that received the conjugative plasmid). Conjugation efficiencies were calculated as the number of transconjugants per donor cell. RGNs were highly effective at reducing conjugation of plasmids with antibiotic-resistance genes into recipient cells (FIG. 24). For example, RGNndm-1 specifically reduced the conjugation efficiency of $bla_{NDM-1}$ plasmids by greater than 100-fold. Similarly, RGNshv-18 specifically reduced the conjugation efficiency of $bla_{SHV-18}$ plasmids.

Example 11: Phagemid and Bacteriophage Delivery to Bacterial Cells

M13 bacteriophages ("M13 phages") and phagemids that express programmable nuclease circuits are engineered for delivery into *Escherichia coli* (*E. coli*) containing chromosomally integrated and plasmid-borne genes of interest (e.g., biothreat genes). One advantage of using phages for delivery of the programmable nuclease circuits is that they can replicate within infected cells and amplify themselves to achieve near-complete infection of a target population. One advantage of using phagemids for delivery is that they do not produce new infectious particles after delivery and, thus, are self-limited. As a result, phagemids must be packaged into high-titer and efficient phage particles to ensure near-complete infection of a target population.

M13 bacteriophage delivery vehicles of the invention are engineered by cloning a programmable RGN circuit expressing the trans-activating small RNA, the Cas9 endonuclease, and gDNAs into the multiple-cloning site of M13mp18. This phage vector enables straightforward blue-white screening of recombinant phages. M13 phage DNA is isolated through standard miniprep protocols for cloning. Recombinant phages are amplified in *E. coli* by infecting mid-log cell populations, removing the cells through centrifugation and filtration, and storing the supernatants where the phage particles are present. The phage stocks are titered to determine the number of viable phage particles through serial dilution and enumeration of plaque-forming units (pfu) on lawns of susceptible *E. coli.*

M13 phagemids of the invention are engineered by cloning an M13 origin of replication (f1) into vectors containing the programmable RGN circuits and a selectable antibiotic-resistance marker to aid in cloning. These phagemid vectors are placed into special packaging strains of bacteria that produce phage particles containing the phagemid (Chasteen, L., et al. *Nucleic acids research* 34, e145 (2006)). After growth of and phagemid packaging in these bacteria, the phage particles are purified by removing the bacteria cells through centrifugation and filtration of the resulting supernatant fluid where the phage particles are present. The number of phage particles containing the engineered phagemid is determined by exposing serial dilutions of these supernatants to phage-susceptible cells and counting the number of cells that subsequently demonstrate resistance to the antibiotic marker on the phagemid containing the programmable RGN circuit.

Genotypic and phenotypic assays are used to determine the effectiveness of M13 phages and phagemids at targeting plasmid-borne and chromosomally integrated genes, including antibiotic-resistance genes and virulence factors. DNA sequencing is used to determine the effects of RGNs on the target genes at the sequence level. For antibiotic-resistance genes such as $bla_{NDM-1}$, cells are plated on non-selective and selective plates to determine whether treatment with programmable RGN circuits reduces the number of bacteria that still display antibiotic resistance.

For virulence genes, specific phenotypic assays are performed. For example, assays for directly detecting the production of Stx have been described (Gould, L. H., et al. *MMWR. Recommendations and reports: Morbidity and mortality weekly report. Recommendations and reports/Centers for Disease Control* 58, 1-14 (2009)). Two methods are used to analyze stx targeting: a cytotoxicity-based assay and direct detection of the toxin by a Stx-specific ELISA. Cytotoxicity of spent culture medium from Stx2-producing bacteria is assessed by applying sterile-filtered supernatants from these cultures onto a monolayer of Vero cells (African green monkey kidney epithelial cells) and quantifying cell viability using a methyl tetrazolium (MTT) assay (Fotakis, G., et al. *Toxicology letters* 160, 171-177 (2006)). Vero cells are often used in such assays owing to an increased prevalence of the surface receptor $Gb_3$ and resulting heightened sensitivity to the toxin (Paton, J. C., et al. *Clin Microbiol Rev* 11, 450-479 (1998); Konowalchuk, J., et al. *Infect Immun* 18, 775-779 (1977)). Cytotoxicity due to Stx is further confirmed by demonstrating a loss of cytotoxicity in the presence of Stx-neutralizing antibodies (Karmali, M. A., et al. *J Infect Dis* 151, 775-782 (1985)). In addition to cytotoxicity assays, ELISA assays are used to titer the concentration of Stx and commercial kits such as the Premier™ EHEC Kit (Meridian Biosciences, Inc.) are used to evaluate sensitivity and specificity (Willford, J., et al. *J Food Prot* 72, 741-747 (2009); Staples, M., et al. Diagn Microbiol Infect Dis 73, 322-325 (2012)).

Example 12*: Escherichia coli* (*E. coli*) Urinary Tract Infection Models in Mice A urinary tract infection (UTI) model in mice is used to study the in vivo efficacy of phagemid and phage delivery of programmable nuclease circuits. The circuits are tested against *E. coli* with plasmid-borne and chromosomally integrated genes of interest (e.g., biothreat genes). Urinary catheters are inoculated with *E. coli* for 24 hours to establish infections. These urinary catheters are placed into mice and then exposed to intra-catheter treatments. The following delivery vehicles are used: phage carrying a programmable nuclease circuit, phagemids carrying a programmable nuclease circuit, control phages without a programmable nuclease circuit, and control phages with a non-cognate programmable nuclease circuit. Urine is collected at multiple time points and centrifuged to collect bacteria. Bacteria are plated on selective media to determine the proportion of cells that receive a programmable nuclease circuit (e.g., programmable RNA circuits, programmable TALEN circuits, or programmable ZFN circuits). Furthermore, genotypic assays, such as DNA sequencing, and phenotypic assays, such as antibiotic resistance and toxin expression are performed as described elsewhere herein.

Example 13: Programmable Nuclease Circuits Targeted Against Genes in Gram Negative and Gram-Positive Bacteria Programmable nuclease circuits (e.g., programmable RNA circuits, programmable TALEN circuits, or programmable ZFN circuits) targeting genes of interest in *Klebsiella pneumoniae* (*K. pneumoniae*), *Pseudomonas aeruginosa* (*P. aeruginosa*), and vancomycin-resistant *Enterococci* (VRE) are engineered. Targets of interest in *K. pneumoniae* include $bla_{SHV\text{-}18}$ and $bla_{NDM\text{-}1}$, which are plasmid-borne genes that confer high-level resistance to beta-lactam antibiotics. Targets of interest in *P. aeruginosa* include gyrA mutations, which are chromosomal mutations leading to resistance to quinolone antibiotics, efflux pump mutations, which are chromosomal mutations in genes such as mexR and mexS that confer multi-drug resistance, porin loss mutations, which are chromosomal mutations in genes such as oprD that confer resistance to imipenem resistance, and virulence factors such as pyoverdin and exotoxin A. Targets of interested in VRE include the vanA and vanB mutations that lead to vancomycin resistance (Eliopoulos, G. M., et al. *Clinical Infectious Diseases* 33, 210-219 (2001)).

Example 14: Load Programmable Nuclease Circuits onto Broad-Host-Range-Vectors

To permit programmable nuclease circuits (e.g., programmable RNA circuits, programmable TALEN circuits, or programmable ZFN circuits) to propagate broadly in different bacterial strains, the circuits are loaded onto plasmids with broad-host-range origins of replication. Plasmid origins of interest include those derived from the major broad-host-range incompatibility groups IncQ (e.g., RSF1010, R300B, R1162), IncW (e.g., pSa, pR388), IncP (e.g., R18, R68, RK2, RP1, RP4), and pBBR141-based (Lale, R., et al. *Broad-Host-Range Plasmid Vectors for Gene Expression in Bacteria in Strain Engineering*, Vol. 765 (ed. Williams, J. A.) 327-343 (Humana Press, 2011)). For example, the origin derived from pBBR1, a small plasmid isolated from *Bordetella bronchiseptica*, confers stable maintenance in *Pseudomonas, Klebsiella, Citrobacter, Shigella, Escherichia, Bordetella, Vibrio, Rhizobium* and other species (Antoine, R., et al. *Molecular microbiology* 6, 1785-1799 (1992)). pBBR1 does not belong to the common broad host range incompatibility groups IncP, IncQ, or IncW and is compatible with ColE1 and p15A plasmids, an important feature to help avoid exclusion from strains harboring native plasmids (Antoine, R., et al. (1992)). Of note, pBBR1 has been used successfully in a phagemid system and can be mobilized via conjugation (Antoine, R., et al. (1992); Westwater, C., et al. *Microbiology* (Reading, England) 148, 943-950 (2002)).

To express the programmable nuclease circuits, promoters that are active in the target organism are used. Broad-activity promoters that have been shown to be active in these hosts to drive expression of RGNs are used, such as the arabinose-inducible promoter $P_{BAD}$ (Damron, F. H., et al. *Applied and Environmental Microbiology* 79, 718-721 (2013)). Additional promoters include Plac and PL, among others (Lale, R., et al. *Broad-Host-Range Plasmid Vectors for Gene Expression in Bacteria in Strain Engineering*, Vol. 765 (ed. Williams, J. A.) 327-343 (Humana Press, 2011)). The strength of these expression systems are tested by performing quantitative RT-PCR on the RGN RNA. GFP is placed under the control of these expression systems and output is quantified using flow cytometry.

Example 15: In Vitro Assays to Test Broad-Host-Range Vectors Against Broad Sets of Pathogens Plasmid-exclusion assays are performed to determine the efficacy of programmable nuclease circuits (e.g., programmable RNA circuits, programmable TALEN circuits, or programmable ZFN circuits) against plasmid-borne target genes. Vectors (e.g., phagemids) carrying programmable nuclease circuits are transformed into target cells containing the plasmid-borne target genes, transformants are selected with antibiotics and are tested with genotypic assays and phenotypic assays. DNA sequencing is used to determine to what extent transformed cells maintain an intact target gene. In addition, antibiotic-resistance assays are used to determine whether transformed cells maintain antibiotic resistance. Effective RGNs may reduce the number of cells that exhibit the antibiotic-resistant phenotype. Phenotype-specific assays for biothreat genes such as toxins are also performed.

Transformation assays are performed to determine the efficacy of programmable nuclease circuits against chromosomally integrated target genes. Vectors carrying the programmable nuclease circuits are transformed into target cells with chromosomally integrated target genes, and transformants are selected with antibiotics. Transformation efficiencies are calculated and compare to transformation reactions where vectors carrying non-cognate programmable nuclease circuits are transformed into target-containing cells as well as when vectors carrying programmable nuclease circuits are transformed into non-target-containing cells. Effective programmable nuclease circuits may show reduced transformation efficiencies compared to the controls because the programmable nuclease circuits (e.g., programmable RNA circuits, programmable TALEN circuits, or programmable ZFN circuits) induce specific chromosomal DNA breaks that lead to cell death.

Example 16: Broad-Host-Range Phagemid Vehicles

Phagemids that can be packaged into engineered phages are engineered. Phage packaging signals are incorporated into broad-host-range phagemids carrying programmable. For example, phagemids derived from P1 phage are used. P1 phage can target many species, with its adsorption to cells being tied to a terminal glucose residue in Gram-negative LPS (Yarmolinksy, M. B., & Sternberg, N. The Bacteriophages First Edition (ed. Calendar, R.), 291-438 (Oxford University Press, 1988)). P1 phagemids have been used previously to package and deliver genetic information to species such as *E. coli, Shigella* spp., *K. pneumonia, P. aeruginosa*, and *Citrobacter freundii* (Yarmolinksy, M. B., & Sternberg, N. The Bacteriophages First Edition (ed. Calendar, R.), 291-438 (Oxford University Press, 1988)). In some cases, target bacterial populations have some cells that receive the target plasmid from transducing particles while others are infected by wild-type virulent phage particles that can propagate and spread. To circumvent this problem, a packaging strain of lysogenic bacteria has been engineered with the packaging signal from the native P1 deleted. This signal has been shown to be required for specific packaging of virulent P1 DNA into phage heads (Sternberg, N., et al. *Journal of molecular biology* 194, 469-479 (1987). Thus, this system more efficiently packages phagemids into P1 particles.

Using programmable nuclease circuits (e.g., programmable RNA circuits, programmable TALEN circuits, or programmable ZFN circuits) delivered via the P1 phagemid system, both defensive and offensive assays are performed against *K. pneumoniae* and *P. aeruginosa*, as described in the above Examples. The effectiveness of P1-delivered programmable nuclease circuits are characterized with genotypic and phenotypic assays.

Example 17: Probiotic Vehicles

Programmable nuclease circuits (e.g., programmable RNA circuits, programmable TALEN circuits, or programmable ZFN circuits) are engineered to be deliverable via conjugation from bacterial probiotics to target recipients by including plasmid mobilization and conjugation signals. Such systems have been used previously to move plasmids between a wide range of gram-negatives and gram-positives, yeast and mammalian cells.

The plasmid pRK2013 was used to mobilize the conjugative transfer of the plasmid pBBR1MCS-1 into *E. coli* MG1655Pro. Adapting a mechanism such as the promiscuous pRK system permits conjugation into many different species, while using a mechanism such as the well-studied F-plasmid of *E. coli* results in a more narrow range of delivery. The pRK machinery can transfer into many gram-negatives tested and human pathogens, such as *E. coli, P. aeruginosa, Bordetella pertussis, V. cholerae* and *K. pneumoniae.*

Implementation of conjugative plasmids as delivery vehicles will demonstrates their therapeutic potential for in situ genome editing. To render them mobile, programmable nuclease circuits are cloned into the pIP501 and RK2 plasmids, which mediate high efficiency gene transfer in gram-positive and gram-negative bacteria, respectively (Kolatka, K., et al. *Plasmid* 64, 119-134 (2010); Grohmann, E., et al. *Microbiol Mol Biol Rev* 67, 277-301, table of contents (2003)). Due to the large size of these plasmids, the constructs are introduced into pIP501 and RK2 in *E. coli* using recombination-based genetic engineering referred to as λ-Red recombineering (Sharan, S. K., et al. *Nat Protoc* 4, 206-223 (2009)). To model the effects of disseminating a toxic RGN in a naïve microbial population, a strain possessing a mobile programmable nuclease circuit is introduced into populations of VRE or NDM-1 *E. coli*. The rate of conjugative transfer and the kinetics of resistance reversal is to measured by plating the population on media selective for conjugants or antibiotic resistance.

Example 18: Tissue Cage Model

As described above, programmable nuclease circuits (e.g., programmable RNA circuits, programmable TALEN circuits, or programmable ZFN circuits) can be effective against *E. coli* containing undesirable genes with in vitro assays. Furthermore, in vivo assays have demonstrated delivery of synthetic gene circuits via phages to potentiate the activity of antibiotics in animal models of infection (Lu, T. K., et al. (2009)). These experiments are extended to test programmable nuclease circuits against *K. pneumoniae, P. aeruginosa*, and VRE to validate the generalizability of this strategy in vivo.

A mouse tissue cage model is used to study the effects of programmable nuclease circuits (e.g., programmable RNA circuits, programmable TALEN circuits, or programmable ZFN circuits) on *K. pneumoniae* and *P. aeruginosa* infections (Fernandez, J. *Curr Protoc Pharmacol* Chapter 13, Unit13A, 15 (2006)). Tissue cage models allow the growth of bacteria in animals over many days without killing the animals, and thus can mimic abscess conditions. *K. pneumoniae* and *P. aeruginosa* infections are established in these conditions and then treated with programmable nuclease circuits and associated controls delivered through P1 phagemids. Bacterial cells are sampled periodically before and after treatment to determine the effectiveness of therapy using genotypic and phenotypic assays.

Example 19: Gut Model

To demonstrate both the ability of programmable nuclease circuits (e.g., programmable RNA circuits, programmable TALEN circuits, or programmable ZFN circuits) to be used as therapeutics in antibiotic resistant infections and to carve out niches in a complex microbial population, an engineered probiotic *Lactobacillus rhamnosus* GG possessing the pIP501-RGN plasmid is used to prevent and treat VRE in a murine colonization model. Recent studies suggest that administration of probiotic *L. rhamnosus* GG can reduce VRE colonization in human patients (Szachta, P., et al. *Journal of clinical gastroenterology* 45, 872-877 (2011); Manley, K. J., et al. *The Medical journal of Australia* 186, 454-457 (2007)). This protective effect can be potentiated through the use of programmable nuclease circuits. The VRE colonization mouse model has been widely used and accurately depicts the antibiotic-dependent colonization of humans observed in the clinic (Rice, L. B., et al. *J Infect Dis* 199, 342-349 (2009)). Mice fed wild-type or engineered probiotics, or left untreated, are first orally dosed for two days with vancomycin and then various inocula of VRE on the third day. For the next 14 days, wild-type and engineered probiotics are administered to all three groups and levels of VRE colonization are monitored by plating fecal content on selective media. Changes in phylogenetic and metagenomic content of the mouse gut are observed throughout the experiment by 16S sequencing and high-throughput Illumina sequencing of mouse feces, respectively.

Example 20: Septicemia Model

To demonstrate the ability of programmable nuclease circuits (e.g., programmable RNA circuits, programmable TALEN circuits, or programmable ZFN circuits) to be used as therapeutics in antibiotic resistant infections, programmable nuclease loaded particles are used to save a murine model from septicemia. Carbapenem-resistant *E. coli* and *K. pneumoniae* are estimated to cause 50% mortality rates in the U.S. (Centers for Disease Control and Prevention, Antibiotic Resistance Threats in the United States, 2013 (2013)). Bacteria are injected via the intraperitoneal route into mice at an inoculum sufficient to induce mortality and are subsequently administered the treatment with appropriately tuned nuclease circuits. Antibiotics to which the infecting bacteria are resistant or non- or off-targeting particles will show no saving effects while the described particles can be shown to improve the survival outcome of infected mice.

In light of the rising tide of antibiotic resistance, interest in engineered cellular and viral therapeutics as potential biological solutions to infectious disease has resurged. Synthetic biology has conferred new functionalities to living systems, such as tumor detection (Xie, Z. et al. *Science* 333, 1307-11 (2011)), generation of therapeutic small molecules (Paddon, C. J. et al. *Nature* 496, 528-32 (2013)), novel tools for drug screening (Weber, W. et al. *Proc. Natl. Acad. Sci. U.S.A.* 105, 9994-8 (2008)), next-generation probiotics (Duan, F. & March, J. C. *Proc. Natl. Acad. Sci. U.S.A.* 107, 11260-4 (2010)), and bacteriophage therapeutics that can eradicate biofilms (Lu, T. K. & Collins, J. J. *Proc. Natl. Acad. Sci. U.S.A.* 104, 11197-202 (2007)), inhibit conjugation (Lin, A. et al. *PLoS One* 6, e19991 (2011)), and potentiate antibiotic activity in resistant populations (Lu, T. K. & Collins, J. *Proc. Natl. Acad. Sci. U.S.A.* 106, 4629-34 (2009); Edgar, R. et al. *Appl. Environ. Microbiol.* 78, 744-51 (2012)). Herein, transmissible CRISPR-Cas systems were shown to act as a platform for programmable antimicrobials that harness site-specific cleavage to induce cytotoxicity, activate toxin-antitoxin systems, resensitize bacterial populations to antibiotics and sculpt bacterial consortia. The present disclosure complements the recent understanding that the *Vibrio cholerae* phage, ICP1, encodes its own CRISPR-Cas system to counteract a host-encoded phage defense locus (Seed, K. D. et al. *Nature* 494, 489-91 (2013)) and that CRISPR-Cas constructs transformed into electrocompetent cell populations are incompatible with cells that contain cognate target sequences (Gomaa, A. A. et al. *MBio* 5, (2013); Jiang, W. et al. *Nat. Biotechnol.* 31, 233-9 (2013); Vercoe, R. B. et al. *PLoS Genet* 9, e1003454 (2013)). In contrast to previous data, the data provided herein shows that programmable nuclease circuits efficiently delivered via bacteriophages or conjugation can elicit sequence-specific toxicity even in the absence of artificial selection, such that CRISPR-Cas technology can be applied in situ for the removal of undesired genes from microbial populations and in vivo to treat infection. Moreover, programmable nuclease circuits of the present disclosure can be used, in some instances, to artificially activate plasmid-borne toxin-antitoxin systems, which has recently become an attractive antimicrobial strategy (Williams, J. J. & Hergenrother, P. J. *Trends Microbiol.* 20, 291-8 (2012)). Using DNA damage-responsive reporter constructs, programmable nuclease circuits were used in a diagnostic capacity to detect single nucleotide sequence differences. Phage-based therapies are dependent on their ability to deliver nucleic acids into bacteria, which can be resisted through a variety of mechanisms (Labrie, S. J. et al. *Nat. Rev. Microbiol.* 8, 317-27 (2010)). These delivery vehicles can be limited to a subset of bacteria defined by the chosen phage, such that the design of programmable antimicrobials may require additional considerations as to the phage platform chosen. However, rational modification to phage host range through tail fiber alterations (Lin, T.-Y. et al. *PLoS One* 7, e30954 (2012)) or the use of bacteriophage cocktails (Abedon, S. T. et al. *Bacteriophage* 1, 66-85 (2011)) can mitigate the host-range limitations of phage-based therapies. In order to augment the demonstration of programmable nuclease circuit applications, an additional delivery strategy was devised by using a mobilizable broad-host-range system to introduce programmable nuclease circuits to recipient cells via conjugation. The use of conjugative delivery from probiotics into target bacteria enables a platform where engineered cells could integrate complex environmental cues and execute lethal payload delivery, akin to previously described sentinel cells (Saeidi, N. et al. *Mol. Syst. Biol.* 7, 521 (2011)).

In summary, programmable nuclease circuits of the present disclosure address multidrug-resistant bacterial infections by enabling transmissible site-specific nucleases that can be programmed to enact selective pressure against specific genetic contexts. Due to the modularity and simplicity of CRISPR-Cas engineering, libraries of multiplexed ΦRGNs (or other Φ programmable nuclease circuits) can be rapidly constructed to simultaneously target a plethora of antibiotic resistance and virulence determinants, as well as to sculpt complex microbial communities. Moreover, because CRISPR-Cas is widely conserved in prokaryotes, the use of a variety different delivery systems enables programmable nuclease circuits that can address other clinically important multidrug-resistant pathogens, including Gram-positive organisms such as *Staphylococcus aureus* that currently have similarly limited treatment options (Van Hal, S. J. & Fowler, V. G. *Clin. Infect. Dis.* 56, 1779-88 (2013)). The addition of facile, sequence-informed rational design to a field dominated by time- and cost-intensive screening for broad-spectrum small-molecule antibiotics could have the potential to reinvigorate the dry pipeline of new antimicrobials.

Materials and Methods:

Strains and Culture Conditions

Unless otherwise noted, bacterial cultures were grown at 37° C. with LB medium (BD Difco). Where indicated, antibiotics were added to the growth medium to the following final concentrations: 100 μg/mL carbenicillin (Cb), 30 μg/mL kanamycin (Km), 25 μg/mL chloramphenicol (Cm), 100 μg/mL streptomycin (Sm), and 150 ng/mL ofloxacin (Ofx).

Strain Construction

*E. coli* EMG2 $Sm^R$ was generated by plating an overnight culture of *E. coli* EMG2 onto LB+Sm. Spontaneous resistant mutants were re-streaked onto LB+Sm and an isolated colony was picked and used as the recipient for conjugation of the multidrug resistance plasmids. Overnight cultures of EMG2 $Sm^R$, *E. coli* CDC1001728, and *K. pneumoniae* K6 were washed in sterile PBS and 100 μL of donor and recipient were spotted onto LB agar plates and incubated at 37° C. overnight. Transconjugants were harvested by scraping the cells in 1 mL of sterile PBS and plating onto LB+Sm+Cb. The chromosomal integrations of the β-lactamase genes and generation of EMG2 gyrAD87G were performed by λ-Red recombineering using the pSIM9 system (Datta, S. et al. *Gene* 379, 109-15 (2006)). Templates for integration at the non-essential lacZYA locus were generated by amplifying the blaNDM-1 and blaSHV-18 genes from lysates of CDC1001728 and K6 using the primers rcD77/78 and rcD73/74, respectively. Templates for construction of EMG2 $gyrA_{D87G}$ were obtained by amplifying gyrA from RFS289 using primers mmD155/161.

Plasmid Construction

To create the dual-guide RGN plasmids, an intermediate vector pZA-RGNØ which lacks a crRNA locus was created. The tracrRNA and $P_{L(tetO-1)}$ promoter were synthesized (Genewiz) and amplified using primers mmD98/99, Cas9 was amplified from pMJ806 (Jinek, M. et al. *Science* 337, 816-21 (2012)) using primers mmD74/75 and the vector backbone was amplified from pZA11G using primers mmD82/83. Each PCR product was purified and ligated by Gibson assembly (Gibson, D. G. et al. *Nat. Methods* 6, 343-5

(2009)). To create the final backbone vector for the RGN plasmids, the pBBR1 origin, chloramphenicol resistance marker, tL17 terminator, and crRNA locus cloning site were amplified from an intermediate vector pBBR1-MCS1-tL17 using mmD151/154, digested with NheI and SacI-HF, and ligated with pZA-RGNØ digested with SacI-HF and AvrII to create pZB-RGNØ. Digestion of this vector with PstI-HF and XbaI allowed for the insertion of assembled crRNA loci. The ΔtracrRNA pZB-RGNndm-1 plasmid was created by amplification of pZB-RGNndm-1 with mmD162/163, ClaI digestion, and self-ligation. The Cas9D10A mutant plasmids were constructed through site-directed mutagenesis of pZB-RGNndm-1 with primers mmD108/109 and the KAPA HiFi PCR kit (KAPA Biosystems).

The crRNA loci were constructed through isothermal annealing and ligation of short, single-stranded oligonucleotides (Integrated DNA Technologies). Each spacer and repeat piece was built by a corresponding oligo duplex connected to adjacent pieces by 6 bp overhangs. In addition, the terminal repeats are designed to contain a 17 bp extension comprised of a BsaI restriction site that generates an overhang that allows insertion into the pUC57-Km-crRNAØ backbone vector synthesized by Genewiz. The oligos used to build each RGN are listed in Table 2 and 3.

To assemble the CRISPR loci, 500 pmol of sense and antisense oligos in a given duplex were annealed by boiling for 10 minutes at 99° C. and cooled to room temperature. 300 pmol of each annealed duplex were combined with 15U of T4 polynucleotide kinase (Affymetrix), 400U of T4 DNA ligase (NEB), T4 ligase buffer (NEB) and ddH$_2$O to a volume of 20 μL. Following incubation at 25° C. for 1 hour, the reaction products were purified using a Qiagen QIAquick PCR Purification Kit. Purified products were digested for three hours with BsaI-HF and re-purified using QIAquick. To prepare the crRNA backbone vector, pUC57-Km-crRNAØ was amplified using primers mmD104/105, subsequently digested with BbsI to generate compatible overhangs, and ligated with the assembled crRNA loci. Positive clones of the crRNA loci were digested from the entry vector using PstI-HF and XbaI and ligated into pZB-RGNØ digested with the same enzymes to create the final RGN plasmids.

TABLE 2

Bacterial Strains and Plasmids

| Identifier | Strain/Plasmid | Relevant Features | Source/Reference |
|---|---|---|---|
| Bacterial Strains | | | |
| fRC149 | *Escherichia coli* EMG2 | F$^+$ | CGSC #4401 |
| fMM36 | *E. coli* CJ236 | FΔ(HindIII)::cat (Tra$^+$ Pil$^+$ Cam$^R$) | NEB #E4141S |
| fMM194 | *E. coli* RFS289 | F', gyrA$_{D87G}$ (Ofx$^R$) | CGSC #5742 |
| fMM269 | *E. coli* EMG2::NDM-1 | EMG2 ΔlacZYA::bla$_{NDM-1}$ | this study |
| fMM268 | *E. coli* EMG2::SHV-18 | EMG2 ΔlacZYA::bla$_{SHV-18}$ | this study |
| fMM384 | *E. coli* EMG2 gyrA$_{D87G}$ | EMG2 gyrA$_{D87G}$ (Ofx$^R$) | this study |
| fRC275 | *E. coli* EMG2 Sm$^R$ | EMG2 rpsL$_{K43N}$ (Sm$^R$) | this study |
| fRC301 | *E. coli* DH5αPRO | M13cp | Chasteen et al. 2006 |
| fMM425 | *E. coli* CDC1001728 | pNDM-1 | ATCC BAA-2469 |
| fMM278 | *E. coli* S17-1 λpir | RP4-2-Tc::Mu-Km::Tn7 | Simon et al. 1983 |
| fMM362 | *E. coli* EMG2 pNDM-1 | pNDM-1 from ATCC BAA-2469 | this study |
| fMM426 | *Klebsiella pneumoniae* K6 | pSHV-18 | ATCC #700603 |
| fRC280 | *E. coli* EMG2 pSHV-18 | pSHV-18 from ATCC #700603 | this study |
| fMM427 | *E. coli* O157:H7 43888 | eae$^+$ | ATCC #43888 |
| fMM428 | *E. coli* O157:H7 43888 F' | F' from CJ236 | this study |
| RGN Plasmids | | | |
| pMM178 | pRGNndm1 | RGN targeting bla$_{NDM-1}$ | this study |
| pMM282 | pRGNndm1(Cas9D10A) | RGNndm1 (cas9 mutation) | this study |
| pMM281 | pRGNndm1(ΔtracrRNA) | RGNndm1 (tracrRNA deletion) | this study |
| pMM228 | pRGNshv-18 | RGN targeting bla$_{SHV-18}$ | this study |
| pMM417 | mRGNshv-18 | Mobilizable RGN targeting bla$_{SHV-18}$ | this study |
| pMM441 | mRGNndm-1 | Mobilizable RGN targeting bla$_{NDM-1}$ | this study |
| RGN Phagemids | | | |
| pRC327 | pΦRGNndm1 | Km$^R$ | this study |
| pRC329 | pΦRGNshv18 | Km$^R$ | this study |
| pRC331 | pΦRGNndm1/shv18 | Km$^R$ | this study |
| pRC328 | pΦRGNgyrA$_{D87G}$ | Km$^R$ | this study |
| pRC362 | pΦRGNeae | Km$^R$ | this study |
| Clinical Plasmids | | | |
| pMM425 | pNDM-1 | bla$_{NDM-1}$ | ATCC BAA-2469 |
| pMM426 | pSHV-18 | bla$_{SHV-18}$ | ATCC #700603 |
| Other Plasmids | | | |
| pRC218 | pMJ806 (Addgene 39312) | encodes Cas9 from *S. pyogenes* | Jinek et al. 2012 |
| pMM153 | pZE12-gfp | ColE1 gfp control plasmid, Cb$^R$ | Lutz et al. 1997 |
| pMM234 | pZE-bla$_{NDM-1}$-gfp | ColE1 bla$_{NDM-1}$, gfp | this study |
| pMM154 | pZA12-gfp | p15A gfp control plasmid, Cb$^R$ | Lutz et al. 1997 |
| pMM235 | pZA-bla$_{NDM-1}$-gfp | p15A bla$_{NDM-1}$, gfp | this study |
| pMM253 | pSIM9 | recombineering machinery, Cm$^R$ | Datta et al. 2006 |

TABLE 2-continued

| Bacterial Strains and Plasmids | | | |
|---|---|---|---|
| Identifier | Strain/Plasmid | Relevant Features | Source/Reference |
| pMM4 | pZEf-gfp | phagemid vector, $Km^R$ | this study |
| pMM395 | pZA31-gfp | p15A gfp control plasmid, $Cm^R$ | Lutz et al. 1997 |
| pMM398 | pZA31-pemI | p15A pemI expression plasmid, $Cm^R$ | this study |
| pMM444 | pZE1LG | ColE1 $P_{L(lexO)}$-gfp SOS-responsive plasmid, $Cb^R$ | Dwyer et al. 2007 |
| pMM447 | pZA3LG | p15a $P_{L(lexO)}$-gfp SOS-responsive plasmid, $Cm^R$ | this study |
| pMM364 | R1162 | Mobilizable wild-type plasmid | Richard Meyer |

TABLE 3

| Primers and Oligos | | |
|---|---|---|
| Identifier | Name | Sequence |
| | | Primers |
| mmD3 | SHV18-Chk-F | ATGCGTTATTTTCGCCTGTGTA (SEQ ID NO: 11) |
| mmD4 | SHV-18-Chk-R | TTAGCGTTGCCAGTGCTCG (SEQ ID NO: 12) |
| mmD8 | pNDM1-XhoI-F | CATGCGCTCGAGGCTCAGCTTGTTGATTATCATATG (SEQ ID NO: 13) |
| mmD9 | NDM1-SacI-R | CATAAGGAGCTCTCAGCGCAGCTTGTCGGCCA (SEQ ID NO: 14) |
| mmD74 | GpLtetO-SpCas9-F | CACTGACCGAATTCATTAAAGAGGAGAAAGGTGCG GCCGCATGCATCACCATCACCATCACATGGATAAG AAATACTCAATAGGCTTAG (SEQ ID NO: 15) |
| mmD75 | GT1-SpCas9-R | TTCGACTGAGCCTTTCGTTTTATTTGATGCCTCTAGT CAGTCACCTCCTAGCTGACTCAA (SEQ ID NO: 16) |
| mmD82 | GSpCRISPR-T1-F | TATGCTGTTTTGAATGGTCTCCATTCTCTAGAGGCA TCAAATAAAACGAAAGGCTCAGT (SEQ ID NO: 17) |
| mmD83 | GSptracrRNA-amp-R | AACCAAAAAAACAAGCGCTTTCAAAACGCGTCGAC AGGGTGAAGACGAAAGGGCCTCGTG (SEQ ID NO: 18) |
| mmD98 | mmS1-F | CTATAAAAATAGGCGTATCACGAGGCCC (SEQ ID NO: 19) |
| mmD99 | mmS1-R | TTGAGTATTTCTTATCCATGTGATGGTGATGG (SEQ ID NO: 20) |
| mmD104 | GGSpySpacer-F | GAGCATGAAGACCATTCAGCACACTGAGACTTGTT GAGTTC (SEQ ID NO: 21) |
| mmD105 | GGSpySpacer-R | GAGCATGAAGACCCCTCGCTCGTAGACTATTTTTGT CTAAAAAATTTCGT (SEQ ID NO: 22) |
| mmD108 | SpyCas9D10A-F | GCTATCGGCACAAATAGCGTCGGATG (SEQ ID NO: 23) |
| mmD109 | SpyCas9D10A-R | TAAGCCTATTGAGTATTTCTTATCCATCGAGG (SEQ ID NO: 24) |
| mmD112 | Cas9-400-Chk-R | GATAGATAGTTGGATATTTCTCATGATAAG (SEQ ID NO: 25) |
| mmD113 | Cas9-900-Chk-F | CTGAAATAACTAAGGCTCCCCTATC (SEQ ID NO: 26) |
| mmD114 | Cas9-1.8K-Chk-F | GATAGGGAGATGATTGAGGAAAGAC (SEQ ID NO: 27) |

TABLE 3-continued

| Primers and Oligos | | |
|---|---|---|
| Identifier | Name | Sequence |
| mmD115 | Cas9-2.8K-Chk-F | CGCATGAATACTAAATACGATGAAAATG (SEQ ID NO: 28) |
| mmD151 | NheI-tL17pBBR1-SpyCRISPR-F | CATGATGCTAGCACCCTGCAGAGCTTCTAGATGATG ATTAAGGATCTATTTTTTTGGGCG (SEQ ID NO: 29) |
| mmD153 | Cas9-End-Chk-F | GTGCATATAACAAACATAGAGAC (SEQ ID NO: 30) |
| mmD154 | Lutz-BtwAbProm-R | CCTCGTGATACGCCTATTTTTATAGGTTAATG (SEQ ID NO: 31) |
| mmD155 | gyrA-F | CACCACTCATTGCCACATTCCTTGTG (SEQ ID NO: 32) |
| mmD161 | gyrA-R | CGGCTTCAAATTTAGCGATCTCTTC (SEQ ID NO: 33) |
| mmD162 | notracrRNA-ClaI-F | ATCGATATCGATTCCCTATCAGTGATAGAGATTGAC (SEQ ID NO: 34) |
| mmD163 | notracrRNA-ClaI-R | CATGATATCGATAGGGTGAAGACGAAAGGGCCTCG (SEQ ID NO: 35) |
| mmD234 | NDM-1-Start-F | GATGGAATTGCCCAATATTATGCACCC (SEQ ID NO: 36) |
| mmD247 | SpeI-catCRISPR-F | CACTCATCGCAGTCGGCCTATTGG (SEQ ID NO: 37) |
| mmD248 | XmaI-catCRISPR-R | CATGATcccgggGGACAGCAAGCGAACCATTTTTTTG GG (SEQ ID NO: 37) |
| mmD253 | KpnI-pemI-F | CATGATGGTACCATGCATACCACTCGACTGAAGAA GGTTG (SEQ ID NO: 39) |
| mmD254 | BamHI-pemI-R | CATGATGGATCCTCAGATTTCCTCCTGACCAGCCG (SEQ ID NO: 40) |
| mmD266 | XmaI-R1162-F | catgatcccgggGACAGACGTCATACTAGATATCAAG CGAC (SEQ ID NO: 41) |
| mmD267 | SpeI-R1162-R | catgatactagtGGAGCAGAAGAGCATACATCTGGAAG (SEQ ID NO: 42) |
| rcD11 | cam-3-F | ACGTCTCATTTTCGCCAGAT (SEQ ID NO: 43) |
| rcD73 | pSHV18-KIlacZYA-F | GGCTTTACACTTTATGCTTCCGGCTCGTATGTTGTGT GGAATTGTGAGCGGATAACAATTCTTTTGCTTTGCC ACGGAAC (SEQ ID NO: 44) |
| rcD74 | SHV18-KIlacZYA-R | TTAAACTGACGATTCAACTTTATAATCTTTGAAATA ATAGTGCTTATCCCGGTCGTTTATCTACGAGCCGGA TAACGC (SEQ ID NO: 45) |
| rcD77 | pNDM1-KIlacZYA-F | GGCTTTACACTTTATGCTTCCGGCTCGTATGTTGTGT GGAATTGTGAGCGGATAACAATTGCTCAGCTTGTTG ATTATCATATG (SEQ ID NO: 46) |
| rcD78 | NDM1-KIlacZYA-R | TTAAACTGACGATTCAACTTTATAATCTTTGAAATA ATAGTGCTTATCCCGGTCGTTTATTCAGCGCAGCTT GTCGGCCA (SEQ ID NO: 47) |
| rcD169 | XmaI-CRISPR-R | CATGATCCCGGGGTTTTATGGACAGCAAGCGAACC (SEQ ID NO: 48) |
| rcD183 | AvrII-CRISPR-F | CATGATCCTAGGCGTCTAAGAAACCATTATTATCAT GACATTAACC (SEQ ID NO: 49) |
| rcD184 | XmaI-pZEfS-noGFP-F | CATGATCCCGGGCAGAAGATCCTGCAGGGCCTTC (SEQ ID NO: 50) |

TABLE 3-continued

| Identifier | Name | Sequence |
|---|---|---|
| | Primers and Oligos | |
| rcD185 | AvrII-pZEfS-noGFP-R | CATGATCCTAGGAAATTGTAAACGTTAATATTTTGTTAAAATTCGC (SEQ ID NO: 51) |
| | Oligos | |
| mmO11 | SP-T-GG-Cap-1 | CATGAGGGTCTCACGAGGTTTTAGAGCTATGCTGTTTTGAATGGTCCCAAAAC (SEQ ID NO: 52) |
| mmO14 | SP-B-GGCap-5 | CATGAGGGTCTCCTGAAGTTTTGGGACCATTCAAAACAGCATAGCTCTAAAAC (SEQ ID NO: 53) |
| mmO17 | SP-T-ndm1-6 | GGGCAGTCGCTTCCAACGGTTTGA (SEQ ID NO: 54) |
| mmO18 | SP-B-ndm1-6 | TGACGATCAAACCGTTGGAAGCGA (SEQ ID NO: 55) |
| mmO19 | SP-T-ndm1R-7 | TCGTCAGTTTTAGAGCTATGCTGTTTTGAATGGTCCCAAAAC (SEQ ID NO: 56) |
| mmO20 | SP-B-Rshv18-2 | ATTTGCGTTTTGGGACCATTCAAAACAGCATAGCTCTAAAAC (SEQ ID NO: 57) |
| mmO21 | SP-T-shv18-2 | GCAAATTAAACTAAGCGAAAGCCA (SEQ ID NO: 58) |
| mmO22 | SP-B-shv18-2 | GACAGCTGGCTTTCGCTTAGTTTA (SEQ ID NO: 59) |
| mmO23 | SP-T-shv18-2-3Cap | GCTGTCGTTTTAGAGCTATGCTGTTTTGAATGGTCCCAAAACTTCAGGAGACCCTCATG (SEQ ID NO: 60) |
| mmO58 | SP-B-ndm1-1-Cap5 | CTGCCCGTTTTGGGACCATTCAAAACAGCATAGCTCTAAAACCTCGTGAGACCCTCATG (SEQ ID NO: 61) |
| mmO87 | SP-B-gyrA111-Cap5 | TGGTATGTTTTGGGACCATTCAAAACAGCATAGCTCTAAAACCTCGTGAGACCCTCATG (SEQ ID NO: 62) |
| mmO88 | SP-T-gyrA111 | ATACCATCCCCATGGTGACTCGGC (SEQ ID NO: 63) |
| mmO89 | SP-B-gyrA111 | TAGACCGCCGAGTCACCATGGGGA (SEQ ID NO: 64) |
| mmO90 | SP-T-gyrA111-Cap3 | GGTCTAGTTTTAGAGCTATGCTGTTTTGAATGGTCCCAAAACTTCAGGAGACCCTCATG (SEQ ID NO: 65) |
| mmO92 | SP-B-shv18-2-Cap5 | ATTTGCGTTTTGGGACCATTCAAAACAGCATAGCTCTAAAACCTCGTGAGACCCTCATG (SEQ ID NO: 66) |
| mmO115 | ndm1-1-T | TTCCAACGGTTTGATCGTCAGTTTTA (SEQ ID NO: 67) |
| mmO116 | ndm1-1-B | TGACGATCAAACCGTTGGAAGCTAGC (SEQ ID NO: 68) |
| mmO121 | shv18-2-T | CTAAGCGAAAGCCAGCTGTCGTTTTA (SEQ ID NO: 69) |
| mmO122 | shv18-2-B | GACAGCTGGCTTTCGCTTAGGCTAGC (SEQ ID NO: 70) |
| mmO204 | SP-B-eae1-Cap5 | GAGTCAGTTTTGGGACCATTCAAAACAGCATAGCTCTAAAACCTCGTGAGACCCTCATG (SEQ ID NO: 71) |
| mmO205 | SP-T-eae1 | TGACTCCCGCTTTACGGCAAATTT (SEQ ID NO: 72) |

TABLE 3-continued

| Primers and Oligos | | |
|---|---|---|
| Identifier | Name | Sequence |
| mmO206 | SP-B-eae1 | GCACCTAAATTTGCCGTAAAGCGG (SEQ ID NO: 73) |
| mmO207 | SP-T-eae1-Cap3 | AGGTGCGTTTTAGAGCTATGCTGTTTTGAATGGTCC CAAAACTTCAGGAGACCCTCATG (SEQ ID NO: 74) |

Phagemid vector pZEf-gfp was created previously by adding the f1 origin amplified from the yeast shuttle pRS series (Sikorski, R. S. & Hieter, P. *Genetics* 122, 19-27 (1989)) into pZE22-gfp (Lutz, R. & Bujard, H. *Nucleic Acids Res.* 25, 1203-10 (1997)). The RGN constructs consisting of the genes encoding the tracrRNA, Cas9, and a sequence-targeting crRNA were amplified as a single product from the respective pZB-RGN vectors using KAPA HiFi polymerase (Kapa Biosystems) with primers rcD169/183 and digested with AvrII and XmaI (New England Biolabs). These inserts were ligated with a backbone derived from amplifying the kanamycin resistance cassette, ColE1 replication origin, and the f1 origin required for packaging into M13 particles off of pZEf-gfp with primers rcD184/185 and digesting with the same enzymes. Ligated plasmids were transformed into *E. coli* DH5αPro for sequence verification and plasmid purification.

The pZE-bla$_{NDM-1}$-gfp and pZA-bla$_{NDM-1}$-gfp vectors were constructed by swapping the antibiotic resistance cassette of the Lutz-Bujard vectors pZE12-gfp and pZA12-gfp (Lutz, R. & Bujard, H. (1997)). The bla$_{NDM-1}$ gene was amplified from a lysate of CDC1001728 using primers mmD8/9 and the PCR product was digested with SacI-HF and XhoI. The digested product was ligated into the Lutz-Bujard vectors digested with the same enzymes.

The PemI antitoxin complementation plasmid pZA31-pemI was created by first amplifying pSHV-18 with mmD253/254. The PCR product was digested with BamHI and KpnI and ligated with the large fragment of a pZA31G digest with the same enzymes. The SOS-responsive pZA3LG reporter plasmid was derived from pZE1LG (Dwyer, D. J. et al. *Mol Syst Biol* 3, (2007)) by swapping the origin of replication and antibiotic resistance marker with pZA31G using AatII and AvrII as restriction enzymes.

Mobilizable RGNs were created by first amplifying the R1162 replication origin and oriT using mmD266/267. The chloramphenicol selection marker and RGN locus were amplified from pRGNndm-1 and pRGNshv-18 with mmD247/248. PCR products were digested with SpeI and XmaI, ligated and transformed into *E. coli* S17-1 λpir to create the donor cells used in matings.

Minimum Inhibitory Concentration (MIC) Determination

MICs were determined by broth microdilution using LB broth according to the CLSI guidelines (Clinical and Laboratory Standards Institute. Methods for Dilution Antimicrobial Susceptibility Tests for Bacteria That Grow Aerobically; Approved Standard—Seventh Edition. 64 (2006)).

Transformation Assays

Overnight cultures were diluted 1:100 in fresh LB and grown to an optical density ($OD_{600}$) of approximately 0.3-0.5. Following 15 minutes of incubation on ice, cultured cells were centrifuged at 3200×g, and pellets were resuspended in one tenth volume of TSS buffer (LB, 10% polyethylene glycol, 5% dimethyl sulfoxide, 50 mM $Mg^{2+}$ at pH 6.5) (Chung, C. T. et al. *Proc. Natl. Acad. Sci. U.S.A.* 86, 2172-5 (1989)). A 100 μL aliquot of cells was incubated with 10 ng of RGN plasmid DNA. Plasmids were purified from the DH5αPro cloning host using a QIAGEN® QIAprep Spin Miniprep Kit and the concentration was determined using a Quant-iT PicoGreen dsDNA Assay Kit (Invitrogen). Following 30 minutes of incubation on ice, cells were heat shocked at 42° C. for 30 seconds, returned to ice for 2 minutes and recovered for 1.5 hours at 37° C. in 1 ml of SOC broth (HIMEDIA®). For the chromosomal target assay, serial dilutions of cells were plated on LB+Cm to select for transformants. Plates were incubated overnight at 37° C., and the number of colony forming units (CFU) were enumerated the following day. Transformation efficiency was used to assess whether the given RGN plasmid was toxic to cells and was calculated as the CFU/mL per μg of DNA transformed.

For the episomal target assay, following recovery, cultures washed in fresh LB, diluted 1:100 in LB supplemented with chloramphenicol to select for transformants and incubated for 16 hours at 37° C. Samples washed in sterile PBS, serially diluted and plated on LB+Cm and LB+Cm+Cb or analyzed by flow cytometry. Colony counts were enumerated the following day and plasmid loss was inferred by calculating the ratio of $Cb^R$+$Cm^R$ CFUs to $Cm^R$ CFUs.

Overnight cultures of RGN transformants were also diluted 1:100 in sterile PBS, aliquoted in duplicates in a 96-well plate and immediately assayed using a BD LSR-Fortessa cell analyzer. Cells were consistently gated by side scatter and forward scatter across independent biological replicates. Fluorescence measurements were performed using a 488-nm argon excitation laser. The GFP gate and laser voltages were initially determined using untreated pZE-bla$_{Z}$-gfp and EMG2 cells as positive and negative controls, respectively, and implemented across biological replicates. BD FACSDIVA software was used for data acquisition and analysis.

Sequence Analysis

Escape mutants from transformation assays were re-isolated by passaging surviving colonies onto LB+Cm+Cb. DNA isolation for escape sequencing analysis was performed by either extracting plasmid DNA from isolated escape mutants using the Qiagen QIAprep Spin Miniprep Kit or by amplifying the integrated target locus using primers mmD9/234 or mmD3/4, for bla$_{NDM-1}$ and bla$_{SHV-18}$, respectively. Sequencing was performed by Genewiz using the primers mmD112-115/153 and rcD11 for analysis of the RGN plasmids and mmD3 or mmD234 for examination of the integrated resistance genes.

Phagemid Purification

Phagemids encoding the RGNs were purified using the Qiagen QIAprep Spin Miniprep Kit (Qiagen) and transformed into *E. coli* DH5αPro along with the m13cp helper plasmid for generation of phagemid-loaded M13 particles (Chasteen, L. et al. *Nucleic Acids Res.* 34, e145 (2006)). Strains were inoculated and grown overnight in 250 mL LB+Cm+Km to maintain m13cp and the phagemid, respectively. Cells were pelleted and the supernatant fluid containing the phagemid particles was passed through a 0.2 μm filter. M13 phagemid particles were precipitated by the addition of 5% polyethylene glycol (PEG-6000) and 0.5 M NaCl and incubation overnight at 4° C. (Westwater, C. et al. *Antimicrob. Agents Chemother.* 47, 1301-7 (2003)) and pelleted at 12,000×g for 1 h. Purified phagemid pellets were resuspended gently in SM buffer (50 mM Tris-HCl [pH 7.5], 100 mM NaCl, 10 mM $MgSO_4$) and stored at 4° C. Titers were measured by incubating sample dilutions with *E. coli* EMG2 for 30 minutes and enumerating transductants by plating on LB and LB+Km. Titers were defined in $TFU_{100}$/mL, which is the concentration of phagemid at which ~100% of a recipient population would be transduced at a multiplicity of infection (MOI) of 1.

Phagemid Kill Assays

Cultures were inoculated and grown overnight in LB with appropriate antibiotics at 37° C. with shaking. The following day, overnights were subcultured 1:100 into 3 mL LB (no antibiotics) and grown at 37° C. with shaking until the $OD_{600}$ reached ~0.8. Cultures were diluted into LB to ~$10^8$ CFU/mL for pNDM-1 and pSHV-18 assays or ~$10^6$ CFU/mL for gyrAD87G and EHEC assays and 245 μL of the suspension was added to 5 μL of purified phagemid stock in a 96-well plate and incubated static at 37° C. The number of viable cells in samples at each interval during the time-course or at 2 h for endpoint assays was determined by serial dilution and spot plating onto LB, LB+Cb, and LB+Km to analyze cytotoxicity, plasmid loss, and phagemid delivery, respectively. Initial suspensions were also diluted and plated onto LB to quantify the initial bacterial inocula. Colonies were enumerated after 8-9 h incubation at 37° C. to calculate cell viability (CFU/mL) and averaged over three independent experiments. Non-linear curve fitting of the time-course to an exponential decay curve was performed using GraphPad Prism.

*Galleria mellonella* Model

Larvae of the model organism *Galleria mellonella* (Desbois, A. P. & Coote, P. J. *Adv. Appl. Microbiol.* 78, 25-53 (2012)) were purchased from Vanderhorst Wholesale, Inc. (St. Marys, Ohio, USA) and received in the final larval instar for survival assays. Larvae were removed from food source, allowed to acclimate for at least 24 h at room temperature in the dark, and used within 4 days of receipt. For all injections, a KDS100 (KD Scientific) or Pump 11 Elite (Harvard Apparatus) automated syringe pump was set to dispense a 10 μL volume at a flow rate of ~1 μL/s through a 1 mL syringe (BD) and 26 G needle (BD). To prepare bacteria for injection, an overnight culture of *E. coli* 0157:H7 43888 F' was subcultured in Dulbecco's Modified Eagle Medium (Gibco) for 4 hours at 37° C. with shaking until $OD_{600}$~0.6. Cultures were washed twice in PBS and diluted to a concentration of approximately $4\times10^5$ CFU/mL. In accordance with other studies (Ramarao, N. et al. *J. Vis. Exp. e*4392 (2012)), twenty larvae per treatment group were randomly selected based on size (150-250 mg) and excluded based on poor health as evidenced by limited activity, dark coloration, or reduced turgor prior to experiments. Larvae were delivered injections without blinding of either PBS or bacteria behind the final left proleg. Approximately an hour after the first injection, SM buffer or ΦRGN treatment was administered behind the final right proleg. Larvae were incubated at 37° C. and survival was monitored at 12 hour intervals for 72 hours, with death indicated by lack of movement and unresponsiveness to touch (Desbois, A. P. & Coote, P. J. *Adv. Appl. Microbiol.* 78, 25-53 (2012)). Kaplan-Meier survival curves were generated on the data pooled from four independent experiments and analyzed with the log-rank test using GraphPad Prism.

LexA Reporter Assay

Overnight cultures of EMG2 WT, EMG2 pNDM-1 and EMG2 gyrAD87G containing the SOS-responsive reporter plasmid pZA3LG were diluted 1:50 in LB and incubated with either SM buffer, ΦRGNndm-1 and ΦRGNgyrAD87G at MOI ~5 for two hours at 37° C. Cultures were diluted 1:5 in 250 μL of sterile PBS and analyzed using an BD LSR Fortessa cell analyzer, as above. BD FACSDIVA software was used for data acquisition and analysis was performed using FlowJo software.

Bacterial Matings

Donor and recipient strains grown overnight in LB with appropriate antibiotics were diluted 1:100 in fresh media and grown to an $OD_{600}$~1.0. Cells were pelleted, resuspended in sterile PBS and mating pairs were mixed at a donor to recipient ratio of 340±66:1. Mating mixtures were pelleted, resuspended in 20 μL of PBS and spotted onto nitrocellulose filters placed on LB agar plates. Initial bacterial suspensions were serially diluted and plated on LB agar plates to quantify the initial inocula. Matings proceeded at 37° C. for 3 h with a single mixing step. At 90 minutes, mating mixtures were collected by vigorously vortexing the filters in 1 mL sterile PBS. Cells were pelleted, resuspended in 20 μL PBS and re-seeded onto filters and incubated as above for the remaining 90 minutes. At the end of the h mating, cells were again recovered by vigorously vortexing the filters in 1 mL sterile PBS. Mating mixtures were serially diluted in PBS and plated onto LB+Cb to select for total number of Cb-resistant recipient cells and LB+Cb+Cm to select for transconjugants. Colonies were enumerated following overnight incubation at 37° C. to determine viable cell counts and were averaged over nine independent biological replicates.

Synthetic Consortia Remodeling

*E. coli* CJ236, EMG2 pNDM-1, and RFS289 strains grown overnight in LB with appropriate antibiotics were diluted 1:100 into fresh LB (no antibiotics) and grown to $OD_{600}$~0.8. Cultures were seeded into fresh LB such that the initial mixture contained ~$1\times10^6$ CFU/mL of each strain and 245 μL of the suspension was added to 5 μL of SM buffer or purified ΦRGNndm-1 or ΦRGNgyr$AD_{87G}$ in triplicate in a 96-well plate and spotted onto LB+Cm, +Sm, and +Ofx to quantify the initial concentration of CJ236, EMG2 pNDM-1, and RFS289, respectively. Samples were then incubated, plated, and enumerated as in phagemid kill assays. The composition of the synthetic ecosystem under each treatment condition was determined by counting viable colonies on plates selective for each strain as above and data were calculated as viable cell concentration (CFU/mL) averaged over three biological replicates.

Data Analysis and Statistics

Data points in figures indicate the mean of at least three biological replicates (n>3), where applicable. Error bars shown depict the standard error of the mean. All data were recorded and analyzed using GraphPad Prism version 6.0 (GraphPad Software, San Diego, Calif., USA).

TABLE 4

| CRISPR Loci | |
|---|---|
| RGN | Oligos (mmO---) |
| RGNndm-1 | 11/58, 17/18, 59/14 |
| RGNshv-18 | 11/92, 21/22, 23/14 |

TABLE 4-continued

| CRISPR Loci | |
|---|---|
| RGN | Oligos (mmO---) |
| RGNgyrA$_{D87G}$ | 11/87, 88/89, 90/14 |
| RGNndm-1/shv-18 | 11/58, 17/18, 19/20, 21/22, 23/14 |
| RGNeae | 11/204, 205/206, 207/14 |

ADDITIONAL SEQUENCES

Sample sequence for dual-guide RGN construct, comprising of the tracrRNA, pLtetO promoter, Cas9, T1 terminator and the variable crRNA. The variable 30 bp spacer sequence is denoted by 'N' residues.

```
CCATTATTATCATGACATTAACCTATAAAAATAGGCGTATCACGAGGCCC
TTTCGTCTTCACCCTGTCGACGCGTTTGAAAGCGCTTGTTTTTTTGGTT
TGCAGTCAGAGTAGAATAGAAGTATCAAAAAAAGCACCGACTCGGTGCCA
CTTTTTCAAGTTGATAACGGACTAGCCTTATTTTAACTTGCTATGCTGTT
TTGAATGGTTCCAACAAGATTATTTTATAACTTTTATAACAAATAATCAA
GGAGAAATTCAAAGAAATTTATCAGCCATAAAACAATACTTAATACTATA
GAATGATAACAAAATAAACTACTTTTTAAAAGAATTTTGTGTTATAATCT
ATTTATTATTAAGTATTGGGATCGATTCCCTATCAGTGATAGAGATTGAC
ATCCCTATCAGTGATAGAGATACTGAGCACATCAGCAGGACGCACTGACC
GAATTCATTAAAGAGGAGAAAGGTGCGGCCGCATGCATCACCATCACCAT
CACATGGATAAGAAATACTCAATAGGCTTAGATATCGGCACAAATAGCGT
CGGATGGGCGGTGATCACTGATGAATATAAGGTTCCGTCTAAAAAGTTCA
AGGTTCTGGGAAATACAGACCGCCACAGTATCAAAAAAAAATCTTATAGGG
GCTCTTTTATTTGACAGTGGAGAGACAGCGGAAGCGACTCGTCTCAAACG
GACAGCTCGTAGAAGGTATACACGTCGGAAGAATCGTATTTGTTATCTAC
AGGAGATTTTTTCAAATGAGATGGCGAAAGTAGATGATAGTTTCTTTCAT
CGACTTGAAGAGTCTTTTTTGGTGGAAGAAGACAAGAAGCATGAACGTCA
TCCTATTTTTGGAAATATAGTAGATGAAGTTGCTTATCATGAGAAATATC
CAACTATCTATCATCTGCGAAAAAAATTGGTAGATTCTACTGATAAAGCG
GATTTGCGCTTAATCTATTTGGCCTTAGCGCATATGATTAAGTTTCGTGG
TCATTTTTTGATTGAGGGAGATTTAAATCCTGATAATAGTGATGTGGACA
AACTATTTATCCAGTTGGTACAAACCTACAATCAATTATTTGAAGAAAAC
CCTATTAACGCAAGTGGAGTAGATGCTAAAGCGATTCTTTCTGCACGATT
GAGTAAATCAAGACGATTAGAAAATCTCATTGCTCAGCTCCCCGGTGAGA
AGAAAAATGGCTTATTTGGGAATCTCATTGCTTTGTCATTGGGTTTGACC
CCTAATTTTAAATCAAATTTTGATTTGGCAGAAGATGCTAAATTACAGCT
TTCAAAAGATACTTACGATGATGATTTAGATAATTTATTGGCGCAAATTG
GAGATCAATATGCTGATTTGTTTTTGGCAGCTAAGAATTTATCAGATGCT
ATTTTACTTTCAGATATCCTAAGAGTAAATACTGAAATAACTAAGGCTCC
CCTATCAGCTTCAATGATTAAACGCTACGATGAACATCATCAAGACTTGA
CTCTTTTAAAAGCTTTAGTTCGACAACAACTTCCAGAAAAGTATAAAGAA
ATCTTTTTTGATCAATCAAAAAACGGATATGCAGGTTATATTGATGGGGG
AGCTAGCCAAGAAGAATTTTATAAATTTATCAAACCAATTTTAGAAAAAA
TGGATGGTACTGAGGAATTATTGGTGAAACTAAATCGTGAAGATTTGCTG
CGCAAGCAACGGACCTTTGACAACGGCTCTATTCCCCATCAAATTCACTT
GGGTGAGCTGCATGCTATTTTGAGAAGACAAGAAGACTTTTATCCATTTT
TAAAAGACAATCGTGAGAAGATTGAAAAAATCTTGACTTTTCGAATTCCT
TATTATGTTGGTCCATTGGCGCGTGGCAATAGTCGTTTTGCATGGATGAC
TCGGAAGTCTGAAGAAACAATTACCCCATGGAATTTTGAAGAAGTTGTCG
ATAAAGGTGCTTCAGCTCAATCATTTATTGAACGCATGACAAACTTTGAT
AAAAATCTTCCAAATGAAAAAGTACTACCAAAACATAGTTTGCTTTATGA
GTATTTTACGGTTTATAACGAATTGACAAAGGTCAAATATGTTACTGAAG
GAATGCGAAAACCAGCATTTCTTTCAGGTGAACAGAAGAAAGCCATTGTT
GATTTACTCTTCAAAACAAATCGAAAAGTAACCGTTAAGCAATTAAAAGA
AGATTATTTCAAAAAAATAGAATGTTTTGATAGTGTTGAAATTTCAGGAG
TTGAAGATAGATTTAATGCTTCATTAGGTACCTACCATGATTTGCTAAAA
ATTATTAAAGATAAAGATTTTTTGGATAATGAAGAAAATGAAGATATCTT
AGAGGATATTGTTTTAACATTGACCTTATTTGAAGATAGGGAGATGATTG
AGGAAAGACTTAAAACATATGCTCACCTCTTTGATGATAAGGTGATGAAA
CAGCTTAAACGTCGCCGTTATACTGGTTGGGGACGTTTGTCTCGAAAATT
GATTAATGGTATTAGGGATAAGCAATCTGGCAAAACAATATTAGATTTTT
TGAAATCAGATGGTTTTGCCAATCGCAATTTTATGCAGCTGATCCATGAT
GATAGTTTGACATTTAAAGAAGACATTCAAAAAGCACAAGTGTCTGGACA
AGGCGATAGTTTACATGAACATATTGCAAATTTAGCTGGTAGCCCTGCTA
TTAAAAAAGGTATTTTACAGACTGTAAAAGTTGTTGATGAATTGGTCAAA
GTAATGGGGCGGCATAAGCCAGAAAATATCGTTATTGAAATGGCACGTGA
AAATCAGACAACTCAAAAGGGCCAGAAAAATTCGCGAGAGCGTATGAAAC
GAATCGAAGAAGGTATCAAAGAATTAGGAAGTCAGATTCTTAAAGAGCAT
CCTGTTGAAAATACTCAATTGCAAAATGAAAAGCTCTATCTCTATTATCT
CCAAAATGGAAGAGACATGTATGTGGACCAAGAATTAGATATTAATCGTT
TAAGTGATTATGATGTCGATCACATTGTTCCACAAAGTTTCCTTAAAGAC
GATTCAATAGACAATAAGGTCTTAACGCGTTCTGATAAAAATCGTGGTAA
```

-continued

```
ATCGGATAACGTTCCAAGTGAAGAAGTAGTCAAAAAGATGAAAAACTATT
GGAGACAACTTCTAAACGCCAAGTTAATCACTCAACGTAAGTTTGATAAT
TTAACGAAAGCTGAACGTGGAGGTTTGAGTGAACTTGATAAAGCTGGTTT
TATCAAACGCCAATTGGTTGAAACTCGCCAAATCACTAAGCATGTGGCAC
AAATTTTGGATAGTCGCATGAATACTAAATACGATGAAAATGATAAACTT
ATTCGAGAGGTTAAAGTGATTACCTTAAAATCTAAATTAGTTTCTGACTT
CCGAAAAGATTTCCAATTCTATAAAGTACGTGAGATTAACAATTACCATC
ATGCCCATGATGCGTATCTAAATGCCGTCGTTGGAACTGCTTTGATTAAG
AAATATCCAAAACTTGAATCGGAGTTTGTCTATGGTGATTATAAAGTTTA
TGATGTTCGTAAAATGATTGCTAAGTCTGAGCAAGAAATAGGCAAAGCAA
CCGCAAAATATTTCTTTTACTCTAATATCATGAACTTCTTCAAAACAGAA
ATTACACTTGCAAATGGAGAGATTCGCAAACGCCCTCTAATCGAAACTAA
TGGGGAAACTGGAGAAATTGTCTGGGATAAAGGGCGAGATTTTGCCACAG
TGCGCAAAGTATTGTCCATGCCCCAAGTCAATATTGTCAAGAAAACAGAA
GTACAGACAGGCGGATTCTCCAAGGAGTCAATTTTACCAAAAAGAAATTC
GGACAAGCTTATTGCTCGTAAAAAAGACTGGGATCCAAAAAAATATGGTG
GTTTTGATAGTCCAACGGTAGCTTATTCAGTCCTAGTGGTTGCTAAGGTG
GAAAAAGGGAAATCGAAGAAGTTAAAATCCGTTAAAGAGTTACTAGGGAT
CACAATTATGGAAAGAAGTTCCTTTGAAAAAAATCCGATTGACTTTTTAG
AAGCTAAAGGATATAAGGAAGTTAAAAAAGACTTAATCATTAAACTACCT
AAATATAGTCTTTTTGAGTTAGAAAACGGTCGTAAACGGATGCTGGCTAG
TGCCGGAGAATTACAAAAAGGAAATGAGCTGGCTCTGCCAAGCAAATATG
TGAATTTTTTATATTTAGCTAGTCATTATGAAAAGTTGAAGGGTAGTCCA
GAAGATAACGAACAAAAACAATTGTTTGTGGAGCAGCATAAGCATTATTT
AGATGAGATTATTGAGCAAATCAGTGAATTTTCTAAGCGTGTTATTTTAG
CAGATGCCAATTTAGATAAAGTTCTTAGTGCATATAACAAACATAGAGAA
AACCAATACGTGAACAAGCAGAAAATATTATTCATCTTATTTACGTTGAC
GAATCTTGGAGCTCCCGCTGCTTTTAAATATTTTGATACAACAATTGATC
GTAAACGATATACGTCTACAAAAGAAGTTTTAGATGCCACTCTTATCCAT
CAATCCATCACTGGTCTTTATGAAACACGCATTGATTTGAGTCAGCTAGG
AGGTGACTGACTCGAGCTAGAGGCATCAAATAAAACGAAAGGCTCAGTCG
AAAGACTGGGCCTTTCGTTTTATCTGTTGTTTGTCGGTGAACGCTCTCCT
GAGTAGGACAAATCCGCCGCCCTAGACCTAGCACCCTGCAGAACTATATG
ATTTTCCGCAGTATATTTTAGATGAAGATTATTTCTTAATAACTAAAAAT
ATGGTATAATACTCTTAATAAATGCAGTAATACAGGGGCTTTTCAAGACT
GAAGTCTAGCTGAGACAAATAGTGCGATTACGAAATTTTTTAGACAAAAA
TAGTCTACGAGGTTTTAGAGCTATGCTGTTTTGAATGGTCCCAAAACNNN
NNNNNNNNNNNNNNNNNNNNNNNNNNNGTTTTAGAGCTATGCTGTTTTGA
ATGGTCCCAAAACTTCAGCACACTGAGACTTGTTGAGTTCCATGTTTTAG
AGCTATGCTGTTTTGAATGGTCTCCATTCTCTAGATGATGATTAAGGATC
TATTTTTTTGGGCGGGGCCGCCCAAAAAAAT
```

Sample spacer sequences for dual-guide RGNs:

Target: gfp

SEQ ID NO: 2

```
TAATGGGCACAAATTTTCTGTCAGTGGAGA
```

Target: bla$_{NDM-1}$

SEQ ID NO: 3

```
GGGCAGTCGCTTCCAACGGTTTGATCGTCA
```

Target: bla$_{SHV-18}$

SEQ ID NO: 4

```
GCAAATTAAACTAAGCGAAAGCCAGCTGTC
```

Target: gyrA111

SEQ ID NO: 5

```
ATACCATCCCCATGGTGACTCGGCGGTCT
```

Sample sequence for the single-guide RGN construct, comprising of pLtetO promoter, Cas9, T1 terminator and the variable crRNA. The variable 20 bp spacer sequence is denoted by 'N' residues.

SEQ ID NO: 6

```
TCCCTATCAGTGATAGAGATTGACATCCCTATCAGTGATAGAGATACTGA
GCACATCAGCAGGACGCACTGACCGAATTCATTAAAGAGGAGAAAGGTGC
GGCCGCATGCATCACCATCACCATCACATGGATAAGAAATACTCAATAGG
CTTAGATATCGGCACAAATAGCGTCGGATGGGCGGTGATCACTGATGAAT
ATAAGGTTCCGTCTAAAAAGTTCAAGGTTCTGGGAAATACAGACCGCCAC
AGTATCAAAAAAAATCTTATAGGGGCTCTTTTATTTGACAGTGGAGAGAC
AGCGGAAGCGACTCGTCTCAAACGGACAGCTCGTAGAAGGTATACACGTC
GGAAGAATCGTATTTGTTATCTACAGGAGATTTTTTCAAATGAGATGGCG
AAAGTAGATGATAGTTTCTTTCATCGACTTGAAGAGTCTTTTTTGGTGGA
AGAAGACAAGAAGCATGAACGTCATCCTATTTTTGGAAATATAGTAGATG
AAGTTGCTTATCATGAGAAATATCCAACTATCTATCATCTGCGAAAAAAA
TTGGTAGATTCTACTGATAAAGCGGATTTGCGCTTAATCTATTTGGCCTT
AGCGCATATGATTAAGTTTCGTGGTCATTTTTTGATTGAGGGAGATTTAA
ATCCTGATAATAGTGATGTGGACAAACTATTTATCCAGTTGGTACAAACC
```

-continued

```
TACAATCAATTATTTGAAGAAAACCCTATTAACGCAAGTGGAGTAGATGC
GTAAAGCGATTCTTTCTCACGATTGAGTAAATCAAGACGATTAGAAAATC
TCATTGCTCAGCTCCCCGGTGAGAAGAAAAATGGCTTATTTGGGAATCTC
ATTGCTTTGTCATTGGGTTTGACCCCTAATTTTAAATCAAATTTTGATTT
GGCAGAAGATGCTAAATTACAGCTTTCAAAAGATACTTACGATGATGATT
TAGATAATTTATTGGCGCAAATTGGAGATCAATATGCTGATTTGTTTTTG
GCAGCTAAGAATTTATCAGATGCTATTTTACTTTCAGATATCCTAAGAGT
AAATACTGAAATAACTAAGGCTCCCCTATCAGCTTCAATGATTAAACGCT
ACGATGAACATCATCAAGACTTGACTCTTTTAAAAGCTTTAGTTCGACAA
CAACTTCCAGAAAAGTATAAAGAAATCTTTTTTGATCAATCAAAAAACGG
ATATGCAGGTTATATTGATGGGGGAGCTAGCCAAGAAGAATTTTATAAAT
TTATCAAACCAATTTTAGAAAAAATGGATGGTACTGAGGAATTATTGGTG
AAACTAAATCGTGAAGATTTGCTGCGCAAGCAACGGACCTTTGACAACGG
CTCTATTCCCCATCAAATTCACTTGGGTGAGCTGCATGCTATTTTGAGAA
GACAAGAAGACTTTTATCCATTTTTAAAAGACAATCGTGAGAAGATTGAA
AAAATCTTGACTTTTCGAATTCCTTATTATGTTGGTCCATTGGCGCGTGG
CAATAGTCGTTTTGCATGGATGACTCGGAAGTCTGAAGAAACAATTACCC
CATGGAATTTTGAAGAAGTTGTCGATAAAGGTGCTTCAGCTCAATCATTT
ATTGAACGCATGACAAACTTTGATAAAAATCTTCCAAATGAAAAAGTACT
ACCAAAACATAGTTTGCTTTATGAGTATTTTACGGTTTATAACGAATTGA
CAAAGGTCAAATATGTTACTGAAGGAATGCGAAAACCAGCATTTCTTTCA
GGTGAACAGAAGAAAGCCATTGTTGATTTACTCTTCAAAACAAATCGAAA
AGTAACCGTTAAGCAATTAAAAGAAGATTATTTCAAAAAAATAGAATGTT
TTGATAGTGTTGAAATTTCAGGAGTTGAAGATAGATTTAATGCTTCATTA
GGTACCTACCATGATTTGCTAAAAATTATTAAAGATAAAGATTTTTTGGA
TAATGAAGAAAATGAAGATATCTTAGAGGATATTGTTTTAACATTGACCT
TATTTGAAGATAGGGAGATGATTGAGGAAAGACTTAAAACATATGCTCAC
CTCTTTGATGATAAGGTGATGAAACAGCTTAAACGTCGCCGTTATACTGG
TTGGGGACGTTTGTCTCGAAAATTGATTAATGGTATTAGGGATAAGCAAT
CTGGCAAAACAATATTAGATTTTTTGAAATCAGATGGTTTTGCCAATCGC
AATTTTATGCAGCTGATCCATGATGATAGTTTGACATTTAAAGAAGACAT
TCAAAAAGCACAAGTGTCTGGACAAGGCGATAGTTTACATGAACATATTG
CAAATTTAGCTGGTAGCCCTGCTATTAAAAAAGGTATTTTACAGACTGTA
AAAGTTGTTGATGAATTGGTCAAAGTAATGGGGCGGCATAAGCCAGAAAA
TATCGTTATTGAAATGGCACGTGAAAATCAGACAACTCAAAAGGGCCAGA
AAAATTCGCGAGAGCGTATGAAACGAATCGAAGAAGGTATCAAAGAATTA
GGAAGTCAGATTCTTAAAGAGCATCCTGTTGAAAATACTCAATTGCAAAA
TGAAAAGCTCTATCTCTATTATCTCCAAAATGGAAGAGACATGTATGTGG
ACCAAGAATTAGATATTAATCGTTTAAGTGATTATGATGTCGATCACATT
GTTCCACAAAGTTTCCTTAAAGACGATTCAATAGACAATAAGGTCTTAAC
GCGTTCTGATAAAAATCGTGGTAAATCGGATAACGTTCCAAGTGAAGAAG
TAGTCAAAAAGATGAAAAACTATTGGAGACAACTTCTAAACGCCAAGTTA
ATCACTCAACGTAAGTTTGATAATTTAACGAAAGCTGAACGTGGAGGTTT
GAGTGAACTTGATAAAGCTGGTTTTATCAAACGCCAATTGGTTGAAACTC
GCCAAATCACTAAGCATGTGGCACAAATTTTGGATAGTCGCATGAATACT
AAATACGATGAAAATGATAAACTTATTCGAGAGGTTAAAGTGATTACCTT
AAAATCTAAATTAGTTTCTGACTTCCGAAAAGATTTCCAATTCTATAAAG
TACGTGAGATTAACAATTACCATCATGCCCATGATGCGTATCTAAATGCC
GTCGTTGGAACTGCTTTGATTAAGAAATATCCAAAACTTGAATCGGAGTT
TGTCTATGGTGATTATAAAGTTTATGATGTTCGTAAAATGATTGCTAAGT
CTGAGCAAGAAATAGGCAAAGCAACCGCAAAATATTTCTTTTACTCTAAT
ATCATGAACTTCTTCAAAACAGAAATTACACTTGCAAATGGAGAGATTCG
CAAACGCCCTCTAATCGAAACTAATGGGGAAACTGGAGAAATTGTCTGGG
ATAAAGGGCGAGATTTTGCCACAGTGCGCAAAGTATTGTCCATGCCCCAA
GTCAATATTGTCAAGAAAACAGAAGTACAGACAGGCGGATTCTCCAAGGA
GTCAATTTTACCAAAAAGAAATTCGGACAAGCTTATTGCTCGTAAAAAAG
ACTGGGATCCAAAAAAATATGGTGGTTTTGATAGTCCAACGGTAGCTTAT
TCAGTCCTAGTGGTTGCTAAGGTGGAAAAAGGGAAATCGAAGAAGTTAAA
ATCCGTTAAAGAGTTACTAGGGATCACAATTATGGAAAGAAGTTCCTTTG
AAAAAAATCCGATTGACTTTTTAGAAGCTAAAGGATATAAGGAAGTTAAA
AAAGACTTAATCATTAAACTACCTAAATATAGTCTTTTTGAGTTAGAAAA
CGGTCGTAAACGGATGCTGGCTAGTGCCGGAGAATTACAAAAAGGAAATG
AGCTGGCTCTGCCAAGCAAATATGTGAATTTTTTATATTTAGCTAGTCAT
TATGAAAAGTTGAAGGGTAGTCCAGAAGATAACGAACAAAAACAATTGTT
TGTGGAGCAGCATAAGCATTATTTAGATGAGATTATTGAGCAAATCAGTG
AATTTTCTAAGCGTGTTATTTTAGCAGATGCCAATTTAGATAAAGTTCTT
AGTGCATATAACAAACATAGAGACAAACCAATACGTGAACAAGCAGAAAA
TATTATTCATTTATTTACGTTGACGAATCTTGGAGCTCCCGCTGCTTTTA
AATATTTTGATACAACAATTGATCGTAAACGATATACGTCTACAAAAGAA
GTTTTAGATGCCACTCTTATCCATCAATCCATCACTGGTCTTTATGAAAC
ACGCATTGATTTGAGTCAGCTAGGAGGTGACTGACTCGAGCTAGAGGCAT
CAAATAAAACGAAAGGCTCAGTCGAAAGACTGGGCCTTTCGTTTTATCTG
TTGTTTGTCGGTGAACGCTCTCCTGAGTAGGACAAATCCGCCGCCCTAGA
CCTAGCACCCTGCAGTTGACAGCTAGCTCAGTCCTAGGTATAATGCTAGC
NNNNNNNNNNNNNNNNNNNNGTTTTAGAGCTAGAAATAGCAAGTTAAAAT
AAGGCTAGTCCGTTATCAACTTGAAAAAGTGGCACCGAGTCGGTGCTTTT
TTTCTAGATGATGATTAAGGATCTATTTTTTTGGGCGGGGCCGCCCAAAA
AAAT
```

-continued

Sample spacer sequences for single-guide RGNs.

Target: gfp

SEQ ID NO: 7

AAATTTTCTGTCAGTGGAGA

Target: $bla_{NDM-1}$

SEQ ID NO: 8

TTCCAACGGTTTGATCGTCA

Target: $bla_{SHV-18}$

SEQ ID NO: 9

CTAAGCGAAAGCCAGCTGTC

Target: gyrA111

SEQ ID NO: 10

CATGGTGACTCGGCGGTCTA

The indefinite articles "a" and "an," as used herein in the specification and in the claims, unless clearly indicated to the contrary, should be understood to mean "at least one."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements).

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements).

It should also be understood that, unless clearly indicated to the contrary, in any methods claimed herein that include more than one step or act, the order of the steps or acts of the method is not necessarily limited to the order in which the steps or acts of the method are recited.

All references (e.g., published journal articles, books, etc.), patents and patent applications disclosed herein are incorporated by reference with respect to the subject matter for which each is cited, which, in some cases, may encompass the entirety of the document.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of detecting a nucleic acid of interest in a viable bacterial cell, comprising delivering to a human subject at least one delivery vehicle that comprises:

(a) a nucleic acid comprising a promoter operably linked to nucleotide sequences encoding a programmable nuclease circuit that induces a double-strand break in the nucleic acid of interest in the bacterial cell in the human subject;

(b) a nucleic acid comprising a RecA promoter or a LexO promoter operably linked to a gene encoding a reporter molecule, wherein the RecA promoter or the LexO promoter activates expression of the reporter molecule in the presence of the double-strand break; and (c) detecting presence or absence of the nucleic acid of interest based on expression of the reporter molecule in the viable bacterial cell.

2. The method of claim 1, wherein step (c) comprises detecting transcription or translation of the reporter molecule.

3. The method of claim 1, wherein the programmable nuclease circuit comprises an RNA-guided nuclease.

4. The method of claim 3, wherein the programmable nuclease circuit comprises a Cas9 nuclease, a guide RNA (gRNA), and/or a transactivating small RNA (tracrRNA) derived from the Type II CRISPR-Cas system of *Streptococcus pyogenes.*

5. The method of claim 4, wherein the gRNA and the tracrRNA form a chimeric single-guide RNA molecule.

6. The method of claim 1, wherein the programmable nuclease circuit comprises a transcriptional activator like (TAL)-effector nuclease (TALEN) or a zinc finger nuclease (ZFN).

7. The method of claim 1, wherein the delivery vehicle is a bacteriophage.

8. The method of claim 1, wherein the delivery vehicle is a phagemid.

9. The method of claim 1, wherein the delivery vehicle is a donor bacterial cell.

10. The method of claim 9, wherein the donor bacterial cell is a commensal bacterial cell.

11. The method of claim 10, wherein the commensal bacterial cell is loaded with at least one conjugative plasmid containing the nucleic acid of (a) and/or (b).

12. The method of claim 11, wherein the at least one conjugative plasmid comprises a broad-host-range origin of replication.

13. The method of claim 1, wherein the bacterial cells are pathogenic bacterial cells.

14. The method of claim 13, wherein the pathogenic bacterial cells are selected from extended-spectrum beta-lactamase-producing (ESBL) *Escherichia coli*, ESBL *Klebsiella pneumonia, Pseudomonas aeruginosa*, vancomycin-resistant *Enterococcus* (VRE), methicillin-resistant *Staphylococcus aureus* (MRSA), multidrug-resistant (MDR) *Acinetobacter baumannii*, and MDR *Enterobacter* spp.

15. The method of claim 1, wherein the nucleic acid of interest includes a mutation.

16. The method of claim 15, wherein the mutation is a single nucleotide polymorphism (SNP).

17. The method of claim 1, wherein the nucleic acid of interest comprises a virulence factor gene, a toxin gene, an antibiotic resistance gene, a remodeling gene or a modulatory gene.

18. The method of claim 17, wherein the nucleic acid of interest comprises an antibiotic resistance gene that confers aminoglycoside resistance, beta-lactam resistance, daptomycin resistance, macrolide-lincosamide-streptogramin B resistance, quinolone resistance, trimethoprim/sulfonamide resistance or vancomycin resistance.

19. The method of claim 1, wherein the promoter of (a) is an inducible promoter.

20. The method of claim 1, wherein the reporter molecule is a fluorescent protein.

* * * * *